US012721899B2

(12) United States Patent
Wang et al.

(10) Patent No.: US 12,721,899 B2
(45) Date of Patent: Sep. 1, 2026

(54) PHARMACEUTICAL COMPOSITIONS COMPRISING AN ANTI-CLAUDIN 18.2 ANTIBODY-DRUG CONJUGATE AND METHOD OF USE THEREOF TO TREAT A TUMOR OR CANCER

(71) Applicants: JIANGSU HENGRUI PHARMACEUTICALS CO., LTD., Lianyungang (CN); SHANGHAI HENGRUI PHARMACEUTICAL CO., LTD., Shanghai (CN)

(72) Inventors: Zhiwan Wang, Shanghai (CN); Tingting Wu, Shanghai (CN); Xun Liu, Shanghai (CN)

(73) Assignees: JIANGSU HENGRUI PHARMACEUTICALS CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 663 days.

(21) Appl. No.: 18/029,075

(22) PCT Filed: Sep. 30, 2021

(86) PCT No.: PCT/CN2021/122031

§ 371 (c)(1),
(2) Date: Mar. 28, 2023

(87) PCT Pub. No.: WO2022/068914

PCT Pub. Date: Apr. 7, 2022

(65) Prior Publication Data

US 2024/0024498 A1 Jan. 25, 2024

(30) Foreign Application Priority Data

Sep. 30, 2020 (CN) ........................ 202011061863.1
Sep. 13, 2021 (CN) ........................ 202111069020.0

(51) Int. Cl.

| | |
|---|---|
| ***A61K 47/68*** | (2017.01) |
| ***A61K 9/19*** | (2006.01) |
| ***A61K 31/4375*** | (2006.01) |
| ***A61K 47/26*** | (2006.01) |
| ***A61P 35/00*** | (2006.01) |
| ***C07K 16/28*** | (2006.01) |

(52) U.S. Cl.

CPC ........... *A61K 47/6803* (2017.08); *A61K 9/19* (2013.01); *A61K 31/4375* (2013.01); *A61K 47/26* (2013.01); *A61P 35/00* (2018.01); *C07K 16/28* (2013.01)

(58) Field of Classification Search

CPC ................ A61K 47/6803; A61K 47/26; A61K 47/68037; A61K 47/6849; A61K 47/6859; A61K 9/19; A61K 31/4375; A61K 2039/505; A61P 35/00; C07K 16/28; C07K 16/30; C07K 2317/73; C07K 2317/732; C07K 2317/76; C07K 2317/92

See application file for complete search history.

(56) References Cited

U.S. PATENT DOCUMENTS

| | | | | |
|---|---|---|---|---|
| 8,613,919 | B1 * | 12/2013 | Ma | C07K 16/38 424/130.1 |
| 11,603,407 | B2 * | 3/2023 | Hu | C07K 16/2818 |
| 2005/0238649 | A1 | 10/2005 | Doronina et al. | |
| 2021/0261658 | A1 | 8/2021 | Wu et al. | |

FOREIGN PATENT DOCUMENTS

| | | | |
|---|---|---|---|
| EP | 3725798 | A1 | 10/2020 |
| EP | 3868409 | A1 | 8/2021 |
| EP | 3878863 | A1 | 9/2021 |
| WO | 2016165762 | A1 | 10/2016 |
| WO | 2016166122 | A1 | 10/2016 |
| WO | 2020063676 | A1 | 4/2020 |

OTHER PUBLICATIONS

Salvador E, et al. (2016) Curr Pathobiol Rep. 4:135-145. (DOI 10.1007/s40139-016-0106-6).*
Coati I, et al. (2019) British Journal of Cancer. 121:257-263. (https://doi.org/10.1038/s41416-019-0508-4).*
Sahin U, et al. (Dec. 1, 2008) Clin Cancer Res. 14(23):7624-7634. (doi:10.1158/1078-0432.CCR-08-1547).*
Nakada T, et al. (2016) Bioorganic & Medicinal Chemistry Letters. 26:1542-1545. (http://dx.doi.org/10.1016/j.bmcl.2016.02.020).*
Iwata TN, et al. (Jul. 2018) Mol Cancer Ther. 17(7):1494-1503. (doi: 10.1158/1535-7163.MCT-17-0749).*
Yunxin Cao et al., Claudin-18 Expression in Pancreatic Cancer Cells, Chinese Journal of Cellular and Molecular Immunology, Dec. 2009, vol. 25, No. 12, pp. 1202-1203 (3 pages).
Hua Jiang et al., Claudin18.2-Specific Chimeric Antigen Receptor Engineered T Cells for the Treatment of Gastric Cancer, Journal of National Cancer Institute, 2019, vol. 111, No. 4, pp. 409-419 (10 pages).

* cited by examiner

*Primary Examiner* — Robert S Landsman

(74) *Attorney, Agent, or Firm* — Morgan, Lewis & Bockius LLP

(57) ABSTRACT

Provided are a pharmaceutical composition comprising an antibody-drug conjugate, and use of the pharmaceutical composition. Specifically provided is a pharmaceutical composition, comprising an anti-claudin antibody-drug conjugate.

20 Claims, 4 Drawing Sheets

Specification includes a Sequence Listing.

SEQUENCE LISTING

```
<160> NUMBER OF SEQ ID NOS: 55

<210> SEQ ID NO 1
<211> LENGTH: 261
<212> TYPE: PRT
<213> ORGANISM: Homo sapiens
<220> FEATURE:
<221> NAME/KEY: Region
<222> LOCATION: (1)..(261)
<223> OTHER INFORMATION: Claudin18.2 protein

<400> SEQUENCE: 1

Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260
```

<210> SEQ ID NO 2
<211> LENGTH: 3350
<212> TYPE: DNA
<213> ORGANISM: Homo sapiens
<220> FEATURE:
<221> NAME/KEY: misc_feature
<222> LOCATION: (1)..(3350)
<223> OTHER INFORMATION: Claudin18.2

<400> SEQUENCE: 2

```
agaattgcgc tgtccacttg tcgtgtggct ctgtgtcgac actgtgcgcc accatggccg     60
tgactgcctg tcagggcttg gggttcgtgg tttcactgat tgggattgcg ggcatcattg    120
ctgccacctg catggaccag tggagcaccc aagacttgta caacaacccc gtaacagctg    180
ttttcaacta ccaggggctg tggcgctcct gtgtccgaga gagctctggc ttcaccgagt    240
gccggggcta cttcaccctg ctggggctgc cagccatgct gcaggcagtg cgagccctga    300
tgatcgtagg catcgtcctg ggtgccattg gcctcctggt atccatcttt gccctgaaat    360
gcatccgcat tggcagcatg gaggactctg ccaaagccaa catgacactg acctccggga    420
tcatgttcat tgtctcaggt ctttgtgcaa ttgctggagt gtctgtgttt gccaacatgc    480
tggtgactaa cttctggatg tccacagcta acatgtacac cggcatgggt gggatggtgc    540
agactgttca gaccaggtac acatttggtg cggctctgtt cgtgggctgg gtcgctggag    600
gcctcacact aattgggggt gtgatgatgt gcatcgcctg ccggggcctg gcaccagaag    660
aaaccaacta caaagccgtt tcttatcatg cctcaggcca cagtgttgcc tacaagcctg    720
gaggcttcaa ggccagcact ggctttgggt ccaacaccaa aaacaagaag atatacgatg    780
gaggtgcccg cacagaggac gaggtacaat cttatccttc caagcacgac tatgtgtaat    840
gctctaagac ctctcagcac gggcggaaga aactcccgga gagctcaccc aaaaaacaag    900
gagatcccat ctagatttct tcttgctttt gactcacagc tggaagttag aaaagcctcg    960
atttcatctt tggagaggcc aaatggtctt agcctcagtc tctgtctcta aatattccac   1020
cataaaacag ctgagttatt tatgaattag aggctatagc tcacattttc aatcctctat   1080
ttcttttttt aaatataact ttctactctg atgagagaat gtggttttaa tctctctctc   1140
acattttgat gatttagaca gactccccct cttcctccta gtcaataaac ccattgatga   1200
tctatttccc agcttatccc caagaaaact tttgaaagga aagagtagac ccaaagatgt   1260
tattttctgc tgtttgaatt ttgtctcccc acccccaact tggctagtaa taaacactta   1320
ctgaagaaga agcaataaga gaaagatatt tgtaatctct ccagcccatg atctcggttt   1380
tcttacactg tgatcttaaa agttaccaaa ccaaagtcat tttcagtttg aggcaaccaa   1440
acctttctac tgctgttgac atcttcttat tacagcaaca ccattctagg agtttcctga   1500
gctctccact ggagtcctct ttctgtcgcg ggtcagaaat tgtccctaga tgaatgagaa   1560
aattattttt tttaatttaa gtcctaaata tagttaaaat aaataatgtt ttagtaaaat   1620
gatacactat ctctgtgaaa tagcctcacc cctacatgtg gatagaagga aatgaaaaaa   1680
taattgcttt gacattgtct atatggtact ttgtaaagtc atgcttaagt acaaattcca   1740
tgaaaagctc actgatccta attctttccc tttgaggtct ctatggctct gattgtacat   1800
gatagtaagt gtaagccatg taaaaagtaa ataatgtctg ggcacagtgg ctcacgcctg   1860
taatcctagc actttgggag gctgaggagg aaggatcact tgagcccaga agttcgagac   1920
tagcctgggc aacatggaga agccctgtct ctacaaaata cagagagaaa aaatcagcca   1980
```

```
gtcatggtgg cctacacctg tagtcccagc attccgggag gctgaggtgg gaggatcact   2040

tgagcccagg gaggttgggg ctgcagtgag ccatgatcac accactgcac tccagccagg   2100

tgacatagcg agatcctgtc taaaaaaata aaaaataaat aatggaacac agcaagtcct   2160

aggaagtagg ttaaaactaa ttctttaaaa aaaaaaaaaa gttgagcctg aattaaatgt   2220

aatgtttcca agtgacaggt atccacattt gcatggttac aagccactgc cagttagcag   2280

tagcactttc ctggcactgt ggtcggtttt gttttgtttt gctttgttta gagacggggt   2340

ctcactttcc aggctggcct caaactcctg cactcaagca attcttctac cctggcctcc   2400

caagtagctg gaattacagg tgtgcgccat cacaactagc tggtggtcag ttttgttact   2460

ctgagagctg ttcacttctc tgaattcacc tagagtggtt ggaccatcag atgtttgggc   2520

aaaactgaaa gctctttgca accacacacc ttccctgagc ttacatcact gccctttga    2580

gcagaaagtc taaattcctt ccaagacagt agaattccat cccagtacca aagccagata   2640

ggccccctag gaaactgagg taagagcagt ctctaaaaac tacccacagc agcattggtg   2700

caggggaact tggccattag gttattattt gagaggaaag tcctcacatc aatagtacat   2760

atgaaagtga cctccaaggg gattggtgaa tactcataag gatcttcagg ctgaacagac   2820

tatgtctggg gaaagaacgg attatgcccc attaaataac aagttgtgtt caagagtcag   2880

agcagtgagc tcagaggccc ttctcactga gacagcaaca tttaaaccaa accagaggaa   2940

gtatttgtgg aactcactgc ctcagtttgg gtaaaggatg agcagacaag tcaactaaag   3000

aaaaaagaaa agcaaggagg agggttgagc aatctagagc atggagtttg ttaagtgctc   3060

tctggatttg agttgaagag catccatttg agttgaaggc cacagggcac aatgagctct   3120

cccttctacc accagaaagt ccctggtcag gtctcaggta gtgcggtgtg gctcagctgg   3180

gtttttaatt agcgcattct ctatccaaca tttaattgtt tgaaagcctc catatagtta   3240

gattgtgctt tgtaattttg ttgttgttgc tctatcttat tgtatatgca ttgagtatta   3300

acctgaatgt tttgttactt aaatattaaa aacactgtta tcctacagtt               3350
```

```
<210> SEQ ID NO 3
<211> LENGTH: 120
<212> TYPE: PRT
<213> ORGANISM: Mus musculus
<220> FEATURE:
<221> NAME/KEY: Region
<222> LOCATION: (1)..(120)
<223> OTHER INFORMATION: Heavy chain variable region of mAb1901 murine
      antibody

<400> SEQUENCE: 3

Glu Val Gln Leu Met Glu Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Gly Ile His Trp Val Arg Gln Ala Pro Glu Met Gly Leu Glu Trp Ile
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Gly Tyr Asp Thr Arg Asn Ala Met Asp Tyr Trp Gly Gln
            100                 105                 110
```

```
Gly Thr Ser Val Thr Val Ser Ser
        115                 120


<210> SEQ ID NO 4
<211> LENGTH: 113
<212> TYPE: PRT
<213> ORGANISM: Mus musculus
<220> FEATURE:
<221> NAME/KEY: Region
<222> LOCATION: (1)..(113)
<223> OTHER INFORMATION: Light chain variable region of mAb1901 murine
      antibody

<400> SEQUENCE: 4

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr His Cys Gln Asn
                85                  90                  95

Asp Leu Tyr Tyr Pro Leu Thr Phe Gly Ala Gly Thr Lys Leu Glu Leu
            100                 105                 110

Lys


<210> SEQ ID NO 5
<211> LENGTH: 118
<212> TYPE: PRT
<213> ORGANISM: Mus musculus
<220> FEATURE:
<221> NAME/KEY: Region
<222> LOCATION: (1)..(118)
<223> OTHER INFORMATION: Heavy chain variable region of mAb1902 murine
      antibody

<400> SEQUENCE: 5

Glu Val Gln Leu Gln Glu Ser Gly Ala Glu Leu Val Lys Pro Gly Ala
1               5                   10                  15

Ser Val Lys Leu Ser Cys Lys Ala Ser Gly Tyr Ile Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ser Ser Thr Ala Tyr
65                  70                  75                  80

Met Gln Leu Ser Ser Leu Pro Ser Glu Asp Ser Ala Val Tyr Tyr Cys
                85                  90                  95

Ala Arg Leu Lys Thr Gly Asn Ser Phe Asp Tyr Trp Gly Gln Gly Thr
            100                 105                 110

Thr Leu Thr Val Ser Ser
        115


<210> SEQ ID NO 6
```

<211> LENGTH: 113
<212> TYPE: PRT
<213> ORGANISM: Mus musculus
<220> FEATURE:
<221> NAME/KEY: Region
<222> LOCATION: (1)..(113)
<223> OTHER INFORMATION: Light chain variable region of mAb1902 murine antibody

<400> SEQUENCE: 6

```
Asp Ile Val Leu Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Ala Tyr Thr Tyr Pro Phe Thr Phe Gly Ser Gly Thr Lys Leu Glu Ile
            100                 105                 110

Lys
```

<210> SEQ ID NO 7
<211> LENGTH: 330
<212> TYPE: PRT
<213> ORGANISM: Homo sapiens
<220> FEATURE:
<221> NAME/KEY: Region
<222> LOCATION: (1)..(330)
<223> OTHER INFORMATION: Heavy chain constant region of human IgG1 antibody

<400> SEQUENCE: 7

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

-continued

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 8
<211> LENGTH: 107
<212> TYPE: PRT
<213> ORGANISM: Homo sapiens
<220> FEATURE:
<221> NAME/KEY: Region
<222> LOCATION: (1)..(107)
<223> OTHER INFORMATION: Human-derived antibody kappa light chain
      constant region

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 9
<211> LENGTH: 5
<212> TYPE: PRT
<213> ORGANISM: Artificial Sequence
<220> FEATURE:
<223> OTHER INFORMATION: Synthetic Sequence_mAb1901 HCDR1

<400> SEQUENCE: 9

Asp Tyr Gly Ile His
1               5
```

<210> SEQ ID NO 10
<211> LENGTH: 17
<212> TYPE: PRT
<213> ORGANISM: Artificial Sequence
<220> FEATURE:
<223> OTHER INFORMATION: Synthetic Sequence_mAb1901 HCDR2

<400> SEQUENCE: 10

Tyr Ile Ser Arg Gly Ser Ser Thr Ile Tyr Tyr Ala Asp Thr Val Lys
1               5                   10                  15

Gly

<210> SEQ ID NO 11
<211> LENGTH: 11
<212> TYPE: PRT
<213> ORGANISM: Artificial Sequence
<220> FEATURE:
<223> OTHER INFORMATION: Synthetic Sequence_mAb1901 HCDR3

<400> SEQUENCE: 11

Gly Gly Tyr Asp Thr Arg Asn Ala Met Asp Tyr
1               5                   10

<210> SEQ ID NO 12
<211> LENGTH: 17
<212> TYPE: PRT
<213> ORGANISM: Artificial Sequence
<220> FEATURE:
<223> OTHER INFORMATION: Synthetic Sequence_mAb1901 LCDR1

<400> SEQUENCE: 12

Lys Ser Ser Gln Ser Leu Leu Asn Ser Gly Asn Gln Lys Asn Tyr Leu
1               5                   10                  15

Ala

<210> SEQ ID NO 13
<211> LENGTH: 7
<212> TYPE: PRT
<213> ORGANISM: Artificial Sequence
<220> FEATURE:
<223> OTHER INFORMATION: Synthetic Sequence_mAb1901 LCDR2

<400> SEQUENCE: 13

Gly Ala Ser Thr Arg Ala Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Sequence_mAb1901 LCDR3

<400> SEQUENCE: 14

Gln Asn Asp Leu Tyr Tyr Pro Leu Thr
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Sequence_mAb1902 HCDR1

<400> SEQUENCE: 15

Ser Tyr Trp Met His 1 5

<210> SEQ ID NO 16
<211> LENGTH: 17
<212> TYPE: PRT
<213> ORGANISM: Artificial Sequence
<220> FEATURE:
<223> OTHER INFORMATION: Synthetic Sequence_mAb1902 HCDR2

<400> SEQUENCE: 16

Met Ile His Pro Asn Ser Gly Ser Thr Asn Tyr Asn Glu Lys Phe Lys
1 5 10 15

Gly

<210> SEQ ID NO 17
<211> LENGTH: 9
<212> TYPE: PRT
<213> ORGANISM: Artificial Sequence
<220> FEATURE:
<223> OTHER INFORMATION: Synthetic Sequence_mAb1902 HCDR3

<400> SEQUENCE: 17

Leu Lys Thr Gly Asn Ser Phe Asp Tyr
1 5

<210> SEQ ID NO 18
<211> LENGTH: 17
<212> TYPE: PRT
<213> ORGANISM: Artificial Sequence
<220> FEATURE:
<223> OTHER INFORMATION: Synthetic Sequence_mAb1902 LCDR1

<400> SEQUENCE: 18

Lys Ser Ser Gln Ser Leu Leu Asn Ser Gly Asn Gln Lys Asn Tyr Leu
1 5 10 15

Thr

<210> SEQ ID NO 19
<211> LENGTH: 7
<212> TYPE: PRT
<213> ORGANISM: Artificial Sequence
<220> FEATURE:
<223> OTHER INFORMATION: Synthetic Sequence_mAb1902 LCDR2

<400> SEQUENCE: 19

Trp Ala Ser Thr Arg Glu Ser
1 5

<210> SEQ ID NO 20
<211> LENGTH: 9
<212> TYPE: PRT
<213> ORGANISM: Artificial Sequence
<220> FEATURE:
<223> OTHER INFORMATION: Synthetic Sequence_mAb1902 LCDR3

<400> SEQUENCE: 20

Gln Asn Ala Tyr Thr Tyr Pro Phe Thr
1 5

<210> SEQ ID NO 21
<211> LENGTH: 113
<212> TYPE: PRT
<213> ORGANISM: Artificial Sequence
<220> FEATURE:
<223> OTHER INFORMATION: Synthetic Sequence_VL1

<400> SEQUENCE: 21

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Leu Tyr Tyr Pro Leu Thr Phe Gly Gln Gly Thr Lys Leu Glu Ile
            100                 105                 110

Lys
```

<210> SEQ ID NO 22
<211> LENGTH: 113
<212> TYPE: PRT
<213> ORGANISM: Artificial Sequence
<220> FEATURE:
<223> OTHER INFORMATION: Synthetic Sequence_VL2

<400> SEQUENCE: 22

```
Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Leu Tyr Tyr Pro Leu Thr Phe Gly Gln Gly Thr Lys Leu Glu Ile
            100                 105                 110

Lys
```

<210> SEQ ID NO 23
<211> LENGTH: 113
<212> TYPE: PRT
<213> ORGANISM: Artificial Sequence
<220> FEATURE:
<223> OTHER INFORMATION: Synthetic Sequence_VL3

<400> SEQUENCE: 23

```
Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60
```

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr His Cys Gln Asn
                85                  90                  95

Asp Leu Tyr Tyr Pro Leu Thr Phe Gly Gln Gly Thr Lys Leu Glu Ile
            100                 105                 110

Lys


<210> SEQ ID NO 24
<211> LENGTH: 120
<212> TYPE: PRT
<213> ORGANISM: Artificial Sequence
<220> FEATURE:
<223> OTHER INFORMATION: Synthetic Sequence_VH1

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser
        115                 120


<210> SEQ ID NO 25
<211> LENGTH: 120
<212> TYPE: PRT
<213> ORGANISM: Artificial Sequence
<220> FEATURE:
<223> OTHER INFORMATION: Synthetic Sequence_VH2

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser
        115                 120
```

<210> SEQ ID NO 26
<211> LENGTH: 120
<212> TYPE: PRT
<213> ORGANISM: Artificial Sequence
<220> FEATURE:
<223> OTHER INFORMATION: Synthetic Sequence_VH3

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Ile
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser
        115                 120
```

<210> SEQ ID NO 27
<211> LENGTH: 120
<212> TYPE: PRT
<213> ORGANISM: Artificial Sequence
<220> FEATURE:
<223> OTHER INFORMATION: Synthetic Sequence_VH4

<400> SEQUENCE: 27

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser
        115                 120
```

<210> SEQ ID NO 28
<211> LENGTH: 113
<212> TYPE: PRT
<213> ORGANISM: Artificial Sequence
<220> FEATURE:
<223> OTHER INFORMATION: Synthetic Sequence_VL11

<400> SEQUENCE: 28

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys


<210> SEQ ID NO 29
<211> LENGTH: 113
<212> TYPE: PRT
<213> ORGANISM: Artificial Sequence
<220> FEATURE:
<223> OTHER INFORMATION: Synthetic Sequence_VL12

<400> SEQUENCE: 29

Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys


<210> SEQ ID NO 30
<211> LENGTH: 113
<212> TYPE: PRT
<213> ORGANISM: Artificial Sequence
<220> FEATURE:
<223> OTHER INFORMATION: Synthetic Sequence_VL13

<400> SEQUENCE: 30

Asp Ile Val Leu Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
```

```
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys


<210> SEQ ID NO 31
<211> LENGTH: 118
<212> TYPE: PRT
<213> ORGANISM: Artificial Sequence
<220> FEATURE:
<223> OTHER INFORMATION: Synthetic Sequence_VH11

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Met
        35                  40                  45

Gly Met Ile His Pro Asn Ser Gly Ser Thr Asn Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser
        115


<210> SEQ ID NO 32
<211> LENGTH: 118
<212> TYPE: PRT
<213> ORGANISM: Artificial Sequence
<220> FEATURE:
<223> OTHER INFORMATION: Synthetic Sequence_VH12

<400> SEQUENCE: 32

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Met
        35                  40                  45

Gly Met Ile His Pro Asn Ser Gly Ser Thr Asn Tyr Asn Glu Lys Phe
    50                  55                  60

Lys Gly Arg Val Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser
        115
```

<210> SEQ ID NO 33
<211> LENGTH: 118
<212> TYPE: PRT
<213> ORGANISM: Artificial Sequence
<220> FEATURE:
<223> OTHER INFORMATION: Synthetic Sequence_VH13

<400> SEQUENCE: 33

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser
        115
```

<210> SEQ ID NO 34
<211> LENGTH: 118
<212> TYPE: PRT
<213> ORGANISM: Artificial Sequence
<220> FEATURE:
<223> OTHER INFORMATION: Synthetic Sequence_VH14

<400> SEQUENCE: 34

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Arg Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser
        115
```

<210> SEQ ID NO 35
<211> LENGTH: 450
<212> TYPE: PRT
<213> ORGANISM: Artificial Sequence
<220> FEATURE:
<223> OTHER INFORMATION: Synthetic Sequence_ch1901 heavy chain

<400> SEQUENCE: 35

```
Glu Val Gln Leu Met Glu Ser Gly Gly Gly Leu Val Lys Pro Gly Gly
1               5                   10                  15
```

-continued

```
Ser Leu Lys Leu Ser Cys Ala Ala Ser Gly Phe Thr Phe Ser Asp Tyr
            20                  25                  30

Gly Ile His Trp Val Arg Gln Ala Pro Glu Met Gly Leu Glu Trp Ile
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Gly Gly Tyr Asp Thr Arg Asn Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
        435                 440                 445

Gly Lys
    450


<210> SEQ ID NO 36
<211> LENGTH: 220
<212> TYPE: PRT
<213> ORGANISM: Artificial Sequence
<220> FEATURE:
<223> OTHER INFORMATION: Synthetic Sequence_ch1901 light chain

<400> SEQUENCE: 36

Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr His Cys Gln Asn
                85                  90                  95

Asp Leu Tyr Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 37
<211> LENGTH: 448
<212> TYPE: PRT
<213> ORGANISM: Artificial Sequence
<220> FEATURE:
<223> OTHER INFORMATION: Synthetic Sequence_ch1902 heavy chain

<400> SEQUENCE: 37

Glu Val Gln Leu Gln Glu Ser Gly Ala Glu Leu Val Lys Pro Gly Ala
1               5                   10                  15

Ser Val Lys Leu Ser Cys Lys Ala Ser Gly Tyr Ile Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60
```

```
Lys Gly Lys Ala Thr Leu Thr Leu Asp Lys Ser Ser Ser Thr Ala Tyr
65                  70                  75                  80

Met Gln Leu Ser Ser Leu Pro Ser Glu Asp Ser Ala Val Tyr Tyr Cys
                85                  90                  95

Ala Arg Leu Lys Thr Gly Asn Ser Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 38
<211> LENGTH: 220
<212> TYPE: PRT
<213> ORGANISM: Artificial Sequence
<220> FEATURE:

<223> OTHER INFORMATION: Synthetic Sequence_ch1902 light chain

<400> SEQUENCE: 38

```
Asp Ile Val Leu Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Ile Tyr Tyr Cys Gln Asn
                85                  90                  95

Ala Tyr Thr Tyr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 39
<211> LENGTH: 220
<212> TYPE: PRT
<213> ORGANISM: Artificial Sequence
<220> FEATURE:
<223> OTHER INFORMATION: Synthetic Sequence_L1

<400> SEQUENCE: 39

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Leu Tyr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125
```

```
Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 40
<211> LENGTH: 220
<212> TYPE: PRT
<213> ORGANISM: Artificial Sequence
<220> FEATURE:
<223> OTHER INFORMATION: Synthetic Sequence_L2

<400> SEQUENCE: 40

Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Leu Tyr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 41
<211> LENGTH: 220
<212> TYPE: PRT
<213> ORGANISM: Artificial Sequence
<220> FEATURE:
<223> OTHER INFORMATION: Synthetic Sequence_L3
```

<400> SEQUENCE: 41

```
Asp Ile Val Met Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Ala Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr His Cys Gln Asn
                85                  90                  95

Asp Leu Tyr Tyr Pro Leu Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 42
<211> LENGTH: 450
<212> TYPE: PRT
<213> ORGANISM: Artificial Sequence
<220> FEATURE:
<223> OTHER INFORMATION: Synthetic Sequence_H1

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

```
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 43
<211> LENGTH: 450
<212> TYPE: PRT
<213> ORGANISM: Artificial Sequence
<220> FEATURE:
<223> OTHER INFORMATION: Synthetic Sequence_H2

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
```

-continued

```
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 44
<211> LENGTH: 450
<212> TYPE: PRT
<213> ORGANISM: Artificial Sequence
<220> FEATURE:
<223> OTHER INFORMATION: Synthetic Sequence_H3

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Ile
        35                  40                  45

Ala Tyr Ile Ser Arg Gly Ser Ser Thr Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 45
<211> LENGTH: 450
<212> TYPE: PRT
<213> ORGANISM: Artificial Sequence
<220> FEATURE:
<223> OTHER INFORMATION: Synthetic Sequence_H4

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Gly Ile His Trp Val Arg Gln Ala Pro Gly Lys Gly Leu Glu Trp Val
        35                  40                  45

Ala Tyr Ile Ser Arg Gly Ser Ser Thr Ile Tyr Tyr Ala Asp Thr Val
    50                  55                  60

Lys Gly Arg Phe Thr Met Ser Arg Asp Asn Ala Lys Asn Ser Leu Tyr
65                  70                  75                  80

Leu Gln Met Thr Ser Leu Arg Ala Glu Asp Thr Ala Val Tyr Tyr Cys
                85                  90                  95

Ala Arg Gly Gly Tyr Asp Thr Arg Asn Ala Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

-continued

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly Lys
450

<210> SEQ ID NO 46
<211> LENGTH: 220
<212> TYPE: PRT
<213> ORGANISM: Artificial Sequence
<220> FEATURE:
<223> OTHER INFORMATION: Synthetic Sequence_L11

<400> SEQUENCE: 46

Asp Ile Val Met Thr Gln Ser Pro Asp Ser Leu Ala Val Ser Leu Gly
1 5 10 15

Glu Arg Ala Thr Ile Asn Cys Lys Ser Ser Gln Ser Leu Leu Asn Ser
20 25 30

Gly Asn Gln Lys Asn Tyr Leu Thr Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Asn
85 90 95

Ala Tyr Thr Tyr Pro Phe Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

Gln Ser Gly Asn Ser Gln Glu Ser Val Thr Glu Gln Asp Ser Lys Asp
165 170 175

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 47
<211> LENGTH: 220
<212> TYPE: PRT
<213> ORGANISM: Artificial Sequence
<220> FEATURE:
<223> OTHER INFORMATION: Synthetic Sequence_L12

<400> SEQUENCE: 47

```
Asp Ile Val Leu Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 48
<211> LENGTH: 220
<212> TYPE: PRT
<213> ORGANISM: Artificial Sequence
<220> FEATURE:
<223> OTHER INFORMATION: Synthetic Sequence_L13

<400> SEQUENCE: 48

```
Asp Ile Val Leu Thr Gln Ser Pro Asp Ser Leu Ala Val Ser Leu Gly
1               5                   10                  15

Glu Arg Ala Thr Ile Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
```

```
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Ala Tyr Thr Tyr Pro Phe Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 49
<211> LENGTH: 448
<212> TYPE: PRT
<213> ORGANISM: Artificial Sequence
<220> FEATURE:
<223> OTHER INFORMATION: Synthetic Sequence_H11

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Met
        35                  40                  45

Gly Met Ile His Pro Asn Ser Gly Ser Thr Asn Tyr Asn Glu Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

```
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 50
<211> LENGTH: 448
<212> TYPE: PRT
<213> ORGANISM: Artificial Sequence
<220> FEATURE:
<223> OTHER INFORMATION: Synthetic Sequence_H12

<400> SEQUENCE: 50

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Arg Leu Glu Trp Met
        35                  40                  45

Gly Met Ile His Pro Asn Ser Gly Ser Thr Asn Tyr Asn Glu Lys Phe
    50                  55                  60

Lys Gly Arg Val Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
```

-continued

```
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 51
<211> LENGTH: 448
<212> TYPE: PRT
<213> ORGANISM: Artificial Sequence
<220> FEATURE:
<223> OTHER INFORMATION: Synthetic Sequence_H13

<400> SEQUENCE: 51

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

-continued

```
            20                  25                  30

Trp Met His Trp Val Arg Gln Ala Pro Gly Gln Arg Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 52
<211> LENGTH: 448
<212> TYPE: PRT
<213> ORGANISM: Artificial Sequence
<220> FEATURE:
<223> OTHER INFORMATION: Synthetic Sequence_H14

<400> SEQUENCE: 52

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Arg Leu Glu Trp Ile
        35                  40                  45

Gly Met Ile His Pro Asn Ser Gly Ser Thr Asn Tyr Asn Glu Lys Phe
    50                  55                  60

Lys Gly Lys Ala Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Thr Gly Asn Ser Phe Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365
```

```
Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 53
<211> LENGTH: 448
<212> TYPE: PRT
<213> ORGANISM: Artificial Sequence
<220> FEATURE:
<223> OTHER INFORMATION: Synthetic Sequence_IMAB-362 heavy chain

<400> SEQUENCE: 53

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445


<210> SEQ ID NO 54
<211> LENGTH: 220
<212> TYPE: PRT
<213> ORGANISM: Artificial Sequence
<220> FEATURE:
<223> OTHER INFORMATION: Synthetic Sequence_IMAB-362 light chain

<400> SEQUENCE: 54

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Phe Thr Phe Gly Ser Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205
```

-continued

```
Ser Pro Val Thr Lys Ser Phe Asn Arg Gly Glu Cys
    210                 215                 220


<210> SEQ ID NO 55
<211> LENGTH: 4
<212> TYPE: PRT
<213> ORGANISM: Artificial Sequence
<220> FEATURE:
<223> OTHER INFORMATION: Synthetic Sequence_Tetrapeptide linker

<400> SEQUENCE: 55

Gly Gly Phe Gly
1
```

PHARMACEUTICAL COMPOSITIONS COMPRISING AN ANTI-CLAUDIN 18.2 ANTIBODY-DRUG CONJUGATE AND METHOD OF USE THEREOF TO TREAT A TUMOR OR CANCER

CROSS-REFERENCE TO RELATED APPLICATIONS

The present application is a national stage application of International Patent Application No. PCT/CN2021/122031, filed on Sep. 30, 2021, which claims the benefit of and priority to Chinese Patent Application No. 202011061863.1, filed on Sep. 30, 2020, and Chinese Patent Application No. 202111069020.0, filed on Sep. 13, 2021, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Mar. 17, 2026, is named "721106CPUS_126268-5057-US_Sequence_Listing_V2.txt" and is approximately 95,853 bytes in size.

TECHNICAL FIELD

The present disclosure belongs to the field of pharmaceutical formulations, and in particular relates to a pharmaceutical composition comprising an antibody drug conjugate and use thereof as an anti-cancer medicament.

BACKGROUND

The statements herein merely provide background information related to the present disclosure and may not necessarily constitute the prior art.

Claudin-18 (CLDN18), a protein encoded by the Claudin18 gene in humans, belongs to the cellular tight-junction protein family, and can control the flowing of molecules between layer cells. The Claudin protein comprises four transmembrane regions and two extracellular loops in its structure, with its N-terminus and C-terminus in the cytoplasm.

There are two splice variants of Claudin-18, Claudin 18.1 and Claudin 18.2, which differ in sequence by eight amino acids in the first extracellular loops. Claudin 18.1 and Claudin 18.2 are different in terms of expression distribution. Claudin 18.1 is selectively expressed in normal lung cells, while the expression of Claudin 18.2 is highly restricted in normal cells, but it is frequently ectopically activated and overexpressed in a variety of tumors (gastric cancer, lung cancer, pancreatic cancer, etc.). Claudin18.2 is considered a potential therapeutic target for gastric cancer and other types of cancer, and the discovery of the target also provides a new option for the treatment of gastric cancer.

Antibody drug conjugate (ADC) links a monoclonal antibody or an antibody fragment to a biologically active cytotoxin via a stable chemical linker compound, fully exploiting the binding specificity of the antibody to surface antigens of normal cells and tumor cells and the high-efficiency of the cytotoxin, and also avoiding the former's disadvantage of having a poor therapeutic effect, the latter's disadvantage of having serious toxic side effects, and the like. This means that the antibody drug conjugate can bind to tumor cells more precisely and has a reduced effect on normal cells compared to conventional chemotherapeutic drugs in the past.

At present, some Claudin18.2-targeted antibodies and ADC drugs have been reported in patents such as WO2016166122 and WO2016165762.

ADCs are of more complicated heterostructures than antibodies, and therefore, a greater challenge has been posed to ADC formulations for therapeutic purposes.

SUMMARY

The present disclosure relates to a pharmaceutical formulation containing an anti-Claudin18.2 antibody drug conjugate and use thereof. The formulation has the advantage of having good stability, good lyophilization morphology, etc.

The present disclosure provides a pharmaceutical composition comprising an anti-Claudin 18.2 antibody drug conjugate and a buffer, wherein an anti-Claudin 18.2 antibody in the anti-Claudin18.2 antibody drug conjugate comprises a heavy chain variable region and a light chain variable region, wherein:

i) the heavy chain variable region comprises HCDR1, HCDR2 and HCDR3 having amino acid sequences identical to those of a heavy chain variable region set forth in SEQ ID NO: 5, and the light chain variable region comprises LCDR1, LCDR2 and LCDR3 having amino acid sequences identical to those of a light chain variable region set forth in SEQ ID NO: 6; or ii) the heavy chain variable region comprises HCDR1, HCDR2 and HCDR3 having amino acid sequences identical to those of a heavy chain variable region set forth in SEQ ID NO: 3, and the light chain variable region comprises LCDR1, LCDR2 and LCDR3 having amino acid sequences identical to those of a light chain variable region set forth in SEQ ID NO: 4;

the buffer is a histidine salt buffer.

In some embodiments, in the pharmaceutical composition according to any one of the above, the buffer is a histidine-acetate buffer.

In some embodiments, in the pharmaceutical composition according to any one of the above, the anti-Claudin18.2 antibody comprises a heavy chain variable region and a light chain variable region, wherein:

iii) the heavy chain variable region comprises HCDR1, HCDR2 and HCDR3 set forth in SEQ ID NO: 15, SEQ ID NO: 16 and SEQ ID NO: 17, respectively, and the light chain variable region comprises LCDR1, LCDR2 and LCDR3 set forth in SEQ ID NO: 18, SEQ ID NO: 19 and SEQ ID NO: 20, respectively; or iv) the heavy chain variable region comprises HCDR1, HCDR2 and HCDR3 set forth in SEQ ID NO: 9, SEQ ID NO: 10 and SEQ ID NO: 11, respectively, and the light chain variable region comprises LCDR1, LCDR2 and LCDR3 set forth in SEQ ID NO: 12, SEQ ID NO: 13 and SEQ ID NO: 14, respectively.

In some embodiments, in the pharmaceutical composition according to any one of the above, the anti-Claudin18.2 antibody is a murine antibody, a chimeric antibody or a humanized antibody.

In some embodiments, in the pharmaceutical composition according to any one of the above, the anti-Claudin 18.2 antibody comprises a heavy chain variable region and a light chain variable region, wherein a heavy chain variable region and a light chain variable region are comprised, wherein:

(1) the heavy chain variable region has an amino acid sequence set forth in SEQ ID NO: 3 or having at least 90%, 91%, 92%, 93%, 94%, 95%, 96%, 97%, 98%, 99% or 100% identity thereto, and the light chain variable region has an amino acid sequence set forth in SEQ ID NO: 4 or having at least 90%, 91%, 92%, 93%, 94%, 95%, 96%, 97%, 98%, 99% or 100% identity thereto;

(2) the heavy chain variable region has an amino acid sequence set forth in SEQ ID NO: 24 or having at least 90%, 91%, 92%, 93%, 94%, 95%, 96%, 97%, 98%, 99% or 100% identity thereto, and the light chain variable region has an amino acid sequence set forth in SEQ ID NO: 21 or having at least 90%, 91%, 92%, 93%, 94%, 95%, 96%, 97%, 98%, 99% or 100% identity thereto;

(3) the heavy chain variable region has an amino acid sequence set forth in SEQ ID NO: 5 or having at least 90%, 91%, 92%, 93%, 94%, 95%, 96%, 97%, 98%, 99% or 100% identity thereto, and the light chain variable region has an amino acid sequence set forth in SEQ ID NO: 6 or having at least 90%, 91%, 92%, 93%, 94%, 95%, 96%, 97%, 98%, 99% or 100% identity thereto; or (4) the heavy chain variable region has an amino acid sequence set forth in SEQ ID NO: 31 or having at least 90%, 91%, 92%, 93%, 94%, 95%, 96%, 97%, 98%, 99% or 100% identity thereto, and the light chain variable region has an amino acid sequence set forth in SEQ ID NO: 28 or having at least 90%, 91%, 92%, 93%, 94%, 95%, 96%, 97%, 98%, 99% or 100% identity thereto.

In some embodiments, in the pharmaceutical composition according to any one of the above, the anti-Claudin18.2 antibody is a humanized antibody comprising a framework region derived from a human antibody or a framework region variant thereof, and the framework region variant has reverse mutations of up to 10 amino acids in a light chain framework region and/or a heavy chain framework region of the human antibody.

In some embodiments, in the pharmaceutical composition according to any one of the above, the framework region variant comprises mutations selected from (a) or (b):

(a) one or more amino acid reverse mutations optionally selected from the group consisting of 22S, 85I and 87H, comprised in the light chain variable region; and/or one or more amino acid reverse mutations optionally selected from the group consisting of 48I, 82T and 69M, comprised in the heavy chain variable region; or (b) one or more amino acid reverse mutations optionally selected from the group consisting of 4L and 22S, comprised in the light chain variable region; and/or one or more amino acid reverse mutations optionally selected from the group consisting of 38K, 40R, 48I, 66K, 67A, 69L, 71L and 73K, comprised in the heavy chain variable region.

In some embodiments, in the pharmaceutical composition according to any one of the above, the framework region variant comprises mutations selected from:

(a-1) amino acid reverse mutations 22S, 85I and 87H comprised in the light chain variable region, and amino acid reverse mutations 48I and 82T comprised in the heavy chain variable region; or (b-1) an amino acid reverse mutation 4L comprised in the light chain variable region;

wherein 82 in the 82T of the heavy chain variable region denotes position 82A according to the Kabat scheme.

In some embodiments, in the pharmaceutical composition according to any one of the above, the anti-Claudin18.2 antibody comprises a heavy chain variable region and a light chain variable region as shown in any one of the following:

(vii) the heavy chain variable region is set forth in SEQ ID NO: 3, and the light chain variable region is set forth in SEQ ID NO: 4;

(viii) the heavy chain variable region is set forth in SEQ ID NO: 24, 25, 26 or 27, and the light chain variable region is set forth in SEQ ID NO: 21, 22 or 23;

(ix) the heavy chain variable region is set forth in SEQ ID NO: 5, and the light chain variable region is set forth in SEQ ID NO: 6; or (x) the heavy chain variable region is set forth in SEQ ID NO: 31, 32, 33 or 34, and the light chain variable region is set forth in SEQ ID NO: 28, 29 or 30.

In some embodiments, in the pharmaceutical composition according to any one of the above, the anti-Claudin18.2 antibody comprises a heavy chain variable region and a light chain variable region as shown in any one of the following:

(xi) the heavy chain variable region is set forth in SEQ ID NO: 31, and the light chain variable region is set forth in SEQ ID NO: 29; or (xii) the heavy chain variable region is set forth in SEQ ID NO: 26, and the light chain variable region is set forth in SEQ ID NO: 23.

In some embodiments, in the pharmaceutical composition according to any one of the above, the anti-Claudin18.2 antibody comprises an antibody heavy chain constant region and an antibody light chain constant region.

In some embodiments, the heavy chain constant region is selected from the group consisting of human IgG1, IgG2, IgG3 and IgG4 constant regions and conventional variants thereof, and the light chain constant region is selected from the group consisting of human antibody k and 2 chain constant regions and conventional variants thereof. In some embodiments, the antibody comprises a heavy chain constant region set forth in SEQ ID NO: 7 and a light chain constant region set forth in SEQ ID NO: 8.

In some embodiments, the antibody comprises: a heavy chain having at least 90%, 91%, 92%, 93%, 94%, 95%, 96%, 97%, 98%, 99% or 100% identity to a heavy chain having an amino acid sequence set forth in SEQ ID NO: 35 or 42 and a light chain having at least 90%, 91%, 92%, 93%, 94%, 95%, 96%, 97%, 98%, 99% or 100% identity to a light chain having an amino acid sequence set forth in SEQ ID NO: 36 or 39; or a heavy chain having at least 90%, 91%, 92%, 93%, 94%, 95%, 96%, 97%, 98%, 99% or 100% identity to a heavy chain having an amino acid sequence set forth in SEQ ID NO: 37 or 49 and a light chain having at least 90%, 91%, 92%, 93%, 94%, 95%, 96%, 97%, 98%, 99% or 100% identity to a light chain having an amino acid sequence set forth in SEQ ID NO: 38 or 46.

In some embodiments, in the pharmaceutical composition according to any one of the above, the anti-Claudin18.2 antibody comprises a heavy chain and a light chain as shown in any one of the following:

(c) a heavy chain having a sequence set forth in SEQ ID NO: 35 and a light chain having a sequence set forth in SEQ ID NO: 36;

(d) a heavy chain having a sequence set forth in SEQ ID NO: 42, 43, 44 or 45 and a light chain having a sequence set forth in SEQ ID NO: 39, 40 or 41;

(e) a heavy chain having a sequence set forth in SEQ ID NO: 37 and a light chain having a sequence set forth in SEQ ID NO: 38; or (f) a heavy chain having a sequence set forth in SEQ ID NO: 49, 50, 51 or 52 and a light chain having a sequence set forth in SEQ ID NO: 46, 47 or 48.

In some embodiments, in the pharmaceutical composition according to any one of the above, the anti-Claudin18.2 antibody comprises a heavy chain and a light chain as shown in any one of the following:

a heavy chain set forth in SEQ ID NO: 44 and a light chain set forth in SEQ ID NO: 41; or a heavy chain set forth in SEQ ID NO: 49 and a light chain set forth in SEQ ID NO: 47.

In some embodiments, in the pharmaceutical composition according to any one of the above, the anti-Claudin18.2 antibody drug conjugate has a structure of general formula (Pc-L-Y-D):

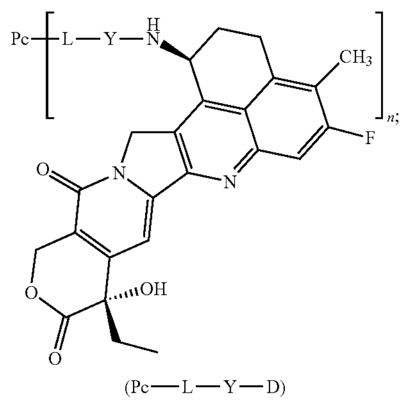

(Pc—L—Y—D)

wherein:

Y is selected from the group consisting of —O—$(CR^aR^b)_m$—$CR^1R^2$—C(O)—, —O—$CR^1R^2$—$(CR^aR^b)_m$—, —O—$CR^1R^2$—, —NH—$(CR^aR^b)_m$—$CR^1R^2$—C(O)— and —S—$(CR^aR^b)_m$—$CR^1R^2$—C(O)—;

$R^a$ and $R^b$ are identical or different and are each independently selected from the group consisting of hydrogen, deuterium, halogen, alkyl, haloalkyl, deuterated alkyl, alkoxy, hydroxy, amino, cyano, nitro, hydroxyalkyl, cycloalkyl and heterocyclyl; or, $R^a$ and $R^b$, together with the carbon atom to which they are attached, form cycloalkyl or heterocyclyl;

$R^1$ is selected from the group consisting of halogen, haloalkyl, deuterated alkyl, cycloalkyl, cycloalkylalkyl, alkoxyalkyl, heterocyclyl, aryl and heteroaryl;

$R^2$ is selected from the group consisting of hydrogen, halogen, haloalkyl, deuterated alkyl, cycloalkyl, cycloalkylalkyl, alkoxyalkyl, heterocyclyl, aryl and heteroaryl;

or, $R^1$ and $R^2$, together with the carbon atom to which they are attached, form cycloalkyl or heterocyclyl;

or, $R^a$ and $R^2$, together with the carbon atom to which they are attached, form cycloalkyl or heterocyclyl;

m is an integer from 0 to 4;

n is a decimal or an integer from 1 to 10;

L is a linker unit;

Pc is an anti-Claudin18.2 antibody.

In some embodiments, in the pharmaceutical composition according to any one of the above, n is a decimal or an integer and can be 2 to 8, 3 to 7, 3.5 to 4.5, 2, 3, 3.5, 4, 4.5, 5, 6, 7, 8 or 9.

In some embodiments, in the pharmaceutical composition according to any one of the above, the anti-Claudin18.2 antibody drug conjugate has a structure of general formula (Pc-L-Y-D), wherein:

Y is —O—$(CR^aR^b)_m$—$CR^1R^2$—C(O)—;

$R^a$ and $R^b$ are identical or different and are each independently selected from the group consisting of hydrogen, deuterium, halogen and $C_{1-6}$ alkyl;

$R^1$ is $C_{1-6}$ haloalkyl or $C_{3-6}$ cycloalkyl;

$R^2$ is selected from the group consisting of hydrogen, $C_{1-6}$ haloalkyl and $C_{3-6}$ cycloalkyl;

or, $R^1$ and $R^2$, together with the carbon atom to which they are attached, form $C_{3-6}$ cycloalkyl;

m is 0 or 1.

In some embodiments, in the pharmaceutical composition according to any one of the above, the anti-Claudin18.2 antibody drug conjugate has a structure of general formula (Pc-L-Y-D), wherein Y is selected from the group consisting of:

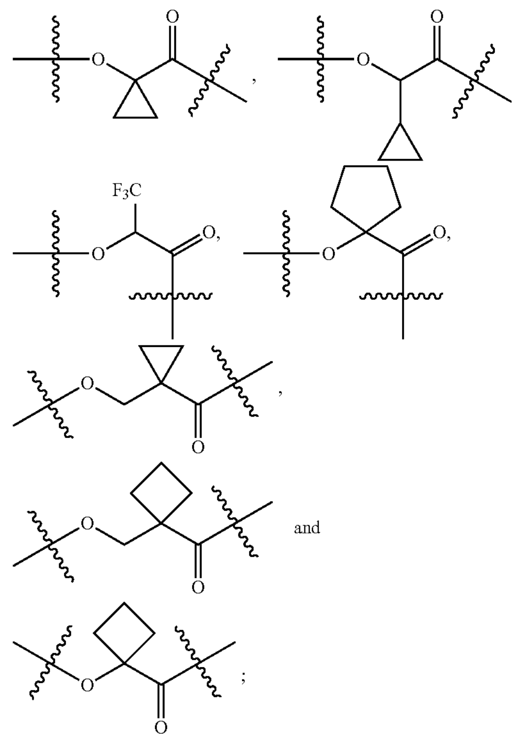

and

;

wherein the O-terminus of Y is connected to the linker unit L.

In some embodiments, in the pharmaceutical composition according to any one of the above, the linker unit -L- is $-L^1-L^2-L^3-L^4-$;

$L^1$ is selected from the group consisting of -(succinimidyl-3-yl-N)—W—C(O)—, —$CH_2$—C(O)—$NR^3$—W—C(O)— and —C(O)—W—C(O)—, wherein W is selected from the group consisting of $C_{1-8}$ alkyl, $C_{1-8}$ alkyl-cycloalkyl and linear heteroalkyl of 1 to 8 chain atoms, and the heteroalkyl comprises 1 to 3 heteroatoms selected from the group consisting of N, O and S, wherein the $C_{1-8}$ alkyl, $C_{1-8}$ alkyl-cycloalkyl or linear heteroalkyl of 1 to 8 chain atoms is each independently optionally further substituted with one or more substituents selected from the group consisting of halogen, hydroxy, cyano, amino, $C_{1-6}$ alkyl, $C_{1-6}$ chloroalkyl, deuterated $C_{1-6}$ alkyl, $C_{1-6}$ alkoxy and $C_{3-6}$ cycloalkyl;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20;

$L^3$ is a peptide residue consisting of 2 to 7 amino acids, wherein the amino acid residues are selected from the group consisting of amino acid residues formed from amino acids from phenylalanine, glycine, valine, lysine, citrulline, serine, glutamic acid and aspartic acid, and are optionally further substituted with one or more substituents selected from the group consisting of halogen, hydroxy, cyano, amino, $C_{1-6}$ alkyl, $C_{1-6}$ chloroalkyl, deuterated $C_{1-6}$ alkyl, $C_{1-6}$ alkoxy and $C_{3-6}$ cycloalkyl;

$L^4$ is selected from the group consisting of —$NR^5(CR^6R^7)_t$—, —$C(O)NR^5$, —$C(O)NR^5(CH_2)_t$— and a chemical bond, wherein t is an integer from 1 to 6;

$R^3$, $R^4$ and $R^5$ are identical or different and are each independently selected from the group consisting of hydrogen, $C_{1-6}$ alkyl, $C_{1-6}$ haloalkyl, deuterated $C_{1-6}$ alkyl and $C_{1-6}$ hydroxyalkyl;

$R^6$ and $R^7$ are identical or different and are each independently selected from the group consisting of hydrogen, halogen, $C_{1-6}$ alkyl, $C_{1-6}$ haloalkyl, deuterated $C_{1-6}$ alkyl and $C_{1-6}$ hydroxyalkyl.

In some embodiments, in the pharmaceutical composition according to any one of the above, the linker unit -L- is -$L^1$-$L^2$-$L^3$-$L^4$-;

$L^1$ is

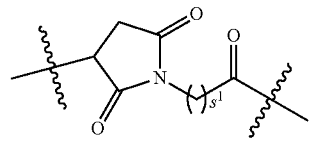

and $s^1$ is an integer from 2 to 8;

$L^2$ is a chemical bond;

$L^3$ is a tetrapeptide residue, preferably a tetrapeptide residue of GGFG (SEQ ID No: 55);

$L^4$ is —$NR^5(CR^6R^7)$t-, wherein $R^5$, $R^6$ and $R^7$ are identical or different and are each independently hydrogen or $C_{1-6}$ alkyl, and t is 1 or 2;

wherein the $L^1$ terminus is connected to Pc, and the $L^4$ terminus is connected to Y.

In some embodiments, in the pharmaceutical composition according to any one of the above, -L- is:

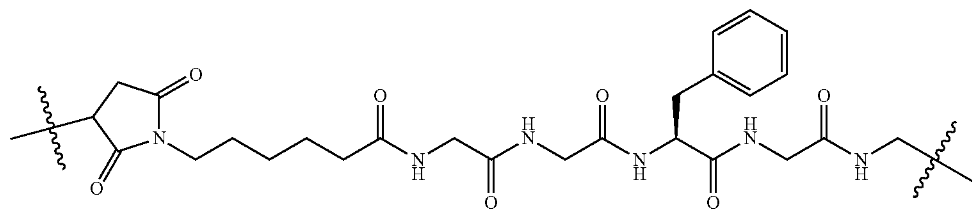

In some embodiments, in the pharmaceutical composition according to any one of the above, L-Y— is optionally selected from the group consisting of:

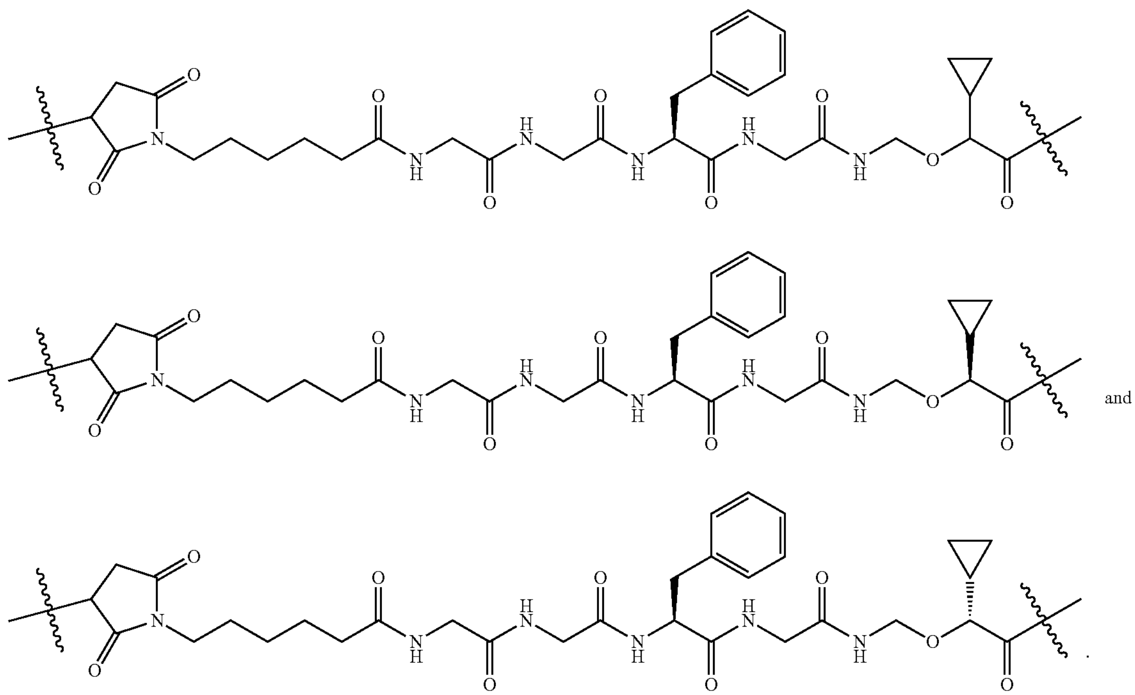 [SMILES: *C(=O)C(OCNC(=O)CNC(=O)[C@H](Cc1ccccc1)NC(=O)CNC(=O)CNC(=O)CCCCCN1C(=O)CC(*)C1=O)C1CC1 ; *C(=O)[C@@H](OCNC(=O)CNC(=O)[C@H](Cc1ccccc1)NC(=O)CNC(=O)CNC(=O)CCCCCN1C(=O)CC(*)C1=O)C1CC1 ; *C(=O)[C@H](OCNC(=O)CNC(=O)[C@H](Cc1ccccc1)NC(=O)CNC(=O)CNC(=O)CCCCCN1C(=O)CC(*)C1=O)C1CC1]

and

In some embodiments, in the pharmaceutical composition according to any one of the above, the anti-Claudin18.2 antibody drug conjugate is selected from any one of the following structures:
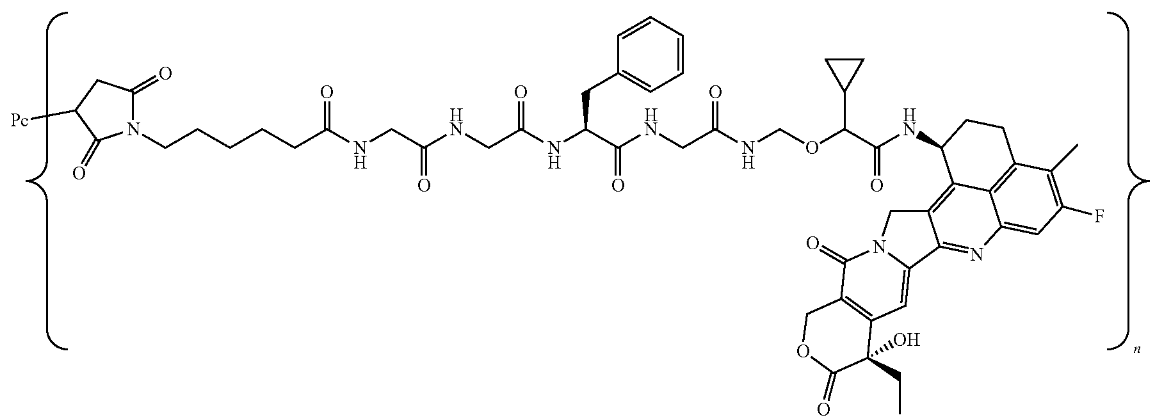
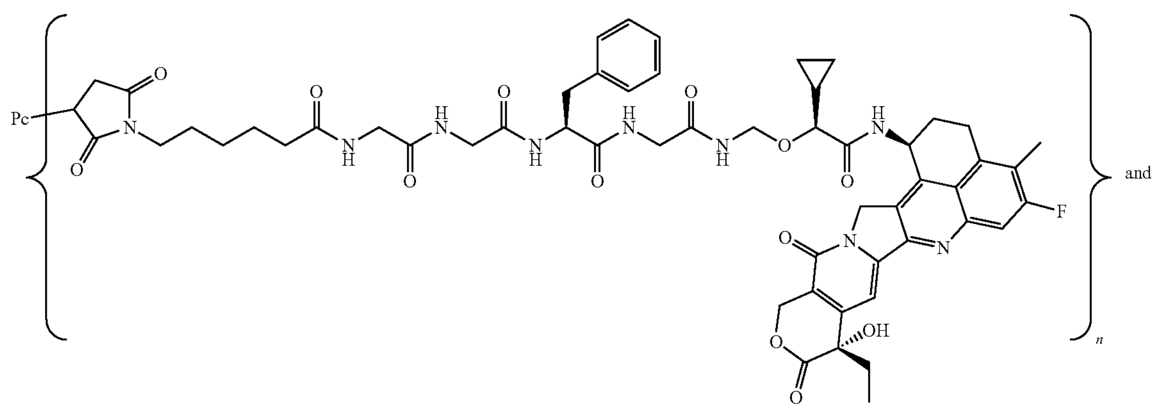
and
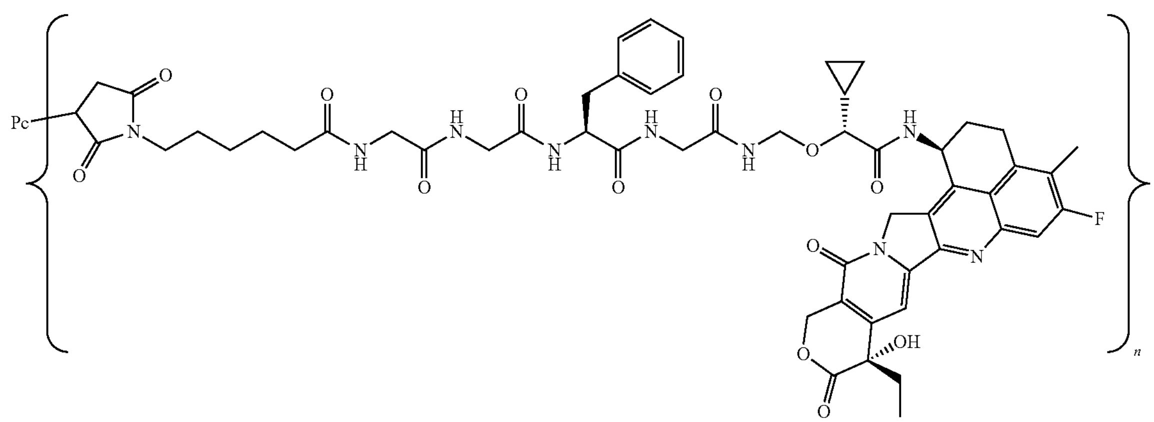
wherein Pc and n are as defined in general formula (Pc-L-Y-D).

In some embodiments, in the pharmaceutical composition according to any one of the above, the anti-Claudin 18.2 antibody drug conjugate has a structure of the formula below:

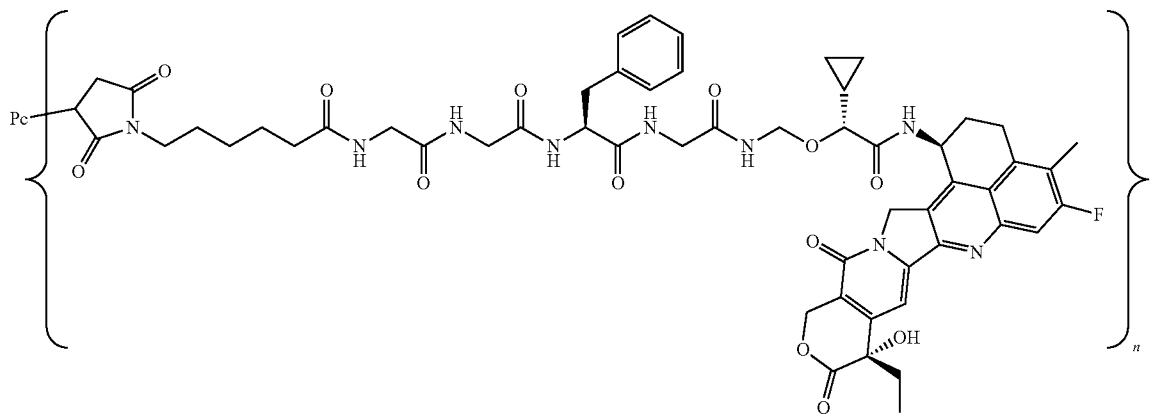

wherein:

n is a decimal or an integer from 2 to 8;

Pc is an anti-Claudin18.2 antibody.

In some embodiments, the pharmaceutical composition according to any one of the above further comprises a surfactant. In some embodiments, the surfactant is selected from the group consisting of polysorbate (such as polysorbate 20 or polysorbate 80), poloxamer, Triton, sodium dodecyl sulfonate, sodium lauryl sulfonate, sodium octyl glycoside, lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauramido propyl-betaine, cocaramide propyl-betaine, linoleinamide propyl-betaine, myristylamide propyl-betaine, palmitamide propyl-betaine, isostearamide propyl-betaine, myristylamide propyl-dimethylamine, palmitamide propyl-dimethylamine, isostearamide propyl-dimethylamine, sodium methyl cocoyl, sodium methyl oleyl taurate, polyethylene glycol, polypropylene glycol, copolymer of ethylene and propylene glycol, and the like.

In some embodiments, the surfactant is a polysorbate. In some embodiments, the surfactant is polysorbate 80 or polysorbate 20. In some embodiments, the surfactant is polysorbate 80.

In some embodiments, in the pharmaceutical composition according to any one of the above, the surfactant is at a concentration of 0.05 mg/mL to 0.5 mg/mL or 0.1 mg/mL to 0.2 mg/mL. In some embodiments, the surfactant is at a concentration of 0.05 mg/mL, 0.1 mg/mL, 0.15 mg/mL, 0.18 mg/mL, 0.19 mg/mL, 0.2 mg/mL, 0.21 mg/mL, 0.22 mg/mL, 0.3 mg/mL, 0.4 mg/mL or 0.5 mg/mL. In some embodiments, the surfactant is at a concentration of 0.2 mg/mL.

In some embodiments, the pharmaceutical composition according to any one of the above further comprises a sugar. In some embodiments, the sugar is selected from the group consisting of general composition $(CH_2O)_n$ and derivatives thereof, including monosaccharides, disaccharides, trisaccharides, polysaccharides, sugar alcohols, reducing sugars, non-reducing sugars, etc. The sugar may be selected from the group consisting of glucose, sucrose, trehalose, lactose, fructose, maltose, dextran, glycerin, erythritol, glycerol, arabitol, sylitol, sorbitol, mannitol, mellibiose, melezitose, raffinose, mannotriose, stachyose, maltose, lactulose, maltulose, glucitol, maltitol, lactitol, iso-maltulose, etc. In some embodiments, the sugar is selected from the group consisting of sucrose, mannitol and trehalose. In some embodiments, the sugar is sucrose.

In some embodiments, in the pharmaceutical composition according to any one of the above, the sugar is at a concentration of 20 mg/mL to 100 mg/mL or 40 mg/mL to 80 mg/mL. In some embodiments, the sugar is at a concentration of 20 mg/mL, 30 mg/mL, 40 mg/mL, 50 mg/mL, 60 mg/mL, 70 mg/mL, 80 mg/mL, 90 mg/mL or 100 mg/mL. In some embodiments, the sugar is at a concentration of 40 mg/mL.

In some embodiments, in the pharmaceutical composition according to any one of the above, the antibody drug conjugate is at a protein (i.e., antibody) concentration of 1 mg/mL to 100 mg/mL or 10 mg/mL to 30 mg/mL. In some embodiments, the antibody drug conjugate is at a protein concentration of 5 mg/mL, 10 mg/mL, 20 mg/mL, 30 mg/mL, 40 mg/mL, 50 mg/mL, 60 mg/mL, 70 mg/mL, 80 mg/mL, 90 mg/mL or 100 mg/mL. In some embodiments, the antibody drug conjugate is at a protein concentration of 20 mg/mL.

In some embodiments, in the pharmaceutical composition according to any one of the above, the buffer is at a concentration of 5 mM to 50 mM or 10 mM to 30 mM. In some embodiments, the buffer is at a concentration of 5 mM, 10 mM, 15 mM, 20 mM, 25 mM, 30 mM, 35 mM, 40 mM, 45 mM or 50 mM. In some embodiments, the buffer is at a concentration of 30 mM.

In some embodiments, the pharmaceutical composition according to any one of the above has a pH of 5.0-6.5 or 5.0-5.5. In some embodiments, the pharmaceutical composition has a pH of 5.0, 5.1, 5.2, 5.3, 5.4, 5.5, 5.6, 5.7, 5.8, 5.9, 6.0, 6.1, 6.2, 6.3, 6.4 or 6.5. In some embodiments, the pharmaceutical composition has a pH of 5.0-5.4. In some embodiments, the pharmaceutical composition has a pH of 5.0-5.3.

In some embodiments, the pharmaceutical composition according to any one of the above comprises the following components:

(a) the anti-Claudin18.2 antibody drug conjugate at a protein concentration of 10 mg/mL to 30 mg/mL, (b) 0.1 mg/mL to 0.2 mg/mL polysorbate, (c) 40 mg/mL to 80 mg/mL sugar, and (d) 10 mM to 30 mM histidine salt buffer; the pharmaceutical composition having a pH of about 5.0-5.5.

In some embodiments, the pharmaceutical composition according to any one of the above comprises the following components:

(a) the anti-Claudin18.2 antibody drug conjugate at a protein concentration of 10 mg/mL to 30 mg/mL, (b) 0.1 mg/mL to 0.2 mg/mL polysorbate 80, (c) 40 mg/mL to 80 mg/mL sucrose, and (d) 10 mM to 30 mM histidine salt buffer; the pharmaceutical composition having a pH of about 5.0-5.5.

In some embodiments, the pharmaceutical composition according to any one of the above comprises the following components:

(a) the anti-Claudin18.2 antibody drug conjugate at a protein concentration of 20 mg/mL, (b) 0.2 mg/mL polysorbate 80, (c) 40 mg/mL sucrose, and (d) 30 mM histidine-acetate buffer; the pharmaceutical composition having a pH of 5.0-5.3.

In some embodiments, in the pharmaceutical composition according to any one of the above, the anti-Claudin 18.2 antibody drug conjugate has a structure of the formula below:

The present disclosure also provides a method for preparing a lyophilized formulation comprising an antibody drug conjugate, which comprises a step of lyophilizing the pharmaceutical composition according to any one of the above.

The present disclosure also provides a lyophilized formulation containing an antibody drug conjugate obtained by lyophilizing the pharmaceutical composition according to any one of the above.

In some embodiments, the lyophilization according to any one of the above comprises steps of pre-freezing, primary drying and secondary drying in sequence.

In some embodiments, the lyophilization procedure is as follows: pre-freezing at a temperature of 5° C.; pre-freezing at a temperature of −45° C.; primary drying at a temperature of −20° C. at a degree of vacuum of 20 Pa; and secondary drying at a temperature of 25° C. at a degree of vacuum of 1 Pa. In some embodiments, the lyophilization procedure is as follows: pre-freezing at a temperature of 5° C. for a period of 10 min; pre-freezing at a temperature of −45° C. for a period of 50 min; primary drying at a temperature of −20° C. at a degree of vacuum of 20 Pa for a period of 120 min; and secondary drying at a temperature of 25° C. at a degree of vacuum of 1 Pa for a period of 60 min.

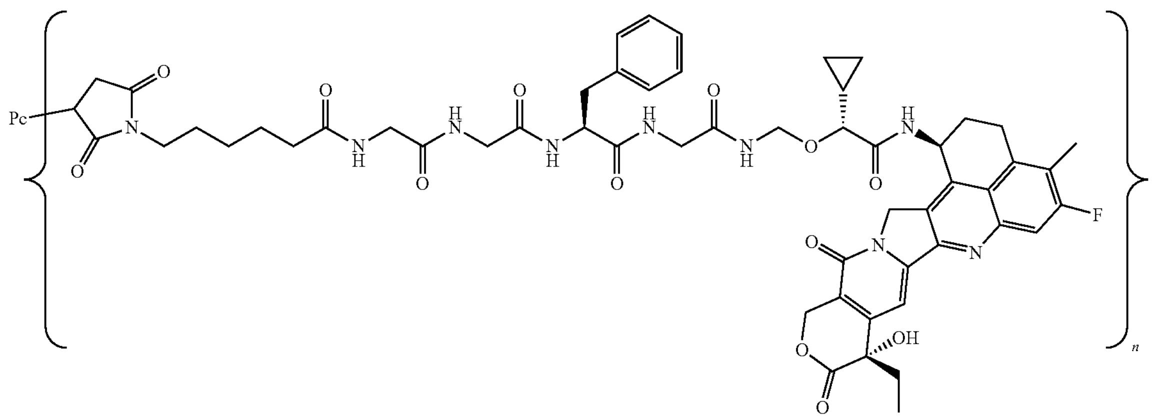

wherein:

n is a decimal or an integer from 2 to 8;

Pc is an anti-Claudin18.2 antibody comprising a heavy chain set forth in SEQ ID NO: 49 and a light chain set forth in SEQ ID NO: 47; the pharmaceutical composition comprises the antibody drug conjugate at a protein concentration of 20 mg/mL;

the pharmaceutical composition further comprises the following components:

0.2 mg/mL polysorbate 80, 40 mg/mL sucrose, and 30 mM histidine-acetate buffer; the pharmaceutical composition having a pH of 5.0-5.3.

In some embodiments, the pharmaceutical composition according to any one of the above is a liquid formulation. In some embodiments, the liquid formulation contains water as solvent.

The present disclosure also provides a lyophilized formulation comprising an antibody drug conjugate, wherein the formulation can be reconstituted to form the pharmaceutical composition according to any one of the above.

The present disclosure also provides a lyophilized formulation that is a lyophilized form of the pharmaceutical composition according to any one of the above.

In some embodiments, the lyophilized formulation is stable at 2-8° C. for at least 3 months, at least 6 months, at least 12 months, at least 18 months, or at least 24 months. In some embodiments, the lyophilized formulation is stable at 40° C. for at least 7 days, at least 14 days, or at least 28 days.

The present disclosure also provides a lyophilized formulation that is a reconstituted form of the lyophilized formulation according to any one of the above.

The present disclosure also provides a reconstituted solution comprising an antibody drug conjugate prepared by reconstituting the lyophilized formulation according to any one of the above.

In some embodiments, the reconstituted solution described above comprises the following components:

(a) the anti-Claudin18.2 antibody drug conjugate at a protein concentration of 10 mg/mL to 30 mg/mL, (b) 0.1 mg/mL to 0.2 mg/mL polysorbate, (c) 40 mg/mL to 80 mg/mL sugar, and (d) 10 mM to 30 mM histidine salt buffer; the reconstituted solution having a pH of about 5.0-5.5.

In some embodiments, the reconstituted solution described above comprises the following components:

(a) the anti-Claudin18.2 antibody drug conjugate at a protein concentration of 10 mg/mL to 30 mg/mL, (b) 0.1 mg/mL to 0.2 mg/mL polysorbate 80, (c) 40 mg/mL to 80 mg/mL sucrose, and (d) 10 mM to 30 mM histidine salt buffer; the reconstituted solution having a pH of about 5.0-5.5.

In some embodiments, the reconstituted solution described above comprises the following components:

(a) the anti-Claudin18.2 antibody drug conjugate at a protein concentration of 20 mg/mL, (b) 0.2 mg/mL polysorbate 80, (c) 40 mg/mL sucrose, and (d) 30 mM histidine-acetate buffer; the reconstituted solution having a pH of 5.0-5.3.

The present disclosure also provides an article of manufacture comprising a container containing the pharmaceutical composition according to any one of the above, the lyophilized formulation according to any one of the above, or the reconstituted solution according to any one of the above.

The present disclosure also provides a method for treating a tumor or cancer comprising administering to a subject an effective amount of the pharmaceutical composition according to any one of the above, the lyophilized formulation according to any one of the above, the reconstituted solution according to any one of the above, or the article of manufacture according to any one of the above.

In some embodiments, the present disclosure also provides use of the pharmaceutical composition according to any one of the above, the lyophilized formulation according to any one of the above, the reconstituted solution according to any one of the above, or the article of manufacture according to any one of the above, in preparing a medicament for treating a tumor or cancer.

In some embodiments, the present disclosure also provides the pharmaceutical composition according to any one of the above, the lyophilized formulation according to any one of the above, the reconstituted solution according to any one of the above, or the article of manufacture according to any one of the above, for use as a medicament.

In some embodiments, the tumor or cancer is preferably head and neck squamous cell carcinoma, head and neck cancer, brain cancer, neuroglioma, glioblastoma multiforme, neuroblastoma, central nervous system carcinoma, neuroendocrine tumor, throat cancer, nasopharyngeal cancer, esophageal cancer, thyroid cancer, malignant pleural mesothelioma, lung cancer, breast cancer, liver cancer, hepatoma, hepatocellular carcinoma, hepatobiliary cancer, pancreatic cancer, gastric cancer, gastrointestinal cancer, intestinal cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, leukemia, lymphoma, bone cancer, chondrosarcoma, myeloma, multiple myeloma, myelodysplastic syndrome, Krukenberg tumor, myeloproliferative tumor, squamous cell carcinoma, Ewing's sarcoma, systemic light chain amyloidosis and Merkel cell carcinoma.

In some embodiments, the lymphoma is selected from the group consisting of Hodgkin lymphoma, non-Hodgkin lymphoma, diffuse large B-cell lymphoma, follicular lymphoma, primary mediastinal large B-cell lymphoma, mantle cell lymphoma, small lymphocytic lymphoma, large B-cell lymphoma rich in T-cells/histiocytes and lymphoplasmacytic lymphoma.

In some embodiments, the lung cancer is selected from the group consisting of non-small cell lung cancer and small cell lung cancer.

In some embodiments, the leukemia is selected from the group consisting of chronic myeloid leukemia, acute myeloid leukemia, lymphocytic leukemia, lymphoblastic leukemia, acute lymphoblastic leukemia, chronic lymphocytic leukemia and myeloid cell leukemia.

BRIEF DESCRIPTION OF THE DRAWINGS

FIG. 3A shows assays for the ADCC effects of antibodies in wild-type NUGC4 cells (expressing Claudin18.2 at low levels);

FIG. 3B shows assays for the ADCC effects of antibodies in NUGC4 cells expressing Claudin 18.2 at moderate levels; FIG. 3C shows assays for the ADCC effects of antibodies in NUGC4 cells expressing Claudin 18.2 at high levels.

DETAILED DESCRIPTION

Terminology

Figure 1:
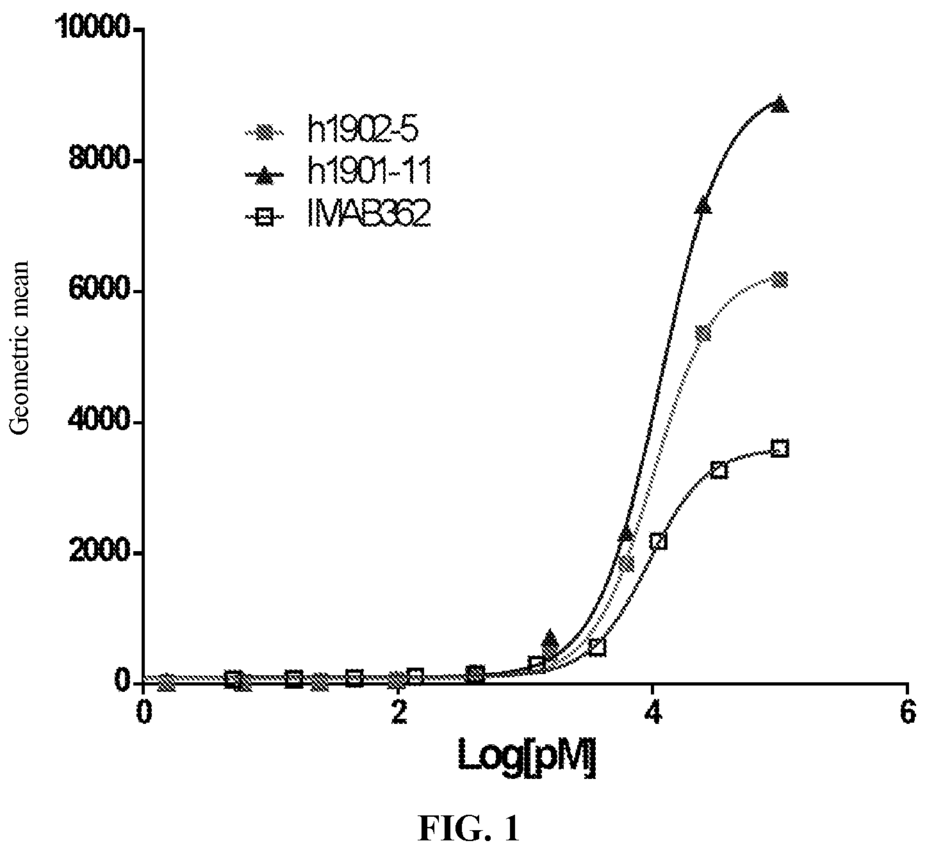
FIG. 1: the results of FACS analysis of the binding of humanized antibodies to human Claudin18.2 at the cellular level.

In order to facilitate the understanding of the present disclosure, some technical and scientific terms are specifically defined below. Unless otherwise specifically defined herein, all other technical and scientific terms used herein have the meanings generally understood by those of ordinary skill in the art to which the present disclosure belongs.

"Antibody drug conjugate (ADC)" is formed by connecting an antibody or an antibody fragment with cytotoxin with biological activity or a small-molecule drug with cell killing activity by a stable chemical linker compound, in which case the binding specificity of the antibody to tumor cell-specific or highly expressed antigens and the high-efficiency of the cytotoxin are fully exploited, and toxic side effects on normal cells are avoided. The antibody drug conjugate can bind to tumor cells precisely and has a reduced effect on normal cells compared to conventional chemotherapeutic drugs in the past.

"Buffer" refers to a buffer that resists changes in pH by the action of its acid-base conjugate components. Examples of buffers that control the pH in an appropriate range include acetate, succinate, gluconate, histidine salt, oxalate, lactate, phosphate, citrate, tartrate, fumarate, glycylglycine and other organic acid buffers.

"Histidine salt buffer" is a buffer comprising histidine ions. Examples of histidine salt buffers include buffers such as histidine-hydrochloride, histidine-acetate, histidine-phosphate and histidine-sulfate; histidine-acetate buffer is preferred. The histidine-acetate buffer is prepared with histidine and acetic acid, and the histidine-hydrochloride buffer is prepared with histidine and hydrochloric acid.

"Citrate buffer" is a buffer comprising citrate ions. Examples of citrate buffers include citric acid-sodium citrate, citric acid-potassium citrate, citric acid-calcium citrate, citric acid-magnesium citrate, and the like. The preferred citrate buffer is citric acid-sodium citrate.

"Succinate buffer" is a buffer comprising succinate ions. Examples of succinate buffers include succinic acid-sodium succinate, succinic acid-potassium succinate, succinic acid-calcium succinate, and the like. The preferred succinate buffer is succinic acid-sodium succinate. Illustratively, the succinic acid-sodium succinate may be prepared from succinic acid and sodium hydroxide, or from succinic acid and sodium succinate.

"Phosphate buffer" is a buffer comprising phosphate ions. Examples of phosphate buffers include disodium hydrogen phosphate-sodium dihydrogen phosphate, disodium hydrogen phosphate-potassium dihydrogen phosphate, disodium hydrogen phosphate-citric acid, and the like. The preferred phosphate buffer is disodium hydrogen phosphate-sodium dihydrogen phosphate.

"Acetate buffer" is a buffer comprising acetate ions. Examples of acetate buffers include acetic acid-sodium acetate, acetic acid histidine salt, acetic acid-potassium acetate, acetic acid-calcium acetate, acetic acid-magnesium acetate, and the like. The preferred acetate buffer is acetic acid-sodium acetate.

"Pharmaceutical composition" refers to a mixture containing one or more of the antibody drug conjugates described herein or physiologically/pharmaceutically acceptable salts or prodrugs thereof, and other chemical components, and the other components are, for example, physiologically/pharmaceutically acceptable carriers and excipients. The purpose of the pharmaceutical composition is to maintain the stability of the active ingredient and promote the administration to an organism, which facilitates the absorption of the active ingredient, thereby exerting biological activity.

As used herein, "pharmaceutical composition" and "formulation" are not mutually exclusive.

Unless otherwise stated, the solvent in the pharmaceutical composition described herein in solution form is water.

"Lyophilized formulation" refers to a formulation or a pharmaceutical composition obtained by freeze-drying a pharmaceutical composition or a formulation in liquid or solution form in vacuum.

While the present disclosure provides content ranges or values, those of ordinary skill in the art will appreciate that the content ranges or values encompass acceptable error ranges for the particular values determined.

The pharmaceutical composition of the present disclosure can achieve a stable effect: a pharmaceutical composition in which the antibody drug conjugate substantially retains its physical and/or chemical stability and/or biological activity after storage; preferably, the pharmaceutical composition substantially retains its physical and chemical stability as well as its biological activity after storage. The storage period is generally selected based on a predetermined shelf life of the pharmaceutical composition. There are a variety of analytical techniques currently available for determining protein stability, and the stability after storage for a selected period of time at a selected temperature can be determined.

A stable formulation is one in which no significant change is observed under the following conditions: stored at refrigeration temperature (2-8° C.) for at least 3 months, preferably 6 months, more preferably 1 year, and even more preferably up to 2 years. In addition, stable liquid formulations include liquid formulations that exhibit desirable features after storage at temperatures including 25° C. for periods including 1 month, 3 months and 6 months. Typical examples for stability are as follows: typically, no more than about 10%, preferably no more than about 5%, of antibody monomers aggregate or are degraded as measured by SEC-HPLC. The formulation is a pale yellow, nearly colorless and clear liquid, or colorless, or clear to slightly opalescent, by visual analysis. The concentration, pH and osmolality of the formulation have no more than ±10% change. Typically, no more than about 10%, preferably no more than about 5%, of decrease is observed. Typically, no more than about 10%, preferably no more than about 5%, of aggregation is formed.

An antibody drug conjugate "retains its physical stability" in a pharmaceutical formulation if it shows no significant increase in aggregation, precipitation and/or denaturation upon visual examination of color and/or clarity, or as measured by UV light scattering, size exclusion chromatography (SEC) and dynamic light scattering (DLS). Changes in protein conformation can be assessed by fluorescence spectroscopy (which determines the protein tertiary structure) and by FTIR spectroscopy (which determines the protein secondary structure).

An antibody drug conjugate "retains its chemical stability" in a pharmaceutical formulation if it shows no significant chemical change. Chemical stability can be assessed by detecting and quantifying chemically changed forms of the protein. Degradation processes that often change the chemical structure of proteins include hydrolysis or clipping (evaluated by methods such as size exclusion chromatography and CE-SDS), oxidation (evaluated by methods such as peptide mapping in conjunction with mass spectroscopy or MALDI/TOF/MS), deamidation (evaluated by methods such as ion-exchange chromatography, capillary isoelectric focusing, peptide mapping, and isoaspartic acid measurement), and isomerization (evaluated by measuring the isoaspartic acid content, peptide mapping, etc.).

An antibody drug conjugate "retains its biological activity" in a pharmaceutical formulation if the biological activity of the antibody drug conjugate at a given time is within a predetermined range of the biological activity exhibited at the time the pharmaceutical formulation was prepared.

The three-letter and single-letter codes for amino acids used in the present disclosure are as described in J. Biol. Chem., 243, p3558 (1968).

The term "antibody" herein is used in the broadest sense and encompasses a variety of antibody structures, including but not limited to monoclonal antibodies, polyclonal antibodies, multispecific antibodies (e.g., bispecific antibodies), full-length antibodies or antigen-binding fragments thereof (also known as antigen-binding moieties) so long as they exhibit the desired antigen-binding activity. A full-length antibody is an immunoglobulin (Ig) that comprises at least two heavy chains and two light chains interconnected by disulfide bonds. The heavy chain constant regions of immunoglobulins differ in their amino acid composition and arrangement, and thus in their antigenicity. Accordingly, immunoglobulins can be divided into five classes, otherwise called isotypes of immunoglobulins, namely IgM, IgD, IgG, IgA and IgE, with their corresponding heavy chains being μ chain, δ chain, γ chain, α chain and ε chain, respectively. Ig of the same class can be divided into different subclasses according to differences in the amino acid composition of the hinge regions and the number and positions of disulfide bonds of the heavy chains; for example, IgG can be divided into IgG1, IgG2, IgG3 and IgG4. Light chains are classified into κ or λ chains according to differences in the constant regions. Each of the five classes of Ig may have a κ chain or λ chain.

In the heavy and light chains of the full-length antibody, the sequences of about 110 amino acids near the N-terminus vary considerably and thus are referred to as variable regions (abbreviated as Fv regions); the remaining amino acid sequences near the C-terminus are relatively stable and thus are referred to as constant regions. Each heavy chain consists of a heavy chain variable region (abbreviated as VH) and a heavy chain constant region (abbreviated as CH). The heavy chain constant region comprises three regions (domains), i.e., CH1, CH2 and CH3. Each light chain consists of a light chain variable region (abbreviated as VL) and a light chain constant region (abbreviated as CL). The heavy chain variable region and the light chain variable region comprise hypervariable regions (also referred to as complementarity determining regions, abbreviated as CDRs or HVRs) and framework regions (abbreviated as FRs) whose sequences are relatively conserved. Each VL and VH consist of 3 CDRs and 4 FRs arranged from the amino terminus to the carboxyl terminus in the following order: FR1-CDR1-FR2-CDR2-FR3-CDR3-FR4. The 3 CDRs of the light chain refer to LCDR1, LCDR2 and LCDR3, and the 3 CDRs of the heavy chain refer to HCDR1, HCDR2 and HCDR3.

The "conventional variant" of the human antibody heavy chain constant region and the human antibody light chain constant region described herein refers to a variant of the heavy chain constant region or light chain constant region derived from humans that has been disclosed in the prior art and does not change the structure and function of the antibody variable region. Exemplary variants include IgG1, IgG2, IgG3 or IgG4 heavy chain constant region variants with site-directed modifications and amino acid substitutions in the heavy chain constant region. Specific substitutions are, for example, YTE mutation, L234A and/or L235A mutation, or S228P mutation, 265A (e.g., D265A) and/or 297A (e.g., N297A), and/or mutations to obtain a knob-into-hole structure (so that the antibody heavy chain has a combination of knob-Fc and hole-Fc) known in the art. These mutations have been confirmed to make the antibody have new properties, but do not change the function of the antibody variable region.

The term "antigen-binding fragment" or "functional fragment" or "antigen-binding moiety" refers to one or more fragments of an intact antibody that retain the ability to specifically bind to an antigen. It is shown that a fragment of a full-length antibody can be used to perform the antigen-binding function of the antibody. Illustratively, examples of the binding fragment included in the term "antigen-binding fragment" include (i) a Fab fragment, a monovalent fragment consisting of VL, VH, CL and CH1 domains; (ii) an $F(ab')_2$ fragment, a bivalent fragment comprising two Fab fragments linked by a disulfide bridge in the hinge region; (iii) an Fd fragment, consisting of VH and CH1 domains; (iv) an Fv fragment, consisting of VH and VL domains of one arm of the antibody; (V) a dsFv, a stable antigen-binding fragment formed by VH and VL via interchain disulfide bonds therebetween; (vi) a diabody, a bispecific antibody and a multi-specific antibody, comprising such fragments as an scFv, a dsFv and a Fab. Furthermore, although the two domains of the Fv fragment, VL and VH, are encoded by separate genes, these two domains can be linked by a recombinant method using an artificial peptide linker that enables them to be formed as a single protein chain, wherein the VL and VH pair to form a monovalent molecule, referred to as single-chain Fv (scFv) (see, e.g., Bird et al. (1988) Science 242:423-426; and Huston et al. (1988) Proc. Natl. Acad. Sci USA 85:5879-5883). Such single-chain antibodies are also included in the term "antigen-binding fragment" of an antibody. Such antibody fragments are obtained by conventional techniques known to those skilled in the art, and screened for utility in the same manner as for intact antibodies. Antigen-binding moieties may be produced by a recombinant DNA technique or by enzymatic or chemical cleavage of intact immunoglobulins.

The term "amino acid difference" or "amino acid mutation" refers to the presence of amino acid changes or mutations in the variant protein or polypeptide compared with the original protein or polypeptide, including occurrence of 1, 2, 3 or more amino acid insertions, deletions or substitutions on the basis of the original protein or polypeptide.

The term "antibody framework" or "FR" refers to a portion of a variable domain VL or VH, which serves as a framework for the antigen-binding loops (CDRs) of the variable domain. It is essentially a variable domain without CDRs.

The term "complementarity-determining region", "CDR" or "hypervariable region" refers to one of the 6 hypervariable regions within the variable domain of an antibody which primarily contribute to antigen binding. Generally, there are three CDRs (HCDR1, HCDR2 and HCDR3) in each heavy chain variable region and three CDRs (LCDR1, LCDR2 and LCDR3) in each light chain variable region. The amino acid sequence boundaries of the CDRs can be determined using any one of a variety of well-known schemes, including the "Kabat" numbering scheme (see Kabat et al. (1991), "Sequences of Proteins of Immunological Interest", 5th edition, Public Health Service, National Institutes of Health, Bethesda, MD), the "Chothia" numbering scheme (see Al-Lazikani et al. (1997) JMB 273: 927-948) and the ImMunoGenTics (IMGT) numbering scheme (see Lefranc M. P., Immunologist, 7, 132-136 (1999); Lefranc, M. P. et al., Dev. Comp. Immunol., 27, 55-77 (2003)), and the like. For example, for the classical format, according to the Kabat scheme, the CDR amino acid residues in the heavy chain variable domain (VH) are numbered 31-35 (HCDR1), 50-65 (HCDR2) and 95-102 (HCDR3); the CDR amino acid residues in the light chain variable domain (VL) are numbered 24-34 (LCDR1), 50-56 (LCDR2) and 89-97 (LCDR3). According to the Chothia scheme, the CDR amino acids in VH are numbered 26-32 (HCDR1), 52-56 (HCDR2) and 95-102 (HCDR3); and amino acid residues in VL are numbered 26-32 (LCDR1), 50-52 (LCDR2) and 91-96 (LCDR3). According to the CDR definitions by combining both the Kabat scheme and the Chothia scheme, the CDR is composed of amino acid residues 26-35 (HCDR1), 50-65 (HCDR2) and 95-102 (HCDR3) in the human VH and amino acid residues 24-34 (LCDR1), 50-56 (LCDR2) and 89-97 (LCDR3) in the human VL. According to the IMGT scheme, the CDR amino acid residues in VH are roughly numbered 26-35 (CDR1), 51-57 (CDR2) and 93-102 (CDR3), and the CDR amino acid residues in VL are roughly numbered 27-32 (CDR1), 50-52 (CDR2) and 89-97 (CDR3). According to the IMGT scheme, the CDRs of the antibody can be determined using the program IMGT/DomainGap Align. According to the AbM scheme, the CDR amino acids in VH are numbered 26-32 (HCDR1), 50-58 (HCDR2) and 95-102 (HCDR3); and amino acid residues in VL are numbered 24-34 (LCDR1), 50-56 (LCDR2) and 89-97 (LCDR3). The heavy variable region and light chain variable region of the antibody of the present disclosure as well as its CDRs conform to the Kabat numbering scheme.

The amino acid sequence "identity" refers to the percentage of identical amino acid residues in a first sequence and a second sequence when amino acid sequences are aligned (gaps, when necessary, are allowed to be introduced to achieve maximum percent sequence identity); conservative substitutions are not considered part of the sequence identity. To determine percent amino acid sequence identity, alignments can be achieved in a variety of ways that are within the skill in the art, for example, using publicly available computer software such as BLAST, BLAST-2, ALIGN, ALIGN-2 or Megalign (DNASTAR) software. Those skilled in the art can determine parameters suitable for measuring alignment, including any algorithms required to achieve maximum alignment of the full length of the aligned sequences.

The engineered antibody or antigen-binding fragment of the present disclosure can be prepared and purified by conventional methods. For example, cDNA sequences encoding the heavy and light chains can be cloned and recombined into a GS expression vector. Recombinant immunoglobulin expression vectors can be stably transfected into CHO cells. As a more recommended prior art, mammalian expression systems may result in glycosylation of antibodies, particularly at the highly conserved N-terminal site of the Fc region. Stable clones are obtained by expression of antibodies that bind to the antigen. Positive clones are expanded in a serum-free medium of a bioreactor to produce antibodies. The culture with the secreted antibody can be purified by conventional techniques. For example, purification is performed using an A or G Sepharose FF column containing an adjusted buffer. Non-specifically bound fractions are washed away. The bound antibody is eluted by the pH gradient method, and the antibody fragments are detected by SDS-PAGE and collected. The antibody can be filtered and concentrated by conventional methods. Soluble mixtures and polymers can also be removed by conventional methods, such as molecular sieves and ion exchange. The resulting product needs to be immediately frozen, e.g., at −70° C., or lyophilized.

"Conservative modification" or "conservative replacement or substitution" refers to replacement of amino acids in a protein with other amino acids having similar characteristics (e.g., charge, side-chain size hydrophobicity/hydrophilicity, or backbone conformation and rigidity), so that changes can be frequently made without changing the biological activity of the protein. Those skilled in the art know that, generally speaking, a single amino acid replacement in a non-essential region of a polypeptide does not substantially change the biological activity (see, e.g., Watson et al. (1987) Molecular Biology of the Gene, The Benjamin/Cummings Pub, Co., p224, (4th edition)). In addition, the replacement of amino acids with similar structure or function is unlikely to disrupt the biological activity. Exemplary conservative substitutions are as follows:

TABLE a

Amino acid conservative substitutions

| Original residue | Conservative substitution |
|---|---|
| Ala (A) | Gly; Ser |
| Arg (R) | Lys; His |
| Asn (N) | Gln; His; Asp |
| Asp (D) | Glu; Asn |
| Cys (C) | Ser; Ala; Val |
| Gln (Q) | Asn; Glu |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |

TABLE a-continued

Amino acid conservative substitutions

| Original residue | Conservative substitution |
|---|---|
| Thr (T) | Ser |
| Trp (W) | Tyr; Phe |
| Tyr (Y) | Trp; Phe |
| Val (V) | Ile; Leu |

The term "naked antibody" refers to an antibody that is not conjugated to a heterologous moiety (e.g., a cytotoxic moiety) or a radioactive label. In the present disclosure, the antibody drug conjugate content is expressed in terms of the concentration of the protein, that is, in terms of the weight/volume of the protein (the antibody portion) in the conjugate.

The term "linker unit" or "linker" refers to a chemical structural fragment or bond that is linked at one end to an antibody or an antigen-binding fragment thereof and at the other end to a drug or that is linked to other linkers before being linked to the drug. In preferred embodiments of the present disclosure, they are indicated as L and $L^1$ through $L^4$, wherein the $L^1$ end is linked to an antibody, and the $L^4$ end is linked to a structure unit Y and then to a compound or toxin. The linker includes a stretcher unit, a spacer unit and an amino acid unit, and may be synthesized by methods known in the art, such as those described in US2005-0238649A1. The linker may be a "cleavable linker" favoring the release of drugs in cells. For example, acid-labile linkers (e.g., hydrazones), protease-sensitive (e.g., peptidase-sensitive) linkers, photolabile linkers, dimethyl linkers or disulfide-containing linkers can be used (Chari et al., Cancer Research, 52: 127-131(1992); U.S. Pat. No. 5,208,020).

The term "alkyl" refers to a saturated aliphatic hydrocarbon group that is a linear or branched group containing 1 to 20 carbon atoms, preferably alkyl containing 1 to 12 carbon atoms, more preferably alkyl containing 1 to 10 carbon atoms, and most preferably alkyl containing 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof, and the like. More preferred is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl may be substituted or unsubstituted. When substituted, the substituent may be substituted at any accessible connection site, and the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "heteroalkyl" refers to alkyl containing one or more heteroatoms selected from the group consisting of N, O and S, wherein the alkyl is as defined above.

The term "alkylene" refers to a saturated linear or branched aliphatic hydrocarbon group having two residues derived from the parent alkane by removal of two hydrogen atoms from the same carbon atom or two different carbon atoms. Alkylene is a linear or branched group containing 1 to 20 carbon atoms, preferably 1 to 12 carbon atoms, and more preferably 1 to 6 carbon atoms. Non-limiting examples of alkylene include, but are not limited to, methylene($-CH_2-$), 1,1-ethylidene($-CH(CH_3)-$), 1,2-ethylidene($-CH_2CH_2$)—, 1,1-propylidene($-CH(CH_2CH_3)-$), 1,2-propylidene($-CH_2CH(CH_3)-$), 1,3-propylidene($-CH_2CH_2CH_2-$), 1,4-butylidene($-CH_2CH_2CH_2CH_2-$), 1,5-butylidene($-CH_2CH_2CH_2CH_2CH_2-$), etc. The alkylene may be substituted or unsubstituted. When substituted, the substituent may be substituted at any accessible connection site, and the substituent is preferably substituted with one or more substituents independently optionally selected from the group consisting of alkyl, alkenyl, alkynyl, alkoxy, alkylthio, alkylamino, halogen, sulfhydryl, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkoxy" refers to —O-(alkyl) and —O-(unsubstituted cycloalkyl), wherein the alkyl or cycloalkyl is as defined above. Non-limiting examples of alkoxy include: methoxy, ethoxy, propoxy, butoxy, cyclopropyloxy, cyclobutoxy, cyclopentyloxy and cyclohexyloxy. The alkoxy may be optionally substituted or unsubstituted, and when it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio and heterocycloalkylthio.

The term "cycloalkyl" refers to a saturated or partially unsaturated monocyclic or polycyclic hydrocarbon substituent. The cycloalkyl ring contains 3 to 20 carbon atoms, preferably 3 to 12 carbon atoms, more preferably 3 to 10 carbon atoms, and most preferably 3 to 7 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, and bridged cycloalkyl.

The term "heterocyclyl" refers to a saturated or partially unsaturated monocyclic or polycyclic hydrocarbon substituent containing 3 to 20 ring atoms, wherein one or more of the ring atoms are heteroatoms selected from the group consisting of nitrogen, oxygen and $S(O)_m$ (where mis an integer from 0 to 2), excluding a cyclic portion of —O—O—, —O—S— or —S—S—, and the other ring atoms are carbon atoms. The heterocyclyl preferably contains 3 to 12 ring atoms, of which 1 to 4 are heteroatoms; more preferably, the cycloalkyl ring contains 3 to 10 ring atoms. Non-limiting examples of monocyclic heterocyclyl include pyrrolidinyl, piperidinyl, piperazinyl, morpholinyl, thiomorpholinyl, homopiperazinyl, etc. Polycyclic heterocyclyl includes spiro heterocyclyl, fused heterocyclyl, and bridged heterocyclyl.

The term "spiro heterocyclyl" refers to a 5- to 20-membered polycyclic heterocyclyl group in which monocyclic rings share one atom (referred to as the spiro atom), wherein one or more ring atoms are heteroatoms selected from the group consisting of nitrogen, oxygen and $S(O)_m$ (where m is an integer from 0 to 2), and the other ring atoms are carbon atoms. It may contain one or more double bonds, but none of the rings has a fully conjugated π-electron system. It is preferably 6- to 14-membered, and more preferably 7- to 10-membered. According to the number of spiro atoms shared among the rings, the spiro heterocyclyl may be monospiro heterocyclyl, bispiro heterocyclyl or polyspiro heterocyclyl, preferably monospiro heterocyclyl and bispiro heterocyclyl, and more preferably 4-membered/4-membered, 4-membered/5-membered, 4-membered/6-membered, 5-membered/5-membered or 5-membered/6-membered monospiro heterocyclyl. Non-limiting examples of spiro heterocyclyl include:

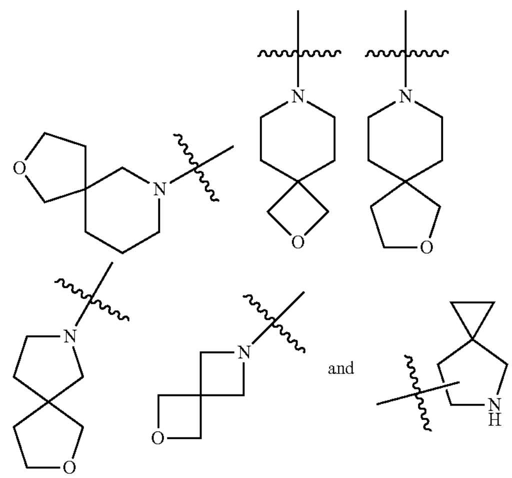

The term "fused heterocyclyl" refers to a 5- to 20-membered polycyclic heterocyclic ring system in which each ring shares a pair of adjacent atoms with other rings in the system. In fused heterocyclyl, one or more rings may contain one or more double bonds, but none of them has a fully conjugated π-electron system; one or more ring atoms are heteroatoms selected from the group consisting of nitrogen, oxygen and $S(O)_m$ (where m is an integer from 0 to 2), and the other ring atoms are carbon atoms. Preferably, the fused heterocyclyl is 6- to 14-membered, and more preferably 7- to 10-membered. According to the number of rings that form fused heterocyclyl, the fused heterocyclyl may be bicyclic, tricyclic, tetracyclic or polycyclic, preferably bicyclic or tricyclic, and more preferably 5-membered/5-membered or 5-membered/6-membered bicyclic. Non-limiting examples of fused heterocyclyl include:

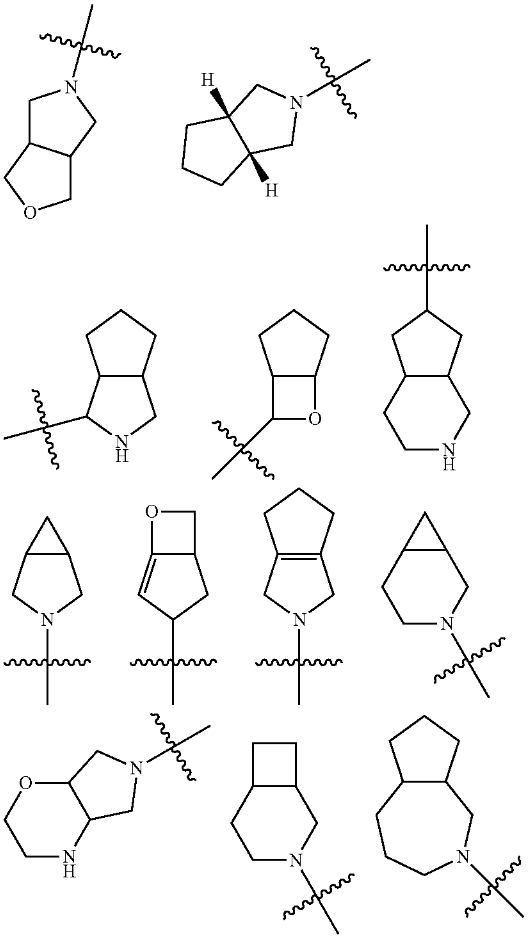

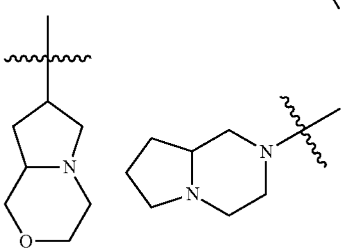

and

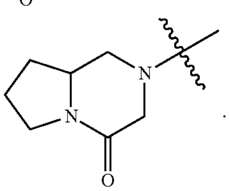

The term "bridged heterocyclyl" refers to a 5- to 14-membered polycyclic heterocyclic group in which any two rings share two atoms that are not directly linked. The bridged heterocyclyl may contain one or more double bonds, but none of the rings has a fully conjugated π-electron system; one or more ring atoms are heteroatoms selected from the group consisting of nitrogen, oxygen and $S(O)_m$ (where m is an integer from 0 to 2), and the other ring atoms are carbon atoms. The bridged heterocyclyl is preferably 6- to 14-membered, and more preferably 7- to 10-membered. According to the number of rings that form bridged heterocyclyl, the bridged heterocyclyl may be bicyclic, tricyclic, tetracyclic or polycyclic, preferably bicyclic, tricyclic or tetracyclic, and more preferably bicyclic or tricyclic. Non-limiting examples of bridged heterocyclyl include:

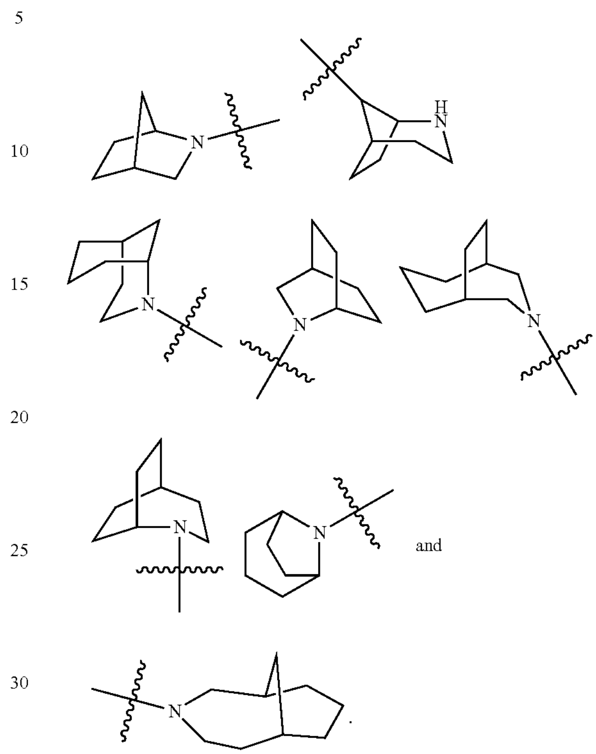

and

The heterocyclyl ring may be fused to an aryl, heteroaryl or cycloalkyl ring, wherein the ring linked to the parent structure is heterocyclyl; its non-limiting examples include:

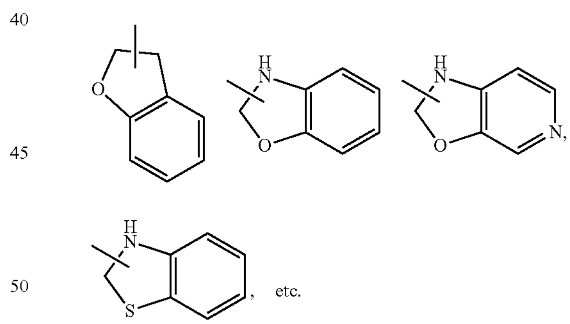

etc.

The heterocyclyl may be optionally substituted or unsubstituted. When it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "aryl" refers to a 6- to 14-membered all-carbon monocyclic or fused polycyclic (i.e., rings that share a pair of adjacent carbon atoms) group having a conjugated π-electron system. The aryl is preferably 6- to 10-membered, e.g., phenyl and naphthyl, preferably phenyl. The aryl ring may be fused to a heteroaryl, heterocyclyl or cycloalkyl ring, wherein the ring linked to the parent structure is the aryl ring; its non-limiting examples include:

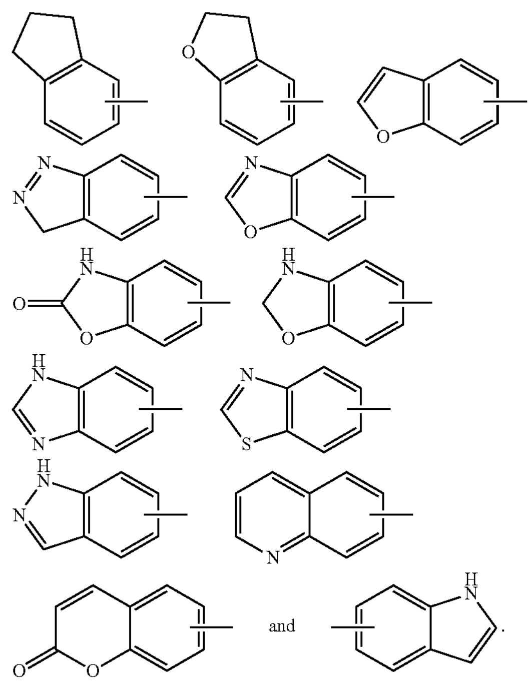

The aryl may be substituted or unsubstituted. When it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio and heterocycloalkylthio.

The term "heteroaryl" refers to a heteroaromatic system containing 1 to 4 heteroatoms and 5 to 14 ring atoms, wherein the heteroatoms are selected from the group consisting of oxygen, sulfur and nitrogen. The heteroaryl is preferably 5- to 10-membered, more preferably 5- or 6-membered, e.g., furanyl, thienyl, pyridyl, pyrrolyl, N-alkylpyrrolyl, pyrimidinyl, pyrazinyl, imidazolyl and tetrazolyl. The heteroaryl ring may be fused to an aryl, heterocyclyl or cycloalkyl ring, wherein the ring linked to the parent structure is the heteroaryl ring; its non-limiting examples include:

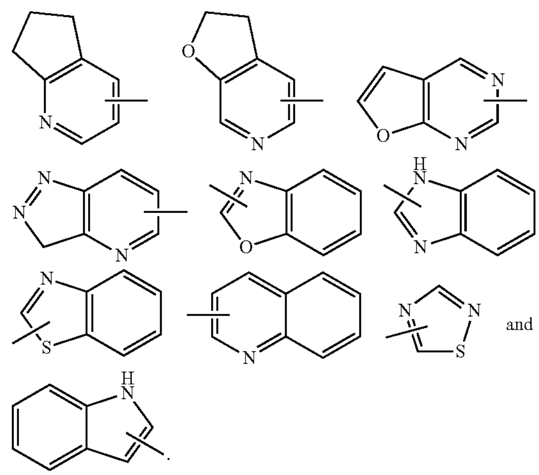

The heteroaryl may be optionally substituted or unsubstituted. When it is substituted, the substituent is preferably one or more groups independently selected from the group consisting of alkyl, alkenyl, alkynyl, alkoxy, alkylthio, alkylamino, halogen, sulfhydryl, hydroxy, nitro, cyano, cycloalkyl, heterocycloalkyl, aryl, heteroaryl, cycloalkoxy, heterocycloalkoxy, cycloalkylthio and heterocycloalkylthio.

The term "amino protecting group" is a group that is used for protecting an amino group on a molecule from being changed when other parts of the molecule are reacted and that can be easily removed. Non-limiting examples include 9-fluorenylmethoxycarbonyl, tert-butoxycarbonyl, acetyl, benzyl, allyl, p-methoxybenzyl, etc. These groups may be optionally substituted with 1-3 substituents selected from the group consisting of halogen, alkoxy and nitro. The amino protecting group is preferably 9-fluorenylmethoxycarbonyl.

The term "cycloalkylalkyl" refers to alkyl in which the hydrogen is substituted with one or more cycloalkyl groups, preferably one cycloalkyl group, wherein the alkyl is as defined above, and the cycloalkyl is as defined above.

The term "haloalkyl" refers to alkyl in which the hydrogen is substituted with one or more halogens, wherein the alkyl is as defined above. The term "deuterated alkyl" refers to alkyl in which the hydrogen is substituted with one or more deuterium atoms, wherein the alkyl is as defined above.

The term "hydroxy" refers to —OH group.

The term "halogen" refers to fluorine, chlorine, bromine or iodine.

The term "amino" refers to $—NH_2$.

The term "nitro" refers to $—NO_2$.

"Optional" or "optionally" means that the event or circumstance subsequently described may, but not necessarily, occur, and that the description includes instances where the event or circumstance occurs or does not occur. For example, "optionally comprising 1-3 antibody heavy chain variable regions" means that the antibody heavy chain variable region of a particular sequence may, but not necessarily, be present.

"Substituted" means that one or more, preferably up to 5, more preferably 1 to 3 hydrogen atoms in the group are independently substituted with a corresponding number of substituents. It goes without saying that a substituent is only in its possible chemical position, and those skilled in the art will be able to determine (experimentally or theoretically) possible or impossible substitution without undue effort. For example, it may be unstable when amino or hydroxy having a free hydrogen is bound to a carbon atom having an unsaturated (e.g., olefinic) bond.

The term "drug loading" refers to the mean number of cytotoxic drugs loaded on each antibody or an antigen-binding fragment thereof in ADC molecules, and it may also be expressed in terms of a ratio of the number of drugs to the number of antibodies. The drug loading may range from 0-12, preferably 1-10, more preferably 2-8, and most preferably 3.5-4.5 cytotoxic drugs (D) linked to each antibody or an antigen-binding fragment (Pc) thereof. In the embodiments of the present disclosure, the drug loading is denoted by n, and an exemplary value of n may be a calculated mean of one or more of 1, 2, 3, 4, 5, 6, 7, 8, 9 or 10. The mean number of drugs per ADC molecule after coupling reactions can be characterized by conventional methods such as UV/visible spectroscopy, mass spectrometry, ELISA assays and HPLC.

In one embodiment of the present disclosure, the cytotoxic drug is coupled to the N-terminal amino group, the s-amino group of a lysine residue, and/or the sulfhydryl group of the antibody or the antigen-binding fragment thereof via a linker unit. In general, the number of drug molecules that can be coupled to the antibody in a coupling reaction will be smaller than the theoretical maximum.

The loading of the cytotoxic drug can be controlled using the following non-limiting methods, including:

(1) controlling a molar ratio of a linking reagent to a monoclonal antibody, (2) controlling reaction time and temperature, and (3) selecting different reaction reagents.

For the preparation of conventional pharmaceutical compositions, refer to Chinese Pharmacopoeia.

The term "carrier" as used for the pharmaceutical composition of the present disclosure refers to a system that can alter how the drug gets into a human body and the distribution of the drug in the human body, control the release rate of the drug, and deliver the drug to a targeted organ. The drug carrier release and targeted system can reduce drug degradation and loss, reduce side effects and improve bioavailability. For example, polymeric surfactants that can be used as carriers can self-assemble due to their unique amphiphilic structures to form various forms of aggregates, such as micelles, microemulsions, gels, liquid crystals and vesicles, as preferred examples. The aggregates have the capability of encapsulating drug molecules and have good permeability for membranes, and therefore can be used as excellent drug carriers.

"Administering", "giving" and "treating", when applied to animals, humans, experimental subjects, cells, tissues, organs or biological fluid, refer to contact of an exogenous drug, a therapeutic agent, a diagnostic agent or composition with the animals, humans, subjects, cells, tissues, organs or biological fluid. "Administering", "giving" and "treating" can refer to, for example, therapeutic, pharmacokinetic, diagnostic, research and experimental methods. The treatment of cells comprises making the reagent in contact with the cells and making the reagent in contact with fluid, where the fluid is in contact with the cells. "Administering", "giving" and "treating" also refer to treating, e.g., cells by reagents, diagnosis, binding compositions or by another cell in vitro and ex vivo. "Treating", when applied to humans, veterinary or research subjects, refers to therapeutic treatment, preventive or prophylactic measures, and research and diagnostic applications.

"Treatment" refers to administering a therapeutic agent, such as a composition comprising any one of the conjugation compounds of the present disclosure, either internally or externally to a patient with one or more symptoms of a disease on which the therapeutic agent is known to have a therapeutic effect. Typically, the therapeutic agent is administered in an amount effective to alleviate one or more symptoms of the disease in the patient or population being treated to induce regression of such symptoms or to inhibit the development of such symptoms to any clinically measurable degree. The amount of therapeutic agent effective to alleviate the symptoms of any particular disease (also known as a "therapeutically effective amount") may vary depending on a variety of factors, such as the disease state, age, and weight of the patient, and the ability of the drug to produce a desired therapeutic effect in the patient. Whether a symptom of a disease has been alleviated can be evaluated by any clinical testing methods commonly used by doctors or other health care professionals to evaluate the severity or progression of the symptom. Although the embodiments of the present disclosure (for example, treatment methods or articles of manufacture) may not be effective in alleviating the symptoms of each disease of interest, they shall reduce the symptoms of a disease of interest in a statistically significant number of patients, as determined according to any statistical testing methods known in the art, such as Student t-test, chi-square test, Mann and Whitney's U test, Kruskal-Wallis test (H test), Jonckheere-Terpstra test and Wilcoxon test.

"Effective amount" comprises an amount sufficient to ameliorate or prevent a symptom or condition of a medical disease. An effective amount also refers to an amount sufficient to allow or facilitate diagnosis. The effective amount for a particular patient or veterinary subject may vary depending on the factors such as the condition to be treated, the general health of the patient, the method and route and dosage of administration, and the severity of side effects. An effective amount may be the maximum dose or administration regimen to avoid significant side effects or toxic effects.

"Exchange" refers to the exchange of a solvent system that solubilizes an antibody or ADC. For example, a high-salt or hypertonic solvent system comprising the antibody or ADC is exchanged, by physical operations, using a buffer system of a stable formulation, so that the antibody protein is present in the stable formulation. The physical operations include, but are not limited to, ultrafiltration, dialysis or reconstitution following centrifugation.

EXAMPLES

The present disclosure is further described below with reference to examples, which, however, are not intended to limit the scope of the present disclosure. The experimental methods in the examples of the present disclosure in which specific conditions are not specified are generally performed under conventional conditions, for example, by referring to Antibodies: A Laboratory Manual and Molecular Cloning: A Laboratory Manual by Cold Spring Harbor Laboratory, or under conditions recommended by the manufacturer of the raw material or the goods. Reagents without specific origins indicated were commercially available conventional reagents.

I. Antibody Drug Conjugates

Preparation of Anti-Claudin18.2 Antibodies

Example 1-1: Construction of Cell Strain Highly Expressing Claudin18.2 pCDH-hClaudin18.2 lentiviral expression vector plasmids and pVSV-G or pCMV-dR8.91 lentiviral system packaging vectors were transfected into viral packaging cells 293T using Lipofectamine 3000 transfection reagent. The medium supernatant containing viruses was collected, filtered and centrifuged at ultra-high speed. The human gastric signet ring cell carcinoma cell strain NUGC4 was infected with the concentrated virus, screened using puromycin for two to three weeks and then subjected to FACS single-cell sorting.

Claudin18.2 expression levels were determined according to tumor IHC scores. Cells expressing Claudin18.2 at a similar level to a tumor with a tumor IHC score of 3 were considered high-expression cells, and cells expressing Claudin 18.2 at a similar level to a tumor with a tumor IHC score of 2 were considered moderate-expression cells.

According to the Claudin18.2 expression levels on the surface of NUGC4 cells infected with lentivirus determined by FACS, NUGC4/hClaudin18.2 monoclonal cell strains expressing Claudin 18.2 at high levels were selected. At the same time, the Claudin 18.2 expression levels on the surface of wild-type NUGC4 cells were also determined by FACS, and NUGC4 clonal cell strains expressing Claudin18.2 at moderate levels were selected. The wild-type NUGC4 cells were cells expressing Claudin 18.2 at low levels.

The selected monoclonal cell strains were expanded and stored frozen in a bank for subsequent experiments.

Sequence of Claudin18.2 Genbank: NP_001002026 (SEQ ID NO: 1):
MAVTACQGLGFVVSLIGIAGIIAATCMDQWSTQDLYNNPVTAVFNYQGLWRSC

VRESSGFTECRGYFTLLGLPAMLQAVRALMIVGIVLGAIGLLVSIFALKCIRIGS

MEDSAKANMTLTSGIMFIVSGLCAIAGVSVFANMLVTNFWMSTANMYTGMGG

MVQTVQTRYTFGAALFVGWVAGGLTLIGGVMMCIACRGLAPEETNYKAVSYH

ASGHSVAYKPGGFKASTGFGSNTKNKKIYDGGARTEDEVQSYPSKHDYV.

DNA sequence of Claudin18.2 (SEQ ID NO: 2):
AGAATTGCGC TGTCCACTTG TCGTGTGGCT CTGTGTCGAC ACTGTGCGCC

ACCATGGCCG TGACTGCCTG TCAGGGCTTG GGGTTCGTGG TTTCACTGAT

TGGGATTGCG GGCATCATTG CTGCCACCTG CATGGACCAG TGGAGCACCC

AAGACTTGTA CAACAACCCC GTAACAGCTG TTTTCAACTA CCAGGGGCTG

TGGCGCTCCT GTGTCCGAGA GAGCTCTGGC TTCACCGAGT GCCGGGGCTA

CTTCACCCTG CTGGGGCTGC CAGCCATGCT GCAGGCAGTG CGAGCCCTGA

TGATCGTAGG CATCGTCCTG GGTGCCATTG GCCTCCTGGT ATCCATCTTT

GCCCTGAAAT GCATCCGCAT TGGCAGCATG GAGGACTCTG CCAAAGCCAA

CATGACACTG ACCTCCGGGA TCATGTTCAT TGTCTCAGGT CTTTGTGCAA

TTGCTGGAGT GTCTGTGTTT GCCAACATGC TGGTGACTAA CTTCTGGATG

TCCACAGCTA ACATGTACAC CGGCATGGGT GGGATGGTGC AGACTGTTCA

GACCAGGTAC ACATTTGGTG CGGCTCTGTT CGTGGGCTGG GTCGCTGGAG

GCCTCACACT AATTGGGGGT GTGATGATGT GCATCGCCTG CCGGGGCCTG

GCACCAGAAG AAACCAACTA CAAAGCCGTT TCTTATCATG CCTCAGGCCA

CAGTGTTGCC TACAAGCCTG GAGGCTTCAA GGCCAGCACT GGCTTTGGGT

CCAACACCAA AAACAAGAAG ATATACGATG GAGGTGCCCG

CACAGAGGAC GAGGTACAAT CTTATCCTTC CAAGCACGAC TATGTGTAAT

GCTCTAAGAC CTCTCAGCACGGGCGGAAGA AACTCCCGGA GAGCTCACCC

AAAAAACAAG GAGATCCCAT CTAGATTTCT TCTTGCTTTT GACTCACAGC

TGGAAGTTAG AAAAGCCTCG ATTTCATCTT TGGAGAGGCC AAATGGTCTT

AGCCTCAGTC TCTGTCTCTA AATATTCCAC CATAAAACAG CTGAGTTATT

TATGAATTAG AGGCTATAGC TCACATTTTC AATCCTCTAT TTCTTTTTTT

AAATATAACT TTCTACTCTG ATGAGAGAAT GTGGTTTTAA TCTCTCTCTC

ACATTTTGAT GATTTAGACA GACTCCCCCT CTTCCTCCTA GTCAATAAAC

CCATTGATGA TCTATTTCCC AGCTTATCCC CAAGAAAACT TTTGAAAGGA

AAGAGTAGAC CCAAAGATGT TATTTTCTGC TGTTTGAATT TTGTCTCCCC

ACCCCCAACT TGGCTAGTAA TAAACACTTA CTGAAGAAGA AGCAATAAGA

GAAAGATATT TGTAATCTCT CCAGCCCATG ATCTCGGTTT TCTTACACTG

TGATCTTAAA AGTTACCAAA CCAAAGTCAT TTTCAGTTTG AGGCAACCAA

ACCTTTCTAC TGCTGTTGAC ATCTTCTTAT TACAGCAACA CCATTCTAGG

AGTTTCCTGA GCTCTCCACT GGAGTCCTCT TTCTGTCGCG GGTCAGAAAT

TGTCCCTAGA TGAATGAGAA AATTATTTTT TTTAATTTAA GTCCTAAATA

-continued

TAGTTAAAAT AAATAATGTT TTAGTAAAAT GATACACTAT CTCTGTGAAA

TAGCCTCACC CCTACATGTG GATAGAAGGA AATGAAAAAA TAATTGCTTT

GACATTGTCT ATATGGTACT TTGTAAAGTC ATGCTTAAGT ACAAATTCCA

TGAAAAGCTC ACTGATCCTA ATTCTTTCCC TTTGAGGTCT CTATGGCTCT

GATTGTACAT GATAGTAAGT GTAAGCCATG TAAAAAGTAA ATAATGTCTG

GGCACAGTGG CTCACGCCTG TAATCCTAGCACTTTGGGAG GCTGAGGAGG

AAGGATCACT TGAGCCCAGA AGTTCGAGAC

TAGCCTGGGC AACATGGAGAAGCCCTGTCT CTACAAAATA CAGAGAGAAA

AAATCAGCCA GTCATGGTGG CCTACACCTG TAGTCCCAGC ATTCCGGGAG

GCTGAGGTGG GAGGATCACT TGAGCCCAGG GAGGTTGGGG CTGCAGTGAG

CCATGATCAC ACCACTGCAC TCCAGCCAGG TGACATAGCGAGATCCTGTC

TAAAAAAATA AAAAATAAAT AATGGAACAC AGCAAGTCCT

AGGAAGTAGGTTAAAACTAA TTCTTTAAAA AAAAAAAAAA GTTGAGCCTG

AATTAAATGT AATGTTTCCA AGTGACAGGT ATCCACATTT GCATGGTTAC

AAGCCACTGC CAGTTAGCAG TAGCACTTTC CTGGCACTGT GGTCGGTTTT

GTTTTGTTTT GCTTTGTTTA GAGACGGGGT CTCACTTTCC AGGCTGGCCT

CAAACTCCTG CACTCAAGCA ATTCTTCTAC CCTGGCCTCC CAAGTAGCTG

GAATTACAGG TGTGCGCCAT CACAACTAGC TGGTGGTCAG TTTTGTTACT

CTGAGAGCTG TTCACTTCTC TGAATTCACC TAGAGTGGTT GGACCATCAG

ATGTTTGGGC AAAACTGAAA GCTCTTTGCA ACCACACACC TTCCCTGAGC

TTACATCACT GCCCTTTTGA GCAGAAAGTC TAAATTCCTT CCAAGACAGT

AGAATTCCAT CCCAGTACCA AAGCCAGATA GGCCCCCTAG GAAACTGAGG

TAAGAGCAGT CTCTAAAAAC TACCCACAGC AGCATTGGTG CAGGGGAACT

TGGCCATTAG GTTATTATTT GAGAGGAAAG TCCTCACATC AATAGTACAT

ATGAAAGTGA CCTCCAAGGG GATTGGTGAA TACTCATAAG GATCTTCAGG

CTGAACAGAC TATGTCTGGG GAAAGAACGG ATTATGCCCC ATTAAATAAC

AAGTTGTGTT CAAGAGTCAG AGCAGTGAGCTCAGAGGCCC TTCTCACTGA

GACAGCAACA TTTAAACCAA ACCAGAGGAA GTATTTGTGG AACTCACTGC

CTCAGTTTGG GTAAAGGATG AGCAGACAAG TCAACTAAAG

AAAAAAGAAA AGCAAGGAGGAGGGTTGAGC AATCTAGAGC ATGGAGTTTG

TTAAGTGCTC TCTGGATTTG AGTTGAAGAG CATCCATTTG AGTTGAAGGC

CACAGGGCAC AATGAGCTCT CCCTTCTACC ACCAGAAAGT CCCTGGTCAG

GTCTCAGGTA GTGCGGTGTG GCTCAGCTGG GTTTTTAATT AGCGCATTCT

CTATCCAACA TTTAATTGTT TGAAAGCCTC CATATAGTTA GATTGTGCTT

TGTAATTTTG TTGTTGTTGC TCTATCTTAT TGTATATGCA TTGAGTATTA

ACCTGAATGT TTTGTTACTT AAATATTAAA AACACTGTTA TCCTACAGTT.

Example 1-2: Production of Anti-Human Claudin18.2 Monoclonal Antibody

1. Immunization

An anti-human Claudin18.2 monoclonal antibody was produced by immunizing mice.

Laboratory SJL white mice, female, 6-8 weeks of age (Charles River Laboratory Animal Technology Co., Ltd., Beijing, animal production license number: SCXK(Beijing) 2012-0001). Housing environment: SPF. The purchased mice were housed in a laboratory environment for 1 week, in 12/12 hour light/dark cycles, at a temperature of 20-25° C. with humidity at 40-60%. The acclimatized mice were immunized according to the following scheme. The antigens for immunization were huClaudin18.2-HEK293 cells (a HEK-293 cell strain stably transfected with human Claudin18.2 plasmid).

Immunization scheme: Prior to the first cell immunization, each mouse was intraperitoneally (IP) injected with 0.1 mL of TiterMax® Gold Adjuvant (Sigma Cat No. T2684), and, a half hour later, with 0.1 mL of normal saline-diluted cellular fluid at a concentration of $1\times10^8$/mL. The cells were uniformly pipetted, and then inoculation was performed on days 0, 14, 28, 42 and 56. Blood was collected on days 21, 35, 49 and 63, and the antibody titer in mouse serum was determined by ELISA. After 4-5 immunizations, mice in which the antibody titer in serum was high and was reaching a plateau were selected for splenocyte fusion. The mice were immunized with a booster dose of $1\times10^7$ cells by intraperitoneal injection (IP) 3 days prior to splenocyte fusion.

2. Spleen Cell Fusion

Spleen lymphocytes and myeloma cells, Sp2/0 cells (ATCC® CRL-8287™), were fused by following a PEG-mediated fusion procedure to obtain hybridoma cells. The hybridoma cells were resuspended in complete medium (IMDM medium containing 20% FBS, 1×HAT and 1×OPI) at a density of $0.5\text{-}1\times10^6$/mL and seeded in a 96-well plate at 100 μL/well. The plate was incubated at 37° C. with 5% $CO_2$ for 3-4 days, supplemented with HAT complete medium at 100 μL/well, and incubated for another 3-4 days to form clones. The supernatant was removed and HT complete medium (IMDM medium containing 20% FBS, 1×HT and 1×OPI) was added at 200 μL/well. The plate was incubated at 37° C. with 5% $CO_2$ for 3 days, followed by an ELISA assay.

3. Hybridoma Cell Screening

The culture supernatants were assayed using a combined ELISA method according to the density at which the hybridoma cells were grown. Cells that had good binding capacity to huClaudin18.2-HEK293 cells but were not bound to HEK293 were selected, expanded and frozen in time. Subcloning was performed two to three times to obtain single-cell clones.

A cell binding assay was performed for each cell subcloning. Hybridoma clones were obtained by the above screening process, and antibodies were further prepared using a serum-free cell culture method. The antibodies were purified, according to the purification example, for use in the test examples.

Example 1-3: Humanization of Murine Antibodies

Monoclonal hybridoma cell strains mAb1901 and mAb1902 with high in vitro activity were selected. The monoclonal antibody sequences therein were cloned, followed by humanization, recombinant expression and activity evaluation.

The cloning of a sequence from hybridoma is as follows. Hybridoma cells at logarithmic growth phase were collected, and the RNA was extracted using Trizol (INVITROGEN®, 15596-018) (following the procedures in the kit instructions) and reverse transcribed (PrimeScript™ Reverse Transcriptase, Takara, cat #2680A). The cDNA obtained by reverse transcription was amplified by PCR using mouse Ig-Primer Set (Novagen, TB326 Rev.B 0503) and then sent to a sequencing company for sequencing. The amino acid sequences corresponding to the obtained DNA sequences are set forth in SEQ ID NOs: 3-6:

```
murine heavy chain variable region of mAb1901
                                                  (SEQ ID NO: 3)
EVQLMESGGGLVKPGGSLKLSCAASGFTFSDYGIHWVRQAPEMGLEWIA
YISRGSSTIYYADTVKGRFTMSRDNAKNTLFLQMTSLRSEDTAMYYCAR
GGYDTRNAMDYWGQGTSVTVSS;

Murine light chain variable region of mAb1901
                                                  (SEQ ID NO: 4)
DIVMTQSPSSLSVSAGEKVTMSCKSSQSLLNSGNQKNYLAWYQQKPGQP
PKLLIYGASTRASGVPDRFTGSGSGTDFTLTISSVQAEDLAIYHCQNDL
YYPLTFGAGTKLELK;

Murine heavy chain variable region of mAb1902
                                                  (SEQ ID NO: 5)
EVQLQESGAELVKPGASVKLSCKASGYIFTSYWMHWVKQRPGQGLEWIG
MIHPNSGSTNYNEKFKGKATLTLDKSSSTAYMQLSSLPSEDSAVYYCAR
LKTGNSFDYWGQGTTLTVSS;

Murine light chain variable region of mAb1902
                                                  (SEQ ID NO: 6)
DIVLTQSPSSLTVTAGEKVTMSCKSSQSLLNSGNQKNYLTWYQQKPGQP
PKLLIYWASTRESGVPDRFTGSGSGTDFTLTISSVQAEDLAIYYCQNAY
TYPFTFGSGTKLEIK;
```

The above murine heavy chain and light chain variable regions were joined to the heavy chain constant region of human IgG1 antibody and the human κ light chain constant region described below, respectively, to form chimeric antibodies ch1901 and ch1902.

The constant regions of each antibody were selected from the group consisting of the following sequences:

```
Heavy chain constant region of human IgG1
antibody:
                                                  (SEQ ID NO: 7)
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK;

Human κ light chain constant region:
                                                  (SEQ ID NO: 8)
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC.
```

Murine monoclonal antibodies are humanized according to methods disclosed in many publications in the art. Briefly, human constant domains were used in place of parent (murine antibody) constant domains, and human germline antibody sequences were selected, based on the homology of the murine and human antibodies, for CDR grafting. The present invention selects candidate molecules with good activity for humanization, and the results are as follows.

1. CDRs of Murine Antibodies

The amino acid residues of the VH/VL CDRs in Table 1 were identified using the Kabat numbering scheme and annotated.

The CDR sequences of the murine antibodies are described in Table 1:

TABLE 1

| CDR sequences of murine antibodies | |
|---|---|
| Antibody | mAb1901 |
| HCDR1 | DYGIH (SEQ ID NO: 9) |
| HCDR2 | YISRGSSTIYYADTVKG (SEQ ID NO: 10) |
| HCDR3 | GGYDTRNAMDY (SEQ ID NO: 11) |
| LCDR1 | KSSQSLLNSGNQKNYLA (SEQ ID NO: 12) |
| LCDR2 | GASTRAS (SEQ ID NO: 13) |
| LCDR3 | QNDLYYPLT (SEQ ID NO: 14) |
| Antibody | mAb1902 |
| HCDR1 | SYWMH (SEQ ID NO: 15) |
| HCDR2 | MIHPNSGSTNYNEKFKGR (SEQ ID NO: 16) |
| HCDR3 | LKTGNSFDY (SEQ ID NO: 17) |
| LCDR1 | KSSQSLLNSGNQKNYLT (SEQ ID NO: 18) |
| LCDR2 | WASTRES (SEQ ID NO: 19) |
| LCDR3 | QNAYTYPFT (SEQ ID NO: 20) |

2. Selection of Human Germline FR Region Sequences

Based on the typical structure of the murine antibody VH/VL CDR obtained, the heavy chain and light chain variable region sequences were compared with an antibody Germline database to obtain a human germline template with high homology. The human germline light chain framework region was derived from a human κ light chain gene.

2.1. Humanization of mAb1901 and Reverse Mutation Design

A suitable human antibody germline was selected to perform humanization on mAb1901 murine antibody. The CDRs of murine antibody mAb1901 were grafted into the selected humanization template to replace humanized variable regions, followed by recombination with an IgG constant region to form a complete antibody. Meanwhile, reverse mutations were introduced into the FR region in the V region of the humanized antibody. Exemplary reverse mutations and combinations thereof are as follows:

TABLE 2

| Humanized antibodies of mAb1901 and reverse mutations* | | | |
|---|---|---|---|
| Light chain variable regions of humanized antibody of mAb1901 | | Heavy chain variable regions of humanized antibody of mAb1901 | |
| VL1 | None | VH1 | None |
| VL2 | N22S | VH2 | N82T |
| VL3 | N22S, V85I, Y87H | VH3 | V481, N82T |
| | | VH4 | I69M, N82T |

*All amino acid positions in the table are numbered according to the Kabat numbering scheme; in N82T of the heavy chain variable region, 82 refers to position 82A according to the Kabat scheme.

TABLE 3

| Light chain and heavy chain variable region sequences of humanized antibodies of mAb1901 | |
|---|---|
| Name of variable region (SEQ ID NO:) | Sequence |
| VL1 (SEQ ID NO: 21) | DIVMTQSPDSLAVSLGERATINCKSSQSLLNSGNQKNYLAWYQQKPGQP PKLLIYGASTRASGVPDRFSGSGSGTDFTLTISSLQAEDVAVYYCQNDLY YPLTFGQGTKLEIK |
| VL2 (SEQ ID NO: 22) | DIVMTQSPDSLAVSLGERATISCKSSQSLLNSGNQKNYLAWYQQKPGQP PKLLIYGASTRASGVPDRFSGSGSGTDFTLTISSLQAEDVAVYYCQNDLY YPLTFGQGTKLEIK |
| VL3 (SEQ ID NO: 23) | DIVMTQSPDSLAVSLGERATISCKSSQSLLNSGNQKNYLAWYQQKPGQP PKLLIYGASTRASGVPDRFSGSGSGTDFTLTISSLQAEDVA**I**Y**H**CQNDLY YPLTFGQGTKLEIK |
| VH1 (SEQ ID NO: 24) | EVQLVESGGGLVQPGGSLRLSCAASGFTFSDYGIHWVRQAPGKGLEWV AYISRGSSTIYYADTVKGRFTISRDNAKNSLYLQMNSLRAEDTAVYYCA RGGYDTRNAMDYWGQGTTVTVSS |
| VH2 (SEQ ID NO: 25) | EVQLVESGGGLVQPGGSLRLSCAASGFTFSDYGIHWVRQAPGKGLEWV AYISRGSSTIYYADTVKGRFTISRDNAKNSLYLQM**T**SLRAEDTAVYYCA RGGYDTRNAMDYWGQGTTVTVSS |
| VH3 (SEQ ID NO: 26) | EVQLVESGGGLVQPGGSLRLSCAASGFTFSDYGIHWVRQAPGKGLEW**I** AYISRGSSTIYYADTVKGRFTISRDNAKNSLYLQM**T**SLRAEDTAVYYCA RGGYDTRNAMDYWGQGTTVTVSS |

TABLE 3-continued

| Light chain and heavy chain variable region sequences of humanized antibodies of mAb1901 | |
|---|---|
| Name of variable region (SEQ ID NO:) | Sequence |
| VH4 (SEQ ID NO: 27) | EVQLVESGGGLVQPGGSLRLSCAASGFTFSDYGIHWVRQAPGKGLEWV AYISRGSSTIYYADTVKGRFT**M**SRDNAKNSLYLQM**T**SLRAEDTAVYYC ARGGYDTRNAMDYWGQGTTVTVSS |

The corresponding heavy chain variable region in the table above was linked to the human IgG1 heavy chain constant region set forth in SEQ ID NO: 7 to form a heavy chain of a full-length antibody, and the light chain variable region was linked to the human κ light chain constant region set forth in SEQ ID NO: 8 to form a light chain of a full-length antibody. In other embodiments, the heavy chain variable region and the light chain variable region may also be linked to other heavy chain constant regions and light chain constant regions, respectively, to form a full-length antibody.

2.2. Humanization of mAb1902 and Reverse Mutation Design

A suitable human antibody germline was selected to perform humanization on mAb1902 murine antibody. The CDRs of murine antibody mAb1902 were grafted into the selected humanization template to replace humanized variable regions, followed by recombination with an IgG constant region to form a complete antibody. Meanwhile, reverse mutations were introduced into the FR region in the V region of the humanized antibody. Exemplary reverse mutations and combinations thereof are as follows:

TABLE 4

| Humanized antibodies of mAb1902 and reverse mutation design therefor* | | | |
|---|---|---|---|
| Light chain variable regions of humanized antibody of mAb1902 | | Heavy chain variable regions of humanized antibody of mAb1902 | |
| VL11 | None | VH11 | None |
| VL12 | M4L | VH12 | I69L, R71L, T73K |
| VL13 | M4L, N22S | VH13 | M481, R66K, V67A, I69L, R71L, T73K |
| | | VH14 | R38K, A40R, M48I, R66K, V67A, I69L, R71L, T73K |

*All amino acid positions in the table are numbered according to the Kabat numbering scheme.

TABLE 5

| Light chain and heavy chain variable region sequences of mAb1902 humanized antibody | |
|---|---|
| Name of variable region (SEQ ID NO:) | Sequence |
| VL11 (SEQ ID NO: 28) | DIVMTQSPDSLAVSLGERATINCKSSQSLLNSGNQKNYLTWYQQKPGQ PPKLLIYWASTRESGVPDRFSGSGSGTDFTLTISSLQAEDVAVYYCQNA YTYPFTFGQGTKLEIK |
| VL12 (SEQ ID NO: 29) | DIVLTQSPDSLAVSLGERATINCKSSQSLLNSGNQKNYLTWYQQKPGQP PKLLIYWASTRESGVPDRFSGSGSGTDFTLTISSLQAEDVAVYYCQNAY TYPFTFGQGTKLEIK |
| VL13 (SEQ ID NO: 30) | DIVLTQSPDSLAVSLGERATISCKSSQSLLNSGNQKNYLTWYQQKPGQP PKLLIYWASTRESGVPDRFSGSGSGTDFTLTISSLQAEDVAVYYCQNAY TYPFTFGQGTKLEIK |
| VH11 (SEQ ID NO: 31) | EVQLVQSGAEVKKPGASVKVSCKASGYTFTSYWMHWVRQAPGQRLE WMGMIHPNSGSTNYNEKFKGRVTITRDTSASTAYMELSSLRSEDTAVY YCARLKTGNSFDYWGQGTTVTVSS |
| VH12 (SEQ ID NO: 32) | EVQLVQSGAEVKKPGASVKVSCKASGYTFTSYWMHWVRQAPGQRLE WMGMIHPNSGSTNYNEKFKGRVTLTLDKSASTAYMELSSLRSEDTAVY YCARLKTGNSFDYWGQGTTVTVSS |
| VH13 (SEQ ID NO: 33) | EVQLVQSGAEVKKPGASVKVSCKASGYTFTSYWMHWVRQAPGQRLE WIGMIHPNSGSTNYNEKFKGKATLTLDKSASTAYMELSSLRSEDTAVY YCARLKTGNSFDYWGQGTTVTVSS |
| VH14 (SEQ ID NO: 34) | EVQLVQSGAEVKKPGASVKVSCKASGYTFTSYWMHWVKQRPGQRLE WIGMIHPNSGSTNYNEKFKGKATLTLDKSASTAYMELSSLRSEDTAVY YCARLKTGNSFDYWGQGTTVTVSS |

The corresponding heavy chain variable region in the table above was linked to the human IgG1 heavy chain constant region set forth in SEQ ID NO: 7 to form a heavy chain of a full-length antibody, and the light chain variable region was linked to the human κ light chain constant region set forth in SEQ ID NO: 8 to form a light chain of a full-length antibody.

Chimeric Antibody ch1901

Heavy chain of ch1901:

(SEQ ID NO: 35)

EVQLMESGGGLVKPGGSLKLSCAASGFTFSDYGIHWVRQAPEMGLEWIA

YISRGSSTIYYADTVKGRFTMSRDNAKNTLFLQMTSLRSEDTAMYYCAR

GGYDTRNAMDYWGQGTSVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK;

Light chain of ch1901:

(SEQ ID NO: 36)

DIVMTQSPSSLSVSAGEKVTMSCKSSQSLLNSGNQKNYLAWYQQKPGQP

PKLLIYGASTRASGVPDRFTGSGSGTDFTLTISSVQAEDLAIYHCQNDL

YYPLTFGAGTKLELKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC;

Chimeric antibody ch1902

Heavy chain of ch1902:

(SEQ ID NO: 37)

EVQLQESGAELVKPGASVKLSCKASGYIFTSYWMHWVKQRPGQGLEWIG

MIHPNSGSTNYNEKFKGKATLTLDKSSSTAYMQLSSLPSEDSAVYYCAR

LKTGNSFDYWGQGTTLTVSSASTKGPSVFPLAPSSKSTSGGTAALGCLV

-continued

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPGK;

Light chain of ch 1902:

(SEQ ID NO: 38)

DIVLTQSPSSLTVTAGEKVTMSCKSSQSLLNSGNQKNYLTWYQQKPGQP

PKLLIYWASTRESGVPDRFTGSGSGTDFTLTISSVQAEDLAIYYCQNAY

TYPFTFGSGTKLEIKRTVAAPSVFIFPPSDEQLKSGTASVVCLLNNFYP

REAKVQWKVDNALQSGNSQESVTEQDSKDSTYSLSSTLTLSKADYEKHK

VYACEVTHQGLSSPVTKSFNRGEC.

TABLE 6

| Humanized antibodies of mAb1901 | | | | |
|---|---|---|---|---|
| Light and heavy chains | H1 | H2 | H3 | H4 |
| L1 | h1901-1 | h1901-2 | h1901-3 | h1901-4 |
| L2 | h1901-5 | h1901-6 | h1901-7 | h1901-8 |
| L3 | h1901-9 | h1901-10 | h1901-11 | h1901-12 |

The light chain and heavy chain sequences of the full-length antibodies are as follows:

TABLE 7

| Light chain and heavy chain sequences of humanized antibodies of mAb1901 | |
|---|---|
| Name of variable region (SEQ ID NO:) | Sequence |
| L1 (SEQ ID NO: 39) | DIVMTQSPDSLAVSLGERATINCKSSQSLLNSGNQKNYLAWYQQKPGQPPKLLI YGASTRASGVPDRFSGSGSGTDFTLTISSLQAEDVAVYYCQNDLYYPLTFGQGTK LEIKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFNR GEC |
| L2 (SEQ ID NO: 40) | DIVMTQSPDSLAVSLGERATISCKSSQSLLNSGNQKNYLAWYQQKPGQPPKLLIY GASTRASGVPDRFSGSGSGTDFTLTISSLQAEDVAVYYCQNDLYYPLTFGQGTKL EIKRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNRG EC |
| L3 (SEQ ID NO: 41) | DIVMTQSPDSLAVSLGERATISCKSSQSLLNSGNQKNYLAWYQQKPGQPPKLLIY GASTRASGVPDRFSGSGSGTDFTLTISSLQAEDVAIYHCQNDLYYPLTFGQGTKL EIKRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNRG EC |
| H1 (SEQ ID NO: 42) | EVQLVESGGGLVQPGGSLRLSCAASGFTFSDYGIHWVRQAPGKGLEWVAYISRG SSTIYYADTVKGRFTISRDNAKNSLYLQMNSLRAEDTAVYYCARGGYDTRNAM DYWGQGTTVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEY |

TABLE 7-continued

| Light chain and heavy chain sequences of humanized antibodies of mAb1901 | |
|---|---|
| Name of variable region (SEQ ID NO:) | Sequence |
| | KCKVSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSCSVM HEALHNHYTQKSLSLSPGK |
| H2 (SEQ ID NO: 43) | EVQLVESGGGLVQPGGSLRLSCAASGFTFSDYGIHWVRQAPGKGLEWVAYISRG SSTIYYADTVKGRFTISRDNAKNSLYLQMTSLRAEDTAVYYCARGGYDTRNAM DYWGQGTTVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSCSVM HEALHNHYTQKSLSLSPGK |
| H3 (SEQ ID NO: 44) | EVQLVESGGGLVQPGGSLRLSCAASGFTFSDYGIHWVRQAPGKGLEWIAYISRG SSTIYYADTVKGRFTISRDNAKNSLYLQMTSLRAEDTAVYYCARGGYDTRNAM DYWGQGTTVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSCSVM HEALHNHYTQKSLSLSPGK |
| H4 (SEQ ID NO: 45) | EVQLVESGGGLVQPGGSLRLSCAASGFTFSDYGIHWVRQAPGKGLEWVAYISRG SSTIYYADTVKGRFTMSRDNAKNSLYLQMTSLRAEDTAVYYCARGGYDTRNAM DYWGQGTTVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSCSVM HEALHNHYTQKSLSLSPGK |

TABLE 8

| Humanized antibodies of mAb1902 | | | | |
|---|---|---|---|---|
| Light and heavy chains | H11 | H12 | H13 | H14 |
| L11 | h1902-1 | h1902-2 | h1902-3 | h1902-4 |
| L12 | h1902-5 | h1902-6 | h1902-7 | h1902-8 |
| L13 | h1902-9 | h1902-10 | h1902-11 | h1902-12 |

The light chain and heavy chain sequences of the full-length antibodies are as follows:

TABLE 9

| Light chain and heavy chain sequences of humanized antibodies of mAb1901 | |
|---|---|
| Name of variable region (SEQ ID NO:) | Sequence |
| L11 (SEQ ID NO: 46) | DIVMTQSPDSLAVSLGERATINCKSSQSLLNSGNQKNYLTWYQQKPGQPPKLLIY WASTRESGVPDRFSGSGSGTDFTLTISSLQAEDVAVYYCQNAYTYPFTFGQGTKL EIKRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNRG EC |
| L12 (SEQ ID NO: 47) | DIVLTQSPDSLAVSLGERATINCKSSQSLLNSGNQKNYLTWYQQKPGQPPKLLIY WASTRESGVPDRFSGSGSGTDFTLTISSLQAEDVAVYYCQNAYTYPFTFGQGTKL EIKRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNRG EC |

TABLE 9-continued

Light chain and heavy chain sequences of humanized antibodies of mAb1901

| Name of variable region (SEQ ID NO:) | Sequence |
|---|---|
| L13 (SEQ ID NO: 48) | DIVLTQSPDSLAVSLGERATISCKSSQSLLNSGNQKNYLTWYQQKPGQPPKLLIY WASTRESGVPDRFSGSGSGTDFTLTISSLQAEDVAVYYCQNAYTYPFTFGQGTKL EIKRTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNRG EC |
| H11 (SEQ ID NO: 49) | EVQLVQSGAEVKKPGASVKVSCKASGYTFTSYWMHWVRQAPGQRLEWMGMI HPNSGSTNYNEKFKGRVTITRDTSASTAYMELSSLRSEDTAVYYCARLKTGNSFD YWGQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYPS DIAVEWESNGQPENNYKTTPPVLDSDGSFFLYSKLTVDKSRWQQGNVFSCSVM HEALHNHYTQKSLSLSPGK |
| H12 (SEQ ID NO: 50) | EVQLVQSGAEVKKPGASVKVSCKASGYTFTSYWMHWVRQAPGQRLEWMGMI HPNSGSTNYNEKFKGRVTLTLDKSASTAYMELSSLRSEDTAVYYCARLKTGNSF DYWGQGTTVTVSSASTKGPSVFPLAPSSKSTSGGTAALGCLVKDYFPEPVTVSW NSGALTSGVHTFPAVLQSSGLYSLSSVVTVPSSSLGTQTYICNVNHKPSNTKVDK KVEPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEY KCKVSNKALPAPIEKTISKAKGQPREPQVYTLPPSRDELTKNQVSLTCLVKGFYP SDIAVEWESNGQPENNYKTTPPVLDSDGSFFLYSKLTVDKSRWQQGNVFSCSVM HEALHNHYTQKSLSLSPGK |
| H13 (SEQ ID NO: 51) | EVQLVQSGAEVKKPGASVKVSCKASGYTFTSYWMHWVRQAPGQRLEWIGMIH PNSGSTNYNEKFKGKATLTLDKSASTAYMELSSLRSEDTAVYYCARLKTGNSFD YWGQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYPS DIAVEWESNGQPENNYKTTPPVLDSDGSFFLYSKLTVDKSRWQQGNVFSCSVM HEALHNHYTQKSLSLSPGK |
| H14 (SEQ ID NO: 52) | EVQLVQSGAEVKKPGASVKVSCKASGYTFTSYWMHWVKQRPGQRLEWIGMIH PNSGSTNYNEKFKGKATLTLDKSASTAYMELSSLRSEDTAVYYCARLKTGNSFD YWGQGTTVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDKK VEPKSCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYK CKVSNKALPAPIEKTISKAKGQPREPQVYTLPPSRDELTKNQVSLTCLVKGFYPS DIAVEWESNGQPENNYKTTPPVLDSDGSFFLYSKLTVDKSRWQQGNVFSCSVM HEALHNHYTQKSLSLSPGK |

A positive control antibody of the present disclosure is IMAB-362 (from WO2016166122).

Heavy chain (SEQ ID NO: 53)

QVQLQQPGAE LVRPGASVKL SCKASGYTFT SYWINWVKQRPGQGLEWIGN

IYPSDSYTNY NQKFKDKATL TVDKSSSTAY MQLSSPTSED SAVYYCTRSW

RGNSFDYWGQGTTLTVSSAS TKGPSVFPLA PSSKSTSGGT AALGCLVKDY

FPEPVTVSWN SGALTSGVHT FPAVLQSSGL YSLSSVVTVP SSSLGTQTYI

CNVNHKPSNT KVDKRVEPKS CDKTHTCPPC PAPELLGGPS VFLFPPKPKD

TLMISRTPEV TCVVVDVSHE DPEVKFNWYV DGVEVHNAKTKPREEQYNST

YRVVSVLTVL HQDWLNGKEY KCKVSNKALP APIEKTISKA

KGQPREPQVY

-continued

```
TLPPSREEMT KNQVSLTCLV KGFYPSDIAV EWESNGQPEN NYKTTPPVLD

SDGSFFLYSK LTVDKSRWQQGNVFSCSVMH EALHNHYTQK SLSLSPGK;

Light chain
                                        (SEQ ID NO: 54)
DIVMTQSPSS LTVTAGEKVT MSCKSSQSLL NSGNQKNYLT WYQQKPGQPP

KLLIYWASTR ESGVPDRFTG SGSGTDFTLT ISSVQAEDLA VYYCQNDYSY

PFTFGSGTKL EIKRTVAAPS VFIFPPSDEQ LKSGTASVVC LLNNFYPREA

KVQWKVDNAL QSGNSQESVT EQDSKDSTYS LSSTLTLSKA

DYEKHKVYACEVTHQGLSSP VTKSFNRGEC.
```

The above antibodies were cloned, expressed and purified using conventional gene cloning and recombinant expression methods.

Preparation of Anti-Claudin18.2 ADC Conjugates

Drug

The drug moiety of the anti-Claudin 18.2 ADC conjugates of the present disclosure may be any suitable drug. Particularly suitable drugs are described, for example, in PCT Publication No. WO2020063676A1, which is incorporated herein by reference in its entirety. The compound 9-A of the present disclosure is N-((2R,10S)-10-benzyl-2-cyclopropyl-1-(((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)amino)-1,6,9,12,15-pentaoxo-3-oxa-5,8,11,14-tetraazahexadec-16-yl)-6-(2,5-dioxo-2,5-dihydro-1H-pyrrol-1-yl)hexanamide, which has the structure below:

9-A

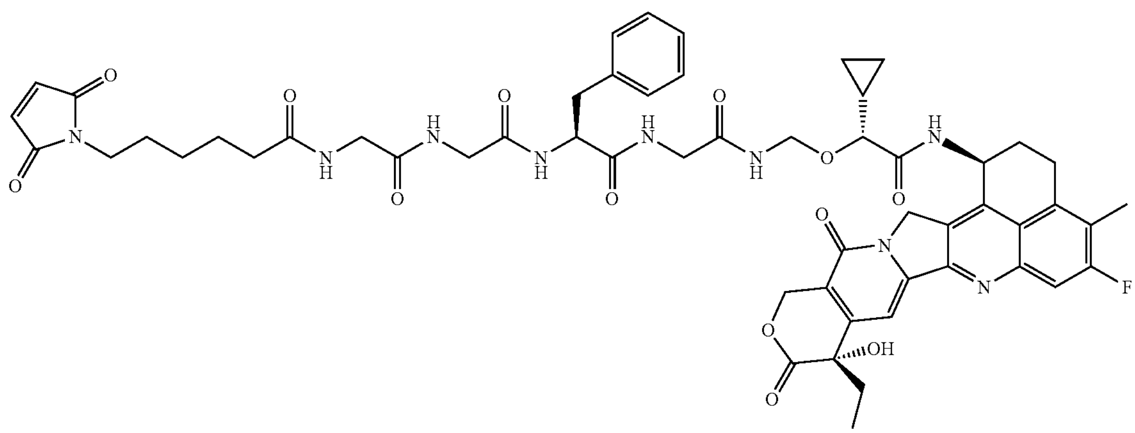

Drug Loading Analysis of ADC Stock Solution

1. UV-HPLC Method

Cuvettes containing a sodium succinate buffer were separately placed into the reference cell and sample cell, and the absorbance value of the solvent blank was subtracted. Then, a cuvette containing the test sample solution was placed into the sample cell, and the absorbance values at 280 nm and 370 nm were determined.

Calculation: the loading in the ADC stock solution was determined by ultraviolet spectrophotometry (instrument: THERMO NANODROP™ 2000 ultraviolet spectrophotometer), based on the principle that the total absorbance value of the ADC stock solution at a certain wavelength was the sum of the absorbance values of the drug and the monoclonal antibody at that wavelength, namely:

$$A_{280\ nm}=\varepsilon_{mab\text{-}280}bC_{mab}+\varepsilon_{Drug\text{-}280}bC_{Drug} \quad (1)$$

$\varepsilon_{Drug\text{-}280}$: the mean molar extinction coefficient of the drug at 280 nm of 5100;

$C_{Drug}$: the concentration of the drug;

$\varepsilon_{mab\text{-}280}$: the mean molar extinction coefficient of the monoclonal antibody stock solution at 280 nm of 214,600;

$C_{mab}$: the concentration of the monoclonal antibody stock solution;

b: the optical path length of 1 cm.

Similarly, an equation for the total absorbance value of the sample at 370 nm can be given as:

$$A_{370\ nm}=\varepsilon_{mab\text{-}370}bC_{mab}+\varepsilon_{Drug\text{-}370}bC_{Drug} \quad (2)$$

$\varepsilon_{Drug\text{-}370}$: the mean molar extinction coefficient of the drug at 370 nm of 19,000;

$C_{Drug}$: the concentration of the drug;

$\varepsilon_{mab\text{-}370}$: the extinction coefficient of the monoclonal antibody at 370 nm of 0;

$C_{mab}$: the concentration of the monoclonal antibody stock solution;

b: the optical path length of 1 cm.

The drug loading can be calculated using both equations (1) and (2) as well as the extinction coefficients of the monoclonal antibody and the drug at both wavelengths and their concentrations.

$$\text{Drug loading}=C_{Drug}/C_{mab}.$$

2. RP-HPLC Method

A naked antibody and a test ADC sample (at concentration 1 mg/mL) were reduced with 4 μL of DDT (SIGMA) in a water bath at 37° C. for 1 h, and then transferred to an insert. Analysis was performed on a high performance liquid chromatograph AGILENT® 1200, with AGILENT® PLRP-S 1000A 8 μm 4.6×250 mm selected as the chromatography column, the column temperature at 80° C., the DAD detector at wavelength 280 nm, the flowrate at 1 mL/min, and the injection volume at 40 μL. Comparisons were made to the spectra of the sample and the naked antibody to identify the locations of the light chain and heavy chain, and then integration was performed on the spectrum of the test sample to calculate the DAR value.

Preparation of Solutions:

1) 0.25 M DTT Solution:

Example of preparation: 5.78 mg of DTT was weighed into 150 μL of purified water and completely dissolved to give 0.25 M DTT solution, which was then stored at −20° C.

2) Mobile Phase A (0.1% TFA in Water):

Example of preparation: 1000 mL of purified water was measured out using a graduated cylinder, and 1 mL of TFA (SIGMA) was added. The solution was well mixed before use and was stored at 2-8° C. for 14 days.

3) Mobile Phase B (0.1% TFA in Acetonitrile):

Example of preparation: 1000 mL of acetonitrile was measured out using a graduated cylinder, and 1 mL of TFA was added. The solution was well mixed before use and was stored at 2-8° C. for 14 days.

Data Analysis:

Comparisons were made to the spectra of the sample and the naked antibody to identify the locations of the light chain and heavy chain, and then integration was performed on the spectrum of the test sample to calculate the DAR value.

The calculation formula is as follows:

TABLE 10

Drug loading marker table for the light chains and heavy chains of ADCs

| Name | Number of linked drugs |
|---|---|
| LC | 0 |
| LC + 1 | 2 |
| HC | 0 |
| HC + 1 | 2 |
| HC + 2 | 4 |
| HC + 3 | 6 |

Total LC peak area=LC peak area+LC+1 peak area;

Total HC peak area=HC peak area+HC+1 peak area+HC+2 peak area+HC+3 peak area;

LC DAR=Σ(number of linked drugs×percent peak area)/total LC peak area;

HC DAR=Σ(number of linked drugs×percent peak area)/total HC peak area; DAR=LC DAR+HC DAR.

Example 1-4: ADC-1/ADC-2

To a PBS buffer containing antibody h1902-5 (0.05 M pH 6.5 PBS buffer; 10.0 mg/mL, 320.0 mL, 21.62 μmol) was added at 37° C. an aqueous solution of tris(2-carboxyethyl) phosphine (TCEP) (10 mM, 11.03 mL, 110.3 μmol). The mixture was reacted on a water bath shaker at 37° C. for 3 h, and then the reaction was terminated. The reaction mixture was cooled to 25° C. in a water bath, and then a solution of compound 9-A (350 mg, 303 mol) in 13.2 mL of acetonitrile and 6.6 mL of DMSO was added to the reaction mixture. The mixture was reacted on a water bath shaker at 25° C. for 3 h, and then the reaction was terminated.

The reaction mixture was purified through an ultrafiltration membrane to remove small molecules. Purification was performed using 5 L of 50 mM pH 6.5 PBS buffer (4% acetonitrile and 2% DMSO) followed by 5 L of 10 mM pH 5.3 succinic acid buffer. Sucrose was then added to the purified solution to 60 mg/mL and Tween-20 to 0.2 mg/mL to prepare ADC-1 (10 mM pH 5.3 succinate buffer; 10 mg/mL, 2.626 g), yield: 81.81%. ADC-1 was then formulated into 20 mg/vial lyophilized powder.

Mean calculated by UV-HPLC: n=6.8.

ADC-2 (n=7.1) could be prepared using the above method with antibody h1901-11 (in place of h1902-5) and compound 9-A.

Example 1-5: ADC-3

To an aqueous PBS buffer containing antibody h1901-11 (0.05 M pH 6.5 aqueous PBS buffer; 10.0 mg/mL, 1 mL, 67.5 nmol) was added at 37° C. a prepared aqueous solution of TCEP (10 mM, 10.1 μL, 101 nmol). The mixture was reacted on a water bath shaker at 37° C. for 3 h, and then the reaction was terminated. The reaction mixture was cooled to 25° C. in a water bath.

Compound 9-A (0.58 mg, 540 nmol) was dissolved in 34 μL of DMSO, and the resulting solution was added to the above reaction mixture. The mixture was reacted on a water bath shaker at 25° C. for 3 h, and then the reaction was terminated. The reaction mixture was desalted and purified through a SEPHADEX™ G25 gel column (elution phase: 0.05 M pH 6.5 aqueous PBS buffer, containing 0.001 M EDTA) to give ADC-3 in a PBS buffer (0.72 mg/mL, 11.2 mL), which was then stored at 4° C. Mean calculated by RP-HPLC: n=2.51.

Example 1-6: ADC-4

To an aqueous PBS buffer containing antibody h1901-11 (0.05 M pH 6.5 aqueous PBS buffer; 10.0 mg/mL, 1 mL, 67.5 nmol) was added at 37° C. a prepared aqueous solution of TCEP (10 mM, 16.9 μL, 169 nmol). The mixture was reacted on a water bath shaker at 37° C. for 3 h, and then the reaction was terminated. The reaction mixture was cooled to 25° C. in a water bath.

Compound 9-A (0.73 mg, 680 nmol) was dissolved in 43 μL of DMSO, and the resulting solution was added to the above reaction mixture. The mixture was reacted on a water bath shaker at 25° C. for 3 h, and then the reaction was terminated. The reaction mixture was desalted and purified through a SEPHADEX™ G25 gel column (elution phase: 0.05 M pH 6.5 aqueous PBS buffer, containing 0.001 M EDTA) to give ADC-4 in a PBS buffer (0.62 mg/mL, 12.5 mL), which was then stored at 4° C. Mean calculated by RP-HPLC: n=4.06.

Example 1-7: ADC-5

To an aqueous PBS buffer of antibody h1901-11 (0.05 M pH 6.5 aqueous PBS buffer; 10.0 mg/mL, 1 mL, 67.5 nmol) was added at 37° C. a prepared aqueous solution of TCEP (10 mM, 35.8 L, 358 nmol). The mixture was reacted on a water bath shaker at 37° C. for 3 h, and then the reaction was terminated. The reaction mixture was cooled to 25° C. in a water bath.

Compound 9-A (1.09 mg, 1015 nmol) was dissolved in 64 μL of DMSO, and the resulting solution was added to the above reaction mixture. The mixture was reacted on a water bath shaker at 25° C. for 3 h, and then the reaction was terminated. The reaction mixture was desalted and purified through a SEPHADEX™ G25 gel column (elution phase: 0.05 M pH 6.5 aqueous PBS buffer, containing 0.001 M EDTA) to give ADC-5 in a PBS buffer (0.54 mg/mL, 12.5 mL), which was then stored at 4° C. Mean calculated by RP-HPLC: n=6.8.

Example 1-8: ADC-6

To an aqueous PBS buffer of antibody h 1902-5 (0.05 M pH 6.5 aqueous PBS buffer; 10.0 mg/mL, 1.08 mL, 72.9 nmol) was added at 37° C. a prepared aqueous solution of TCEP (10 mM, 10.9 μL, 109 nmol). The mixture was reacted on a water bath shaker at 37° C. for 3 h, and then the reaction was terminated. The reaction mixture was cooled to 25° C. in a water bath.

Compound 9-A (0.63 mg, 587 nmol) was dissolved in 40 μL of DMSO, and the resulting solution was added to the above reaction mixture. The mixture was reacted on a water bath shaker at 25° C. for 3 h, and then the reaction was terminated. The reaction mixture was desalted and purified through a SEPHADEX™ G25 gel column (elution phase: 0.05 M pH 6.5 aqueous PBS buffer, containing 0.001 M EDTA) to give ADC-6 in a PBS buffer (0.7 mg/mL, 13.0 mL), which was then stored at 4° C. Mean calculated by RP-HPLC: n=2.69.

Example 1-9: ADC-7

To an aqueous PBS buffer of antibody h1902-5 (0.05 M pH 6.5 aqueous PBS buffer; 10.0 mg/mL, 1.08 mL, 72.9 nmol) was added at 37° C. a prepared aqueous solution of TCEP (10 mM, 18.3 μL, 183 nmol). The mixture was reacted on a water bath shaker at 37° C. for 3 h, and then the reaction was terminated. The reaction mixture was cooled to 25° C. in a water bath.

Compound 9-A (0.79 mg, 736 nmol) was dissolved in 50 μL of DMSO, and the resulting solution was added to the above reaction mixture. The mixture was reacted on a water bath shaker at 25° C. for 3 h, and then the reaction was terminated. The reaction mixture was desalted and purified through a SEPHADEX™ G25 gel column (elution phase: 0.05 M pH 6.5 aqueous PBS buffer, containing 0.001 M EDTA) to give ADC-7 in a PBS buffer (0.6 mg/mL, 14.0 mL), which was then stored at 4° C. Mean calculated by RP-HPLC: n=4.25

Example 1-10: ADC-8

To an aqueous PBS buffer of antibody h 1902-5 (0.05 M pH 6.5 aqueous PBS buffer; 10.0 mg/mL, 1.08 mL, 72.9 nmol) was added at 37° C. a prepared aqueous solution of TCEP (10 mM, 38.7 μL, 387 nmol). The mixture was reacted on a water bath shaker at 37° C. for 3 h, and then the reaction was terminated. The reaction mixture was cooled to 25° C. in a water bath.

Compound 9-A (1.18 mg, 1099 nmol) was dissolved in 70 μL of DMSO, and the resulting solution was added to the above reaction mixture. The mixture was reacted on a water bath shaker at 25° C. for 3 h, and then the reaction was terminated. The reaction mixture was desalted and purified through a SEPHADEX™ G25 gel column (elution phase: 0.05 M pH 6.5 aqueous PBS buffer, containing 0.001 M EDTA) to give ADC-8 in a PBS buffer solution (0.56 mg/mL, 14.2 mL), which was then stored at 4° C. Mean calculated by RP-HPLC: n=7.01.

Example 1-11: ADC-9

To a histidine-acetate-Tris/EDTA buffer (a buffer of 10 mM pH 7.2 histidine-acetate-Tris and 2.5 mM EDTA; 20.6 g/L, 6.49 L, 0.91 mmol) containing antibody h1902-5 was added at 12° C. a prepared TCEP histidine buffer (10 mM histidine buffer; 1.717 mM, 1.16 L, 1.99 mmol). The mixture was stirred in a water bath at a constant temperature of 12° C. for 2 h and then the reaction was terminated to give a solution of intermediate I.

Compound 9-A (4.72 g, 4.39 mmol) was dissolved in 0.38 L of DMSO to give a solution of compound 9-A in DMSO. To the above solution of intermediate I was added 0.38 L of DMSO in advance followed by the solution of compound 9-A in DMSO. The mixture was stirred in a water bath at a constant temperature of 12° C. for 1 h, and then the reaction was terminated.

The reaction mixture was purified through a Capto S Impact cation chromatography column, which was washed with 9 column volumes of 0.05 M acetate buffer containing 10% (v/v) DMSO (pH=5.0) and with 6 column volumes of 0.05 M acetate buffer (pH=5.0), followed by elution with 0.05 M acetic acid and 0.30 M sodium chloride buffer (pH=5.5) to remove free toxins and the residual solvent from the reaction mixture. The cation eluate was subjected to 7-fold volume equal-volume ultrafiltration (polycellulose membrane of 30 KD was used as the ultrafiltration membrane) at 22° C. to give ADC-9 as a product. Mean calculated by RP-HPLC: n=4.1.

Biological Evaluation

Test Example 1: Cell-Level ELISA Binding Assay

Cell-based ELISA assay was used to test the binding properties of the Claudin18.2 antibodies. The stably transfected Claudin18.2-expressing NUGC4 cells were cultured in a 96-well cell plate (CORNING®, 3599). When growing at 90% density, the cells were immobilized with 4% paraformaldehyde for 1 h. The plate was washed 3 times with PBST buffer (pH 7.4 PBS containing 0.05% Tween-20), and a PBS-diluted 5% skim milk (powdered skim milk from Brightdairy) blocking solution was added at 200 μL/well. The plate was incubated in a 37° C. incubator for 2.5 h or was let stand at 4° C. overnight (16-18 h) for blocking. After blocking, the blocking solution was removed. The plate was washed 3 times with the PBST buffer, and then a test antibody that was diluted with a sample diluent (pH 7.4 PBS containing 1% skim milk) to different concentrations was added at 50 μL/well. The plate was incubated in a 37° C. incubator for 2 h. After incubation, the plate was washed 5 times with PBST, and an HRP-labeled goat anti-human secondary antibody (Jackson Immuno Research, 109-035-003) that was diluted with the sample diluent was added at 100 μL/well. The plate was incubated at 37° C. for 1 h. The plate was washed 6 times with PBST, and then TMB chromogenic substrate (KPL, 52-00-03) was added at 50 μL/well. The plate was incubated at room temperature for 10-15 min, and the reaction was terminated by adding 1 M $H_2SO_4$ at 50 μL/well. The absorbance at 450 nm was read using an MD Versa Max™ microplate reader, and the binding EC50 value of the Claudin18.2 antibody to Claudin18.2 was calculated.

TABLE 11

| Binding activity of antibodies | | | |
|---|---|---|---|
| Antibody | IMAB362 | ch1901 | ch1902 |
| Emax | 1.175 | 1.399 | 1.272 |
| EC50 (nM) | 0.108 | 0.098 | 0.074 |

TABLE 12

| Binding activity of humanized antibodies of mAb1901 | | |
|---|---|---|
| Antibody | Emax | EC50 (nM) |
| IMAB362 | 1.115 | 0.086 |
| h1901-2 | 1.039 | 0.076 |
| h1901-3 | 1.1055 | 0.22 |
| h1901-4 | 0.986 | 0.201 |
| h1901-6 | 0.937 | 0.091 |
| h1901-7 | 0.921 | 0.166 |
| h1901-8 | 1.047 | 0.091 |
| h1901-11 | 1.44 | 0.076 |
| h1901-12 | 1.22 | 0.116 |

TABLE 13

| Binding activity of humanized antibodies of mAb1902 | | |
|---|---|---|
| Antibody | Emax | EC50 (nM) |
| IMAB362 | 0.88 | 0.187 |
| h1902-1 | 0.87 | 0.113 |
| h1902-2 | 0.88 | 0.107 |
| h1902-3 | 0.84 | 0.175 |
| h1902-4 | 0.82 | 0.087 |
| h1902-5 | 0.9 | 0.098 |
| h1902-6 | 0.78 | 0.141 |
| h1902-7 | 0.75 | 0.121 |
| h1902-8 | 0.89 | 0.132 |
| h1902-9 | 0.75 | 0.137 |
| h1902-10 | 0.89 | 0.133 |

Test Example 2: Antibody Cell Level Binding Assay

The stably transfected Claudin 18.2-expressing NUGC4 cells were suspended in FACS buffer (2% fetal bovine serum (GIBCO™, 10099141) pH 7.4 PBS (SIGMA, P4417-100TAB)) to obtain a $1\times10^6$/mL cell suspension, which was then added to a 96-well round-bottom plate (CORNING®, 3795) at 100 μL/well. After centrifugation and removal of the supernatant, the test Claudin 18.2 antibody that was diluted with FACS buffer to different concentrations was added at 50 μL/well. The plate was incubated in the dark in a 4° C. refrigerator for 1 h. The plate was washed 3 times with FACS buffer by centrifugation at 300 g, and goat anti-human IgG coated with Alexa Fluor 488 (H+L) (INVITROGEN®, A-11013) at working concentration was added. The plate was incubated in the dark in a 4° C. refrigerator for 40 min. The plate was washed 3 times with FACS buffer by centrifugation at 300 g and tested on a BD FACS CANTOII™ flow cytometer for geometric mean fluorescence intensity. The binding EC50 values of the Claudin18.2 antibodies to the stably transfected Claudin18.2-expressing NUGC4 cells were calculated. The results are shown in FIG. 1.

Test Example 3: Antibody Endocytosis Assay

Figure 2:
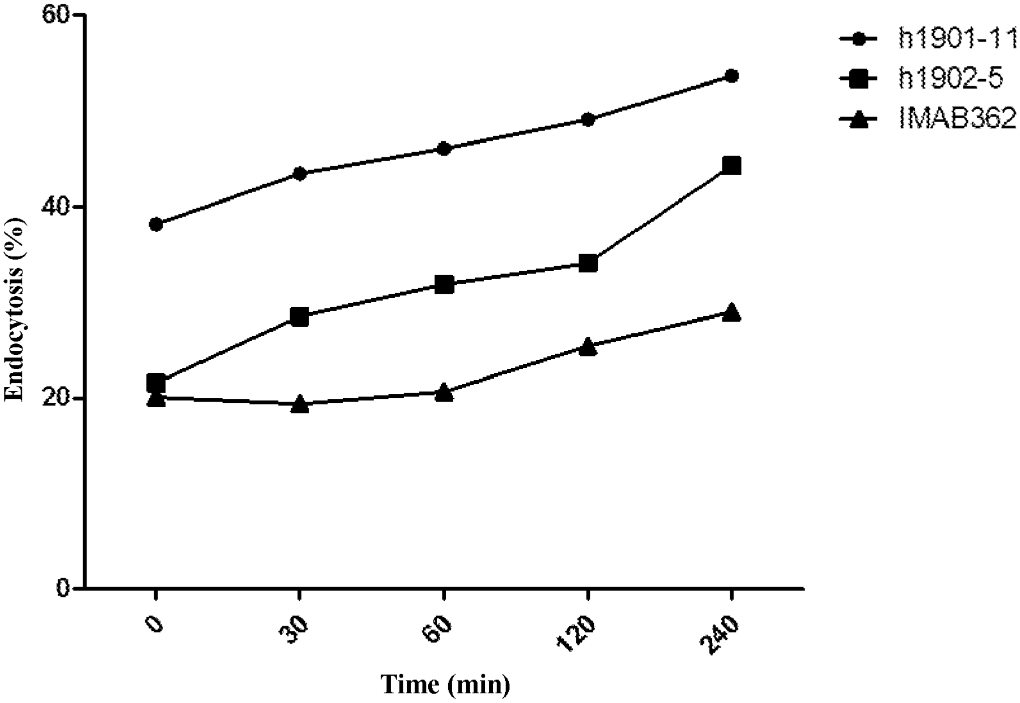
FIG. 2: endocytosis of humanized antibodies by NUGC4 cells.

A test Claudin18.2 antibody pre-labeled with DYLIGHT™ 488 NHS Ester (THERMOFISHER, 46403) was added to $1\times10^6$/mL stably transfected Claudin 18.2-expressing NUGC4 cells at a final concentration of 5 μg/mL. The mixture was incubated in the dark on ice for 1 h and washed 3 times with pre-cooled FACS buffer (pH 7.4 PBS, 2% fetal bovine serum) by centrifugation. After removal of the supernatant, the remainder was added to a pre-heated complete medium, followed by incubation in a 37° C., 5% $CO_2$ cell incubator. The cells were taken out after 0, 0.5, 1, 2 and 4 h and stored in the dark on ice. After all samples were collected, they were each centrifuged at 300 g at low temperature to remove the supernatant. An elution buffer (pH 1.7 0.05 M glycine, 0.1 M sodium chloride) was added, and then the mixture was incubated at room temperature for 7 min, washed once with FACS buffer by centrifugation at 300 g, and tested on a BD FACS CANTOII™ flow cytometer for geometric mean fluorescence intensity. The efficiency of endocytosis of the Claudin18.2 antibodies by the stably transfected Claudin18.2-expressing NUGC4 cells was calculated. The results (see FIG. 2) show that the humanized antibodies have good endocytosis efficiency.

Test Example 4: Antibody Affinity Assay Based on Flow Cytometry

On the day of experiment, HEK293/hClaudin18.2 cells were collected into a U-bottomed 96-well plate at $1\times10^5$ to $2\times10^5$ cells per well. A human Claudin18.2 antibody that was 2× diluted serially (12 concentration points) from an initial concentration of 5 μg/mL was added, and the plate was incubated at 4° C. for 1 h. IMAB362 was used as a positive control, and a negative control with no antibody was also provided. The antibody was removed by centrifugation, and FITC anti-human IgG Fc antibody (200×) was added at 100 μL/well. The plate was incubated in the dark at 4° C. for 30 min and washed twice with PBS+2% FBS before flow cytometry analysis. BD FACS CANTOII™ was started and preheated, and then the BD FACSDiva software was run to start a new experiment. The HEK293/hClaudin18.2 negative control sample was tested, and the FSC and SSC voltages were adjusted to appropriate values and saved. Blank sample B and standard curve 1 were tested according to the instructions for Quantum™ FITC-5 MESF Kit, and the FITC voltage was adjusted to an appropriate value and saved. The samples in the U-bottomed 96-well plate were tested at the saved voltage, and data were recorded. The experimental data were analyzed using Flowjo software to obtain a Geo mean, and an MESF-Geo Mean standard curve was fit according to the instructions for Quantum™ FITC-5 MESF Kit. The molar concentration of the human Claudin18.2 antibody bound to HEK293/hClaudin18.2 cells and the free antibody concentration were calculated according to the concentration fluorescence value of the FITC anti-human IgG Fc antibody, and the Bmax and the dissociation constant KD of the antibody were calculated through Scatchard plots. The results are shown in Table 14.

TABLE 14

| Cell-level affinity of humanized antibodies | | | |
|---|---|---|---|
| Antibody | IMAB362 | h1901-11 | h1902-5 |
| KD (nM) | 10.2 | 6.8 | 1.64 |

Test Example 5. ADCC Effect Evaluation of Antibodies

A variety of NUGC4 cells (expressing Claudin 18.2 at high, moderate and low levels) were digested, centrifuged at 1000 rpm, resuspended, and counted. The cells were resuspended at a density of $3\times10^5$ cells/mL in phenol red-free RPMI 1640 (GIBCO™, 11835-030) supplemented with 10% FBS (New Zealand ultra-low IgG fetal bovine serum, GIBCO™, 1921005PJ). Cells were added to a 96-well plate (CORNING®, 3903) at 25 μL/well (7500 cells/well). An antibody was diluted into the phenol red-free medium to obtain a 3× antibody dilution, which was then added to the cell plate at 25 μL/well. The plate was incubated in a 37° C., 5% $CO_2$ incubator for 0.5 h.

Effector cells (FcrR3A-V158-NFAT-RE-Jurkat cells) were harvested, centrifuged at 1000 rpm, resuspended, and counted. The cells were resuspended at a density of $3\times10^6$ cells/mL in phenol red-free RPMI 1640 supplemented with 10% FBS (New Zealand ultra-low IgG fetal bovine serum), and then were added to the plate at 25 μL/well ($7.5\times10^4$ cells/well). The plate was incubated in a 37° C., 5% $CO_2$ incubator for 6 h.

BRIGHT-GLO™ (PROMEGA™, E2610) was added to the plate at 75 μL/well, and the chemical luminescence was detected using a microplate reader (PerkinElmer, VITOR3).

Figure 3A:
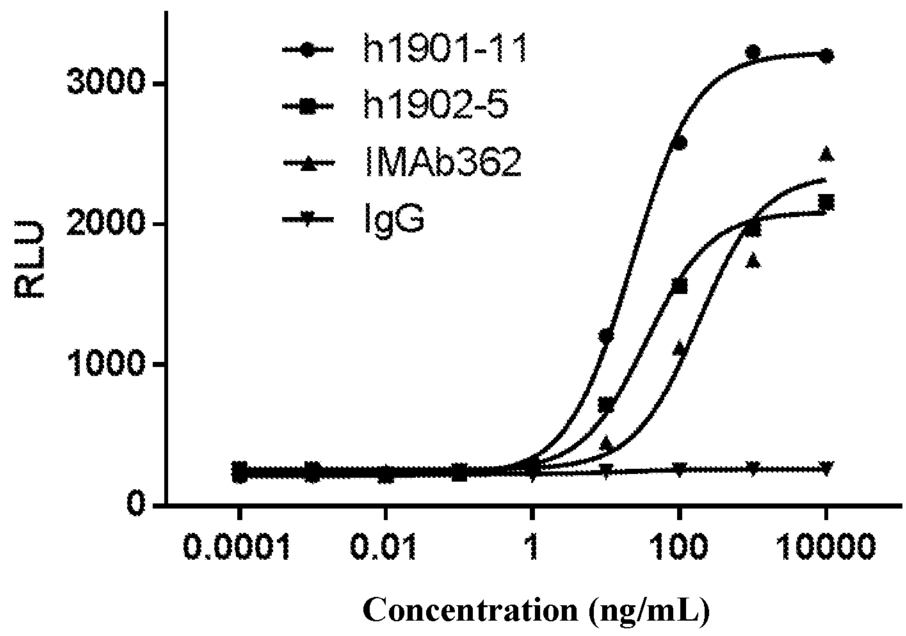
FIGS. 3A to 3C: assays for the ADCC effects of antibodies in NUGC4 cells expressing Claudin18.2 at varying levels.
Figure 3B:
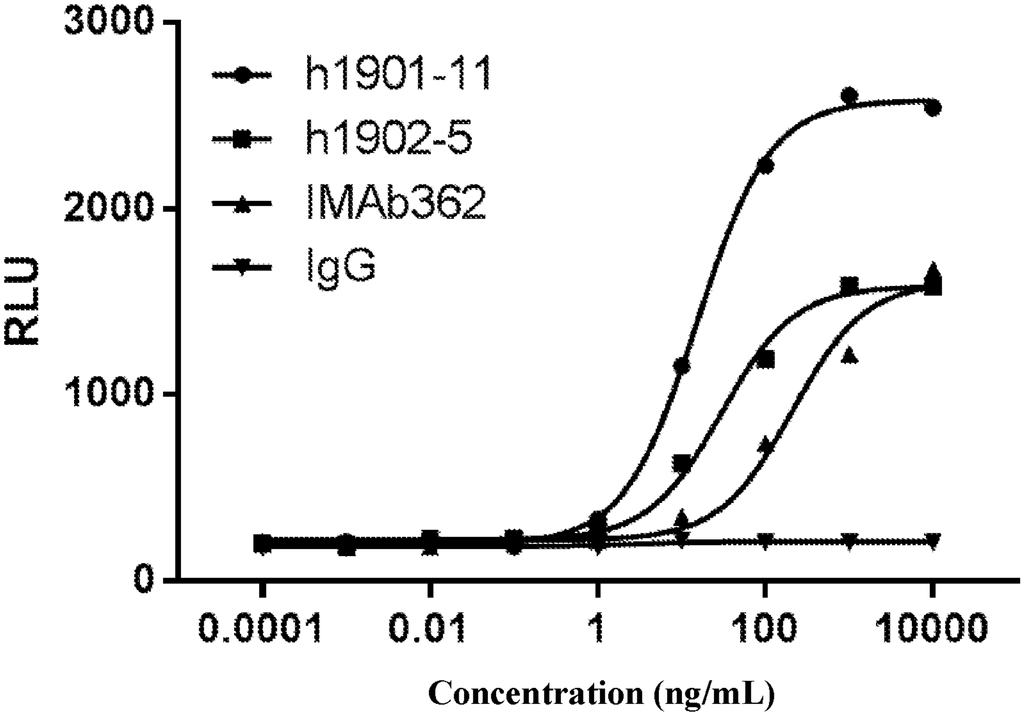
Figure 3C:
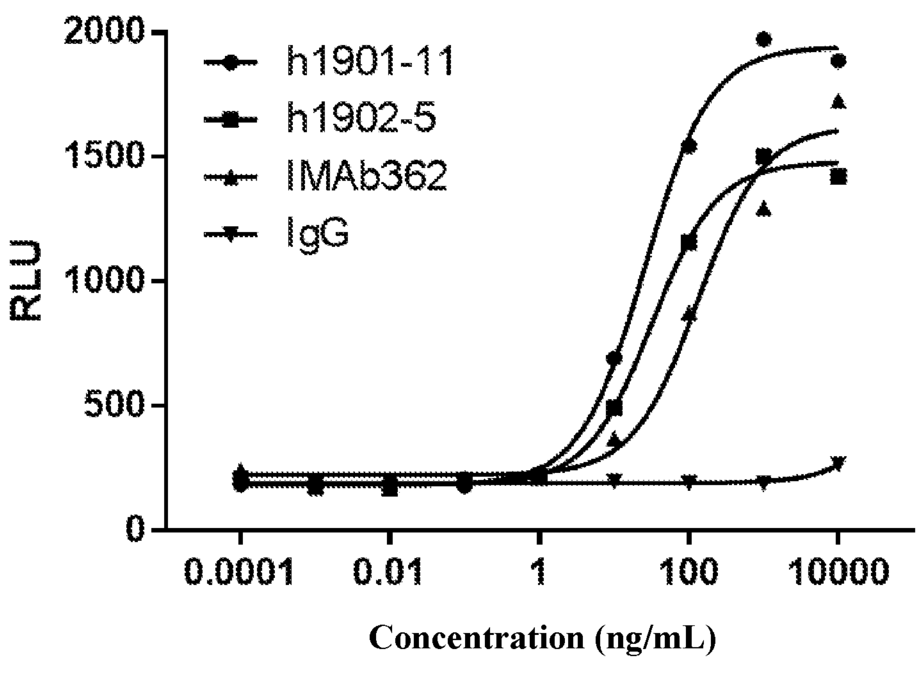

The results (see Table 15 and FIGS. 3A-3C) show that both antibodies h1901-11 and h1902-5 show high ADCC activity in the NUGC4 cells expressing Claudin 18.2 at low levels (FIG. 3A), at moderate levels (FIG. 3B) and at high levels (FIG. 3C).

TABLE 15

ADCC effect of antibodies in NUGC4 cells expressing Claudin18.2 at varying levels Unit IC50 (ng/mL)

| Level of Claudin18.2 expression | h1901-11 | h1902-5 | IMAB362 |
|---|---|---|---|
| Low | 22.42 | 35.46 | 183.4 |
| Moderate | 15.35 | 30.00 | 210.4 |
| High | 26.17 | 32.16 | 132.6 |

Test Example 6: Cell Activity Assay of ADC Molecules

CELLTITER-GLO® luminescence cell viability assays were used to test ADC molecules for the in vitro killing effects on the human gastric cancer cell strain in this experiment. On day 1, NUGC4-claudin 18.2 low expression, NUGC4-claudin 18.2 moderate expression and NUGC4-claudin18.2 high expression cells were harvested, adjusted to density $2.5\times10^4$/mL, and added to a 96-well white transparent plate at 90 μL/well, with about 2500 cells per well. The cells were cultured overnight in a 37° C., 5% $CO_2$ incubator. On day 2, samples were 4× diluted serially from an initial concentration of 5 μM in a U-bottom 96-well plate to obtain 9 concentration points, and the diluted samples were added to the cell plate at 10 μL/well. The cells were cultured at 37° C. with 5% $CO_2$ for 6 days. On day 8, the cell culture plate was taken out, and CELLTITER-GLO® Reagent was added at 50 μL/well. The plate was let stand at room temperature for 2 to 3 min and analyzed on a PHER-Astar FS microplate reader for fluorescence readings. Data analysis was performed using GraphPad Prism software. See Table 16.

TABLE 16

In vitro cell killing experiment of ADCs

| | NUGC4-claudin18.2 low expression cells | | NUGC4-claudin18.2 moderate expression cells | | NUGC4-claudin18.2 high expression cells | |
|---|---|---|---|---|---|---|
| ADC | EC50(nM) | Emax | EC50 (nM) | Emax | EC50(nM) | Emax |
| ADC-1 | 126.8 | 66.7 | 23.6 | 82.1 | 1.3 | 91.5 |
| ADC-2 | 109.0 | 69.8 | 16.8 | 82.3 | 1.9 | 91.1 |
| ADC-3 | >500 | 49.0 | | | 94 | 78.7 |
| ADC-4 | 299 | 61.03 | | | 12 | 84.97 |
| ADC-5 | 142 | 69.91 | | | 3.5 | 95.89 |
| ADC-6 | >500 | 45.22 | | | 11 | 78.00 |
| ADC-7 | 284 | 61.09 | | | 3.9 | 88.51 |
| ADC-8 | 154 | 66.74 | | | 1.3 | 97.15 |

Test Example 7: Evaluation of In Vivo Efficacy of ADC Molecules

Balb/c nude mice were subcutaneously inoculated at the right flank with human gastric cancer cells NUGC4 (expressing Claudin18.2 at moderate levels) cells ($5\times10^6$, containing 50% matrigel/mouse). The mice were divided into a total of 8 groups of 8 on day 0. The mean tumor volume was about 84.41 $mm^3$.

Each mouse was intraperitoneally injected with ADC at 0.1 mL/10 g body weight on days 0, 4 and 11, making a total of 3 injections.

Each mouse was intraperitoneally injected with ADC at 0.1 mL/10 g body weight from the day of grouping at intervals of 5 days, and a total of 4 injections were given.

The tumor volumes and body weights were measured twice a week and the results were recorded.

Excel 2003 statistical software was used. The mean values were calculated as avg; the SD values were calculated as STDEV; the SEM values were calculated as STDEV/SQRT; and the inter-group difference P-value was calculated as TTEST.

Tumor volume (V) was calculated as: $V=\frac{1}{2}\times L_{long}\times L_{short}^2$ Relative volume (RTV)=VT/V0

Figure 4:
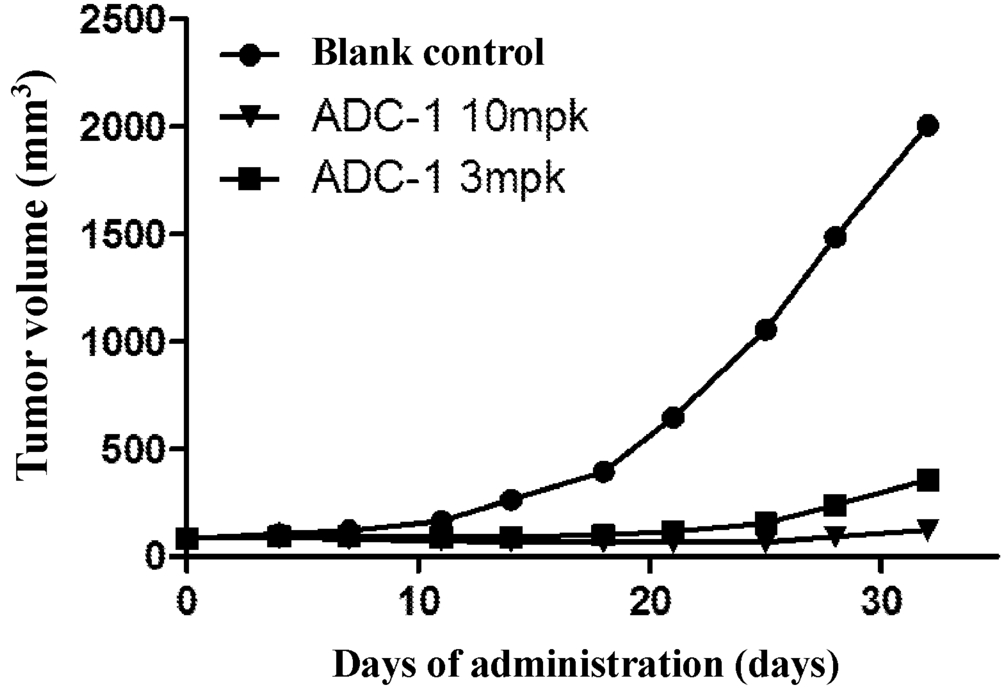
FIG. 4: the results of inhibition of tumors by ADC-1 of the present disclosure.
Figure 5:
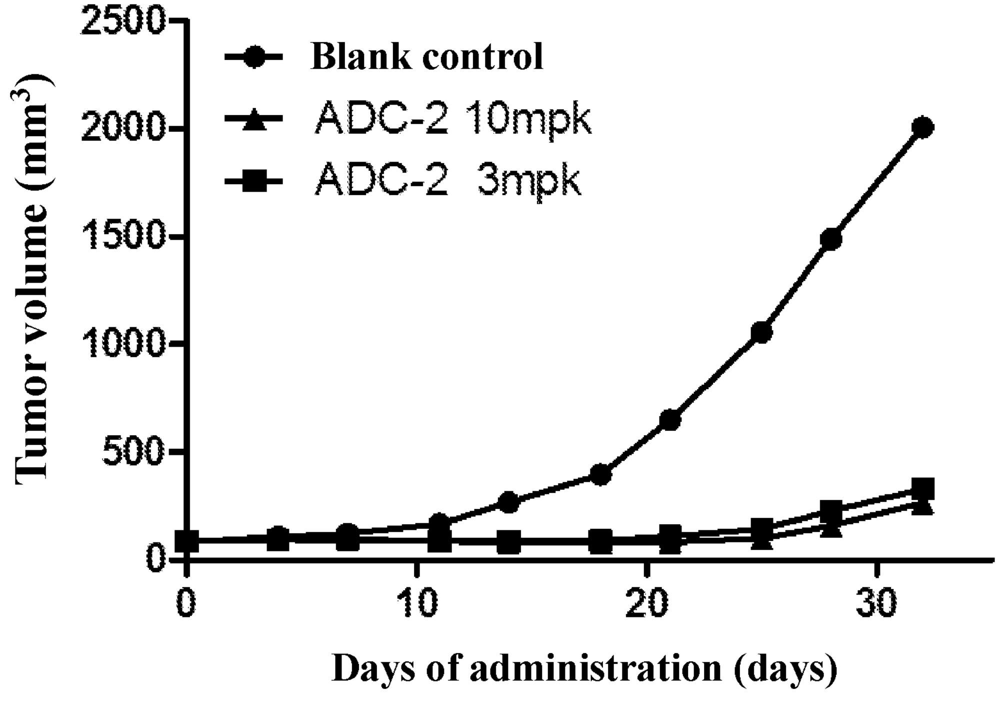
FIG. 5: the results of inhibition of tumors by ADC-2 of the present disclosure.

Tumor inhibition rate (%)=(CRTV−TRTV)/CRTV (%)

where V0 and VT are the tumor volume at the beginning of the experiment (the day of first administration is defined as day 0) and the tumor volume at the end of the experiment, respectively; CRTV and TRTV are the relative tumor volumes of the blank control group (Vehicle) and the experimental groups, respectively, at the end of the experiment. The results are shown in Table 17 and FIGS. 4 and 5.

TABLE 17

Results of inhibition of tumors by ADCs

| | Mean tumor volume ($mm^3$) | | Mean tumor volume ($mm^3$) | | Relative tumor volume | | % tumor inhibition |
|---|---|---|---|---|---|---|---|
| Group | D 0 | SEM | D 32 | SEM | D 0 | SEM | rate D 32 |
| Blank control group | 83.33 | 0.82 | 2067.0 | 102.24 | 24.83 | 1.27 | — |
| ADC-2 10 mpk | 83.93 | 1.65 | 263.13 | 44.17 | 3.11 | 0.51 | 87.47%** |
| ADC-2 3 mpk | 84.35 | 1.83 | 328.95 | 45.04 | 3.86 | 0.48 | 84.45%** |
| ADC-1 10 mpk | 83.60 | 1.61 | 123.80 | 20.99 | 1.48 | 0.25 | 94.04%** |
| ADC-1 3 mpk | 86.84 | 1.91 | 356.41 | 55.18 | 4.06 | 0.58 | 83.65%** |

vs. blank control group:
**$p < 0.01$.

II. Formulation

The Equipment Used in the Formulation Preparation and Determination and the Calculation Method for Results are Shown Below.

SEC molecular exclusion chromatography:

This is a method for analyzing the separation of a solute by the relative relationship between the pore size of the gel pores and the size of the polymer sample molecule coil.

SEC % (SEC monomer content percentage)=A monomer/A total×100% (A monomer represents the peak area of the main peak monomer in the sample, and A total represents the sum of all peak areas).

Instrument for SEC determination: Agilent 1260; column: WATERS™, XBrige BEH200 Å SEC (300×7.8 mm 3.5 μm).

CE Capillary Gel Electrophoresis:

This is a method of moving the gel into a capillary as a supporting medium for electrophoresis and separating according to the molecular weight of the sample under a certain voltage.

Reduced CE purity percentage=A main peak/A total×100% (A main peak represents the light chain main peak area+the heavy chain main peak area, and A total represents the sum of all peak areas).

Instrument for CE determination: BECKMAN®, model: plus800.

Osmotic Pressure Measurement:

The freezing point method was used for measuring the osmotic pressure. The freezing point of a solution is measured by using a high-sensitivity temperature-sensing element on the basis of the proportional relation between the freezing point depression value and the molar concentration of the solution, and then converted into the osmotic pressure through electric quantity. Manufacturer of instrument: LÖSER, model: OM815.

Protein Concentration Determination:

Because the drug in the antibody drug conjugate absorbed light at 280 nm, the protein concentration was corrected using the following formulas:

$$A280=Cd\times\varepsilon 280d+Cmab\times\varepsilon 280mab;$$

$$A370=Cd\times\varepsilon 370d;$$

where Cd represents the concentration of the drug, Cmab represents the concentration of the protein, ε280d represents the extinction coefficient of the drug at 280 nm, ε280 mab represents the extinction coefficient of the protein at 280 nm, and ε370d represents the extinction coefficient of the drug at 370 nm. ε280 mab=1.49 mg−1*cm−1*mL, ε280d=5000 (molar extinction coefficient of drug at 280 nm)/1074.13 (molecular weight of drug)=4.65 mg−1*cm−1*mL, 8370d=19000 (molar extinction coefficient of drug at 370 nm)/1074.13 (molecular weight of drug)=17.69 mg−1*cm−1*mL, where the above extinction coefficients are mass extinction coefficients.

Instrument for protein concentration measurement: ultraviolet-visible spectrophotometer; model: NANODROP™ oneC; optical path length: 1 mm.

Example 2-1: Formulations' Buffer System and pH Value Screening

Formulations containing 20 mg/mL (protein concentration) ADC-9 and the following different buffer systems, as well as 0.1 mg/mL polysorbate 80 (PS80), were prepared.

1) 10 mM citric acid-sodium citrate (CA), pH 5.5
2) 10 mM succinic acid-sodium succinate (SA), pH 5.0
3) 10 mM succinic acid-sodium succinate, pH 5.5
4) 10 mM histidine hydrochloride (His-HCl), pH 5.5
5) 10 mM histidine hydrochloride, pH 6.0
6) 10 mM histidine hydrochloride, pH 6.5
7) 10 mM histidine-acetate (His-AA), pH 5.0
8) 10 mM histidine-acetate, pH 5.5
9) 10 mM phosphate (PB), pH 6.5.

Each of the formulations was filtered, bottled, stoppered and capped. Samples were taken for high-temperature stability (40° C.) tests and shaking (25° C., 300 rpm) tests and examined for appearance, SEC and reduced CE. The results are shown in Table 18.

After 11 days of shaking, only samples 2), 3), 7) and 9) were clear in appearance. After 15 days of storage at 40° C., samples 1), 2), 3), 7) and 8) were clear in appearance. That is, samples 2), 3) and 7) were better in terms of appearance. After 15 days of sitting at 40° C., the samples were analyzed by SEC, and the results show that samples 4), 5), 6), 7) and 8) saw decreases of about 4% in monomer, and the other formulations saw decreases of 7-10% in monomer.

After 15 days of sitting at 40° C., the samples were analyzed by reduced CE, and the results show that samples 4), 5), 7) and 8) saw decreases of about 1-2% in main peak, better than the other samples.

According to the above results, sample 7), namely the 10 mM pH 5.0 His-AA formulation, was better than the other formulations in terms of appearance and performance in these chemical assays, and 10 mM pH 5.0 His-AA was therefore selected as the final buffer.

TABLE 18

| pH and buffers' stability results | | | | | | | |
|---|---|---|---|---|---|---|---|
| No. | Buffer solution and pH | Conditions of sitting | Appearance | SEC % Monomer | Δmonomer | Reduced CE % | Δmain peak |
| 1 | 10 mM CA, pH 5.5 | D 0 | Clear | 94.4 | N/A | 98.5 | N/A |
| | | Shaking D 11 | Clear, occasional particles | 92.0 | −2.4 | 98.6 | 0.1 |
| | | 40° C. D 15 | Clear | 83.5 | −10.9 | 94.5 | −4.0 |
| 2 | 10 mM SA, pH 5.0 | D 0 | Clear | 95.1 | N/A | 98.4 | N/A |
| | | Shaking D 11 | Clear | 93.7 | −1.4 | 98.8 | 0.5 |
| | | 40° C. D 15 | Clear | 87.7 | −7.4 | 94.0 | −4.3 |
| 3 | 10 mM SA, pH 5.5 | D 0 | Clear | 94.4 | N/A | 98.1 | N/A |
| | | Shaking D 11 | Clear | 92.3 | −2.1 | 98.4 | 0.3 |
| | | 40° C. D 15 | Clear | 87.2 | −7.2 | 94.9 | −3.1 |
| 4 | 10 mM His-HCl, pH 5.5 | D 0 | Slightly opalescent | 94.6 | N/A | 98.2 | N/A |
| | | Shaking D 11 | Slightly opalescent, containing particles+ | 93.9 | −0.7 | 97.7 | −0.5 |
| | | 40° C. D 15 | Clear, occasional particles | 90.7 | −3.9 | 96.9 | −1.2 |
| 5 | 10 mM His-HCl, pH 6.0 | D 0 | Clear | 94.1 | N/A | 98.0 | N/A |
| | | Shaking D 11 | Fine particles+++ | 92.8 | −1.3 | 97.1 | −0.8 |
| | | 40° C. D 15 | Small amounts of fine particles | 90.1 | −4.1 | 96.3 | −1.6 |
| 6 | 10 mM His-HCl, pH 6.5 | D 0 | Opalescent | 93.5 | N/A | 98.2 | N/A |
| | | Shaking D 11 | Opalescent++, fine particles+++ | 91.5 | −2.0 | 96.3 | −1.9 |
| | | 40° C. D 15 | Particles settled to bottom | 88.8 | −4.7 | 94.7 | −3.5 |
| 7 | 10 mM His-AA, pH 5.0 | D 0 | Clear | 95.5 | N/A | 98.4 | N/A |
| | | Shaking D 11 | Clear | 95.2 | −0.4 | 99.0 | 0.6 |
| | | 40° C. D 15 | Clear | 91.6 | −4.0 | 96.4 | −2.0 |
| 8 | 10 mM His-AA, pH 5.5 | D 0 | Slightly opalescent | 94.8 | N/A | 98.4 | N/A |
| | | Shaking D 11 | Clear, occasional particles | 93.8 | −1.0 | 98.3 | −0.1 |
| | | 40° C. D 15 | Clear | 90.9 | −3.9 | 96.6 | −1.8 |
| 9 | 10 mM PB, pH 6.5 | D 0 | Clear | 91.9 | N/A | 97.4 | N/A |
| | | Shaking D 11 | Clear | 87.2 | −4.7 | 98.0 | 0.6 |
| | | 40° C. D 15 | Small amounts of fine particles | 83.6 | −8.3 | 93.7 | −3.7 |

Note:
in the table, "D" indicates day; for example, D 3 indicates 3 days, and so on; D 0 indicates the start of the experiment; the same applies below.

Example 2-2: Surfactant Type and Concentration Screening

Formulations containing different types and concentrations of polysorbate and containing 10 mM pH 5.0 His-AA buffer, 80 mg/mL sucrose and ADC-9 at a protein concentration of 20 mg/mL were prepared. Each of the formulations was filtered, bottled, stoppered and capped. Samples were taken for high-temperature stability tests (40° C.) and freeze-thaw tests. The freeze-thaw tests were performed by 5 freeze-thaw cycles (FT5C, 35° C.-2 to 8° C.) followed by three days of sitting at room temperature (25° C. D3). The samples were examined for appearance, SEC and reduced CE. See Table 19 for details about formulation designs.

The results are shown in Table 20 and show that the formulation containing 0.2 mg/mL PS80 had the best appearance and performance in the chemical assays under these conditions.

According to the above results, 0.2 mg/mL PS80 was selected as the surfactant type and concentration.

TABLE 19

| Formulations for polysorbate type and concentration screening | | | |
|---|---|---|---|
| Dosage form | Polysorbate | Buffer | ADC protein concentration |
| Solution formulation | PS80 0.2 mg/mL | 10 mM His-AA, | 20 mg/mL |
| | PS80 0.4 mg/mL | pH 5.0 + | |
| | PS20 0.2 mg/mL | 80 mg/mL | |
| | PS20 0.4 mg/mL | sucrose | |

Note:
PS20 represents polysorbate 20.

Note: PS20 represents polvsorbate 20.

TABLE 20

| Polysorbate type screening results | | | | |
|---|---|---|---|---|
| Polysorbate type | Conditions | Appearance | SEC % | Reduced CE % |
| PS80 0.2 mg/mL | D 0 | Clear | 95.5 | 98.6 |
| | FT5C + 25° C. D 3 | Clear | 95.8 | 97.9 |
| | 40° C. M 1 | Clear | 89.2 | 93.4 |
| PS80 0.4 mg/mL | D 0 | Clear | 95.5 | 98.3 |
| | FT5C + 25° C. D 3 | Small amounts of haze-like particles | 95.8 | 98.6 |
| | 40° C. M 1 | Fine particles | 86.4 | 89.9 |
| PS20 0.2 mg/mL | D 0 | Clear | 95.7 | 98.1 |
| | FT5C + 25° C. D 3 | Small amounts of haze-like particles | 95.9 | 98.2 |
| | 40° C. M 1 | Fine particles | 88.4 | 91.7 |

TABLE 20-continued

| Polysorbate type screening results | | | | |
|---|---|---|---|---|
| Polysorbate type | Conditions | Appearance | SEC % | Reduced CE % |
| PS20 | D 0 | Clear | 95.7 | 98.6 |
| 0.4 mg/mL | FT5C + 25° C. D 3 | Clear | 95.5 | 97.0 |
| | 40° C. M 1 | Particles settled to bottom | 89.6 | 92.9 |

Note:
in the table, "M" indicates month, M 1 indicates 1 month, and so on, and the same applies below.

Example 2-3: Sugar Type Screening

Formulations containing sucrose, trehalose, mannitol and also containing 10 mM His-AA (pH 5.0) buffer, 0.2 mg/mL PS80 and 20 mg/mL (protein concentration) ADC-9 were prepared. Each of the formulations was filtered, bottled, stoppered and capped. Samples were taken for high-temperature stability tests (40° C.) and tests of −35° C./4° C. freeze-thaw cycles followed by sitting at room temperature for 3 days, and were examined for appearance, SEC and reduced CE.

The results are shown in Table 21. When the formulations containing different types of sugar were under freeze-thaw conditions, the sample with sucrose has a better appearance than the sample with trehalose or mannitol. The SEC assay results show that the sample with sucrose or trehalose was better than the sample with mannitol; after one month of sitting at 40° C., the sample with sucrose had a better appearance than the sample with trehalose or mannitol. The SEC and reduced CE results also show that the sample with sucrose was slightly better than the sample with trehalose.

TABLE 21

| Sugar type solution formulation screening results | | | | |
|---|---|---|---|---|
| Sugar concentration | Conditions | Appearance | SEC % | Reduced CE % |
| 80 mg/mL | D 0 | Clear | 95.5 | 98.6 |
| sucrose | FT5C + 25° C. D 3 | Clear | 95.8 | 97.9 |
| | 40° C. M 1 | Clear | 89.2 | 93.4 |
| 80 mg/mL | D 0 | Clear | 95.5 | 97.7 |
| trehalose | FT5C + 25° C. D 3 | Clear | 95.2 | 98.0 |
| | 40° C. M 1 | Fine particles | 88.0 | 91.8 |
| 50 mg/mL | D 0 | Clear | 95.0 | 98.6 |
| mannitol | FT5C + 25° C. D 3 | Small amounts of haze-like particles | 89.5 | 98.6 |
| | 40° C. M 1 | Fine particles | 88.4 | 92.9 |

Formulations containing sucrose, trehalose, mannitol and also containing 10 mM His-AA (pH 5.0) buffer, 0.2 mg/mL PS80 and 20 mg/mL (protein concentration) ADC-9 were prepared. Each of the formulations was filtered, bottled, half-stoppered, lyophilized, stoppered, capped, placed in a high-temperature environment (40° C.) to test its stability, and examined for appearance, SEC and reduced CE. See lyophilization process parameters 1 of table 22 for the lyophilization process.

TABLE 22

| Lyophilization process parameters 1 | | | | |
|---|---|---|---|---|
| Lyophilization process parameter | Set temperature (° C.) | Set time (min) | Holding time (h) | Degree of vacuum (Pa) |
| Pre-freezing | 5 | 10 | 1 | N/A |
| Pre-freezing | −45 | 50 | 2.5 | N/A |
| Primary drying | −20 | 120 | 45 | 20 |
| Secondary drying | 25 | 60 | 8 | 1 |

After one month of sitting at 40° C., the SEC results (see Table 23) show that the sample with sucrose was slightly better than the sample with trehalose and was better than the sample with mannitol. The reduced CE results (see Table 23) show that the sample with sucrose was comparable to the sample with trehalose and was better than the sample with mannitol.

TABLE 23

| Sugar type lyophilizate screening results | | | |
|---|---|---|---|
| Sugar concentration | Conditions of sitting | SEC % | Reduced CE % |
| 80 mg/mL | Before lyophilization | 96.2 | 98.8 |
| sucrose | 40° C. M 1 | 95.9 | 98.63 |
| 80 mg/mL | Before lyophilization | 96.1 | 98.76 |
| trehalose | 40° C. M 1 | 95.1 | 98.89 |
| 50 mg/mL | Before lyophilization | 96.0 | 98.79 |
| mannitol | 40° C. M 1 | 89.9 | 97.37 |

Example 2-4: Experiments for Optimizing Appearance of Lyophilized Samples

A stock solution was prepared according to 10 mM pH 5.0 His-AA, 80 mg/mL sucrose, 0.2 mg/mL PS80 and 20 mg/mL (protein concentration) ADC-9, and was filtered, bottled and then lyophilized according to the lyophilization process parameters 1 (see Table 22). The lyophilized sample was examined for appearance. The lyophilized sample was a white powder cake with a flat surface, but the edge of the bottom of the powder cake slightly contracted.

The sugar concentration of the sample was further reduced to 60 mg/mL. A stock solution was prepared according to 10 mM pH 5.0 His-AA, 60 mg/mL sucrose, 0.2 mg/mL PS80 and 20 mg/mL (protein concentration) ADC-9, and was filtered, bottled and then lyophilized according to the lyophilization process parameters 1 (see Table 22). After lyophilization, the surface of the powder cake was flat and free of wrinkles, and the edge of the bottom of the powder cake slightly contracted.

The sugar concentration was reduced to 40 mg/mL, but at this concentration, the finished product had an overly low osmotic pressure; there is a risk of low osmotic pressure in clinical administration. To ensure the osmotic pressure of the finished product, the ionic strength of the buffer was raised to 30 mM. A stock solution was prepared according to 30 mM pH 5.0 His-AA, 40 mg/mL sucrose, 0.2 mg/mL PS80 and 20 mg/mL (protein concentration) ADC-9, and was filtered, bottled and then lyophilized according to the lyophilization process parameters 1. After lyophilization, the surface of the powder cake was flat and did not sink, and the edge of the bottom of the powder cake was complete.

The results for the three formulations are shown in Table 24.

TABLE 24

| Appearances of lyophilized samples | |
|---|---|
| Formulation | Appearance after lyophilization |
| 10 mM pH 5.0 His-AA, 80 mg/mL sucrose, 0.2 mg/mL PS80, and 20 mg/mL (protein concentration) ADC-9 | The surface of the powder cake was flat, and the edge of the bottom contracted |
| 10 mM pH 5.0 His-AA, 60 mg/mL sucrose, 0.2 mg/mL PS80, and 20 mg/mL (protein concentration) ADC-9 | The surface of the powder cake was flat, and the edge of the bottom slightly contracted |
| 30 mM pH 5.0 His-AA, 40 mg/mL sucrose, 0.2 mg/mL PS80, and 20 mg/mL (protein concentration) ADC-9 | The surface of the powder cake was flat, and the edge of the bottom was complete |

Example 2-5: Stability of Lyophilized Samples

Stock solutions were prepared according to the formulations in Table 25, and were filtered, bottled and then lyophilized according to lyophilization process parameters 1 (see table 22). The lyophilized samples were let stand under 40° C. MI conditions and then reconstituted, and changes in their stability were detected.

The stability results are shown in Table 25 and show that the lyophilized sample of formulation 3 saw a decrease of about 3.7% in reduced CE under 40° C. M1 conditions, and that the other two formulations saw no significant change in each chemical assay; they had significantly better stability than formulation 3. Before lyophilization, the stock solution of formulation 2 had a pH of 5.04. After lyophilization, the reconstituted solution had a pH of 5.27.

TABLE 25

| Stability results for formulations | | | | | |
|---|---|---|---|---|---|
| No. | Formulation | Conditions of sitting | SEC % monomer | Reduced CE % | Appearance after reconstitution |
| 1 | 10 mM pH 5.0 His-AA, 80 mg/mL sucrose, 0.2 mg/mL PS80, and 20 mg/mL (protein concentration) ADC-9 | Before lyophilization | 96.2 | 98.8 | N/A |
| | | Reconstitution after lyophilization | 96.0 | 98.3 | Clear |
| | | 40° C. M 1 | 95.9 | 98.6 | N/A |
| 2 | 30 mM pH 5.0 His-AA, 40 mg/mL sucrose, 0.2 mg/mL PS80, and 20 mg/mL (protein concentration) ADC-9 | Before lyophilization | 98.2 | 98.8 | N/A |
| | | Reconstitution after lyophilization | N/A | N/A | Clear |
| | | 40° C. M 1 | 98.0 | 98.3 | N/A |
| 3 | 10 mM pH 5.0 SA, 80 mg/mL sucrose, 0.4 mg/mL PS80, and 20 mg/mL (protein concentration) ADC-9 | Before lyophilization | 95.3 | 98.73 | N/A |
| | | Reconstitution after lyophilization | 95.3 | 98.29 | Clear |
| | | 40° C. M 1 | 95.1 | 95.06 | N/A |

Example 2-6: Stability of Solution Formulations of Lyophilized Formulations

Formulations were prepared according to the formulations in Table 26, and were filtered, bottled, stoppered, capped and subjected to tests of −35° C./4° C. freeze-thaw cycles followed by sitting at room temperature for 3 days, 11-day shaking tests and high-temperature stability tests (40° C.). The samples were examined under corresponding conditions for changes in appearance, SEC and reduced CE.

The stability results are shown in Table 26 and show that after the sucrose concentration was reduced and the ionic strength of the buffer was raised, there was no significant difference in changes in appearance and purity between formulation 2 and formulation 1, and that under high-temperature conditions, formulation 2 saw a slightly better decrease in reduced CE than formulation 1.

TABLE 26

| Stability results for formulations | | | | | |
|---|---|---|---|---|---|
| No. | Formulation | Conditions of sitting | Appearance | SEC % | Reduced CE % |
| 1 | 10 mM pH 5.0 His-AA, 80 mg/mL sucrose, 0.2 mg/mL PS80, and 20 mg/mL (protein concentration) ADC-9 | D0 | Clear | 95.5 | 98.6 |
| | | FT5C + 25° C. D 3 | Clear | 95.8 | 97.9 |
| | | Shaking D 11 | Clear | 95.1 | 98.5 |
| | | 40° C. M 1 | Clear | 89.2 | 93.4 |

TABLE 26-continued

| Stability results for formulations | | | | | |
|---|---|---|---|---|---|
| No. | Formulation | Conditions of sitting | Appearance | SEC % | Reduced CE % |
| 2 | 30 mM pH 5.0 His-AA, 40 mg/mL sucrose, 0.2 mg/mL PS80, and 20 mg/mL (protein concentration) ADC-9 | D0 | Clear | 97.4 | 98.7 |
| | | FT5C + 25° C. D 3 | Clear | 97.3 | 98.6 |
| | | Shaking D 11 | Clear | 97.9 | 98.7 |
| | | 40° C. M 1 | Clear | 92.4 | 96.2 |

The invention claimed is:

1. A pharmaceutical composition, comprising an anti-Claudin18.2 antibody drug conjugate and a buffer, wherein an anti-Claudin18.2 antibody in the anti-Claudin 18.2 antibody drug conjugate comprises a heavy chain variable region and a light chain variable region, wherein:

i) the heavy chain variable region comprises HCDR1, HCDR2 and HCDR3 having amino acid sequences identical to those of a heavy chain variable region set forth in SEQ ID NO: 5, and the light chain variable region comprises LCDR1, LCDR2 and LCDR3 having amino acid sequences identical to those of a light chain variable region set forth in SEQ ID NO: 6; or il) the heavy chain variable region comprises HCDR1, HCDR2 and HCDR3 having amino acid sequences identical to those of a heavy chain variable region set forth in SEQ ID NO: 3, and the light chain variable region comprises LCDR1, LCDR2 and LCDR3 having amino acid sequences identical to those of a light chain variable region set forth in SEQ ID NO: 4;

the buffer is a histidine salt buffer.

2. The pharmaceutical composition according to claim 1, wherein the anti-Claudin 18.2 antibody comprises a heavy chain variable region and a light chain variable region, wherein:

iii) the heavy chain variable region comprises HCDR1, HCDR2 and HCDR3 set forth in SEQ ID NO: 15, SEQ ID NO: 16 and SEQ ID NO: 17, respectively, and the light chain variable region comprises LCDR1, LCDR2 and LCDR3 set forth in SEQ ID NO: 18, SEQ ID NO: 19 and SEQ ID NO: 20, respectively; or iv) the heavy chain variable region comprises HCDR1, HCDR2 and HCDR3 set forth in SEQ ID NO: 9, SEQ ID NO: 10 and SEQ ID NO: 11, respectively, and the light chain variable region comprises LCDR1, LCDR2 and LCDR3 set forth in SEQ ID NO: 12, SEQ ID NO: 13 and SEQ ID NO: 14, respectively.

3. The pharmaceutical composition according to claim 1, wherein the anti-Claudin18.2 antibody drug conjugate has a structure of general formula (Pc-L-Y-D):

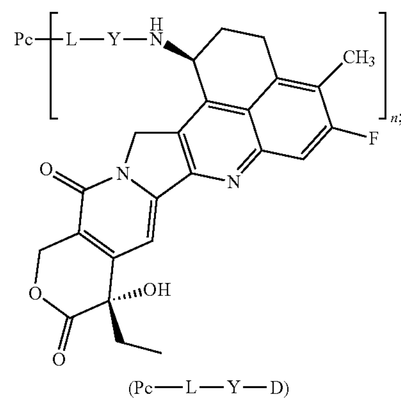

(Pc—L—Y—D)

wherein:

Y is selected from the group consisting of —O—$(CR^aR^b)_m$—$CR^1R^2$—C(O)—, —O—$CR^1R^2$—$(CR^aR^b)_m$—, —O—$CR^1R^2$—, —NH—$(CR^aR^b)_m$—$CR^1R^2$—C(O)— and —S—$(CR^aR^b)_m$—$CR^1R^2$—C(O)—;

$R^a$ and $R^b$ are identical or different and are each independently selected from the group consisting of hydrogen, deuterium, halogen, alkyl, haloalkyl, deuterated alkyl, alkoxy, hydroxy, amino, cyano, nitro, hydroxyalkyl, cycloalkyl and heterocyclyl;

or, $R^a$ and $R^b$, together with the carbon atom to which they are attached, form cycloalkyl or heterocyclyl;

$R^1$ is selected from the group consisting of halogen, haloalkyl, deuterated alkyl, cycloalkyl, cycloalkylalkyl, alkoxyalkyl, heterocyclyl, aryl and heteroaryl;

$R^2$ is selected from the group consisting of hydrogen, halogen, haloalkyl, deuterated alkyl, cycloalkyl, cycloalkylalkyl, alkoxyalkyl, heterocyclyl, aryl and heteroaryl;

or, $R^1$ and $R^2$, together with the carbon atom to which they are attached, form cycloalkyl or heterocyclyl;

or, $R^a$ and $R^2$, together with the carbon atom to which they are attached, form cycloalkyl or heterocyclyl;

m is an integer from 0 to 4;

n is a decimal or an integer from 1 to 10;

L is a linker unit;

Pc is an anti-Claudin18.2 antibody.

4. The pharmaceutical composition according to claim 1, wherein the pharmaceutical composition further comprises a surfactant which is polysorbate.

5. The pharmaceutical composition according to claim 4, wherein the surfactant is at a concentration of 0.05 mg/ml to 0.5 mg/mL.

6. The pharmaceutical composition according to claim 1, wherein the composition further comprises a sugar selected from the group consisting of sucrose, mannitol and trehalose.

7. The pharmaceutical composition according to claim 6, wherein the sugar is at a concentration of 20 mg/mL to 100 mg/mL.

8. The pharmaceutical composition according to claim 1, wherein the anti-Claudin 18.2 antibody drug conjugate is at a protein concentration of 1 mg/mL to 100 mg/mL.

9. The pharmaceutical composition according to claim 1, wherein the buffer is at a concentration of 5 mM to 50 mM.

10. The pharmaceutical composition according to claim 1, wherein the pharmaceutical composition has a pH of 5.0-6.5.

11. The pharmaceutical composition according to claim 1, comprising the following components:

(a) the anti-Claudin18.2 antibody drug conjugate at a protein concentration of 10 mg/mL to 30 mg/mL, (b) 0.1 mg/ml to 0.2 mg/mL polysorbate, (c) 40 mg/ml to 80 mg/ml sugar, and (d) 10 mM to 30 mM histidine salt buffer; the pharmaceutical composition having a pH of 5.0-5.5.

16. An article of manufacture, comprising a container containing the pharmaceutical composition according to claim 1.

17. A method for treating a tumor or cancer comprising administering to a subject an effective amount of the pharmaceutical composition according to claim 1;

wherein the tumor or cancer is selected from the group consisting of head and neck squamous cell carcinoma, head and neck cancer, brain cancer, neuroglioma, glioblastoma multiforme, neuroblastoma, central nervous system carcinoma, neuroendocrine tumor, throat cancer, nasopharyngeal cancer, esophageal cancer, thyroid cancer, malignant pleural mesothelioma, lung cancer, breast cancer, liver cancer, hepatoma, hepatobiliary cancer, pancreatic cancer, gastric cancer, gastrointestinal cancer, intestinal cancer, colon cancer, colorectal cancer, kidney cancer, clear cell renal cell carcinoma, ovarian cancer, endometrial cancer, cervical cancer, bladder cancer, prostate cancer, testicular cancer, skin cancer, melanoma, bone cancer, chondrosarcoma, Krukenberg tumor, squamous cell carcinoma, Ewing's sarcoma, and Merkel cell carcinoma.

18. The pharmaceutical composition according to claim 1, wherein the anti-Claudin18.2 antibody drug conjugate has a structure of the formula shown below:

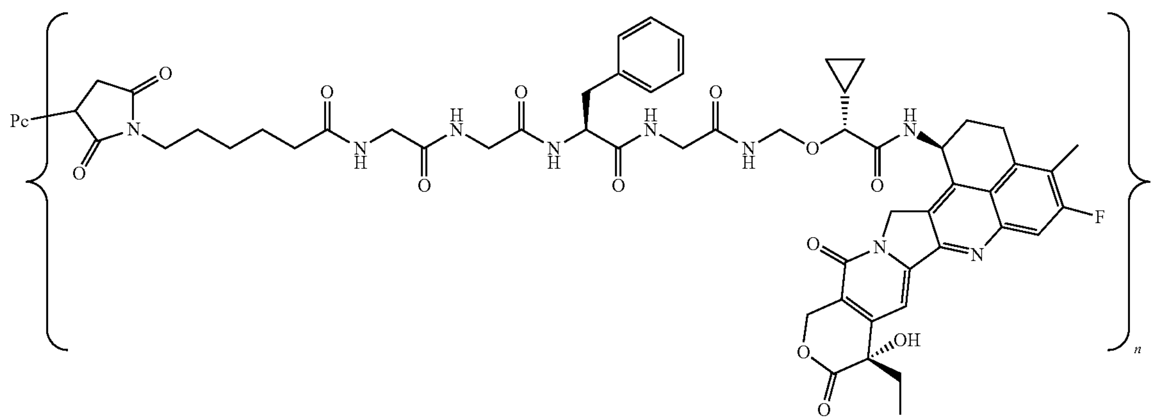

12. A lyophilized formulation comprising an antibody drug conjugate, wherein the formulation can be reconstituted to form the pharmaceutical composition according to claim 1.

13. A method for preparing a lyophilized formulation comprising an antibody drug conjugate, comprising a step of lyophilizing the pharmaceutical composition according to claim 1.

14. A lyophilized formulation comprising an antibody drug conjugate, wherein the formulation is obtained by lyophilizing the pharmaceutical composition according to claim 1.

15. A reconstituted solution comprising an antibody drug conjugate, wherein the reconstituted solution is prepared by reconstituting the lyophilized formulation according to claim 12.

wherein:

n is a decimal or an integer from 2 to 8;

Pc is an anti-Claudin18.2 antibody.

19. The method of claim 17, wherein the lung cancer is selected from the group consisting of non-small cell lung cancer and small cell lung cancer.

20. A pharmaceutical composition, comprising:

an anti-Claudin 18.2 antibody drug conjugate at a protein concentration of 20 mg/mL, 0.2 mg/mL polysorbate 80, 40 mg/mL sucrose, and 30 mM histidine-acetate buffer;

the pharmaceutical composition having a pH of 5.0 to 5.3;

the anti-Claudin18.2 antibody drug conjugate having a structure of the formula shown below:

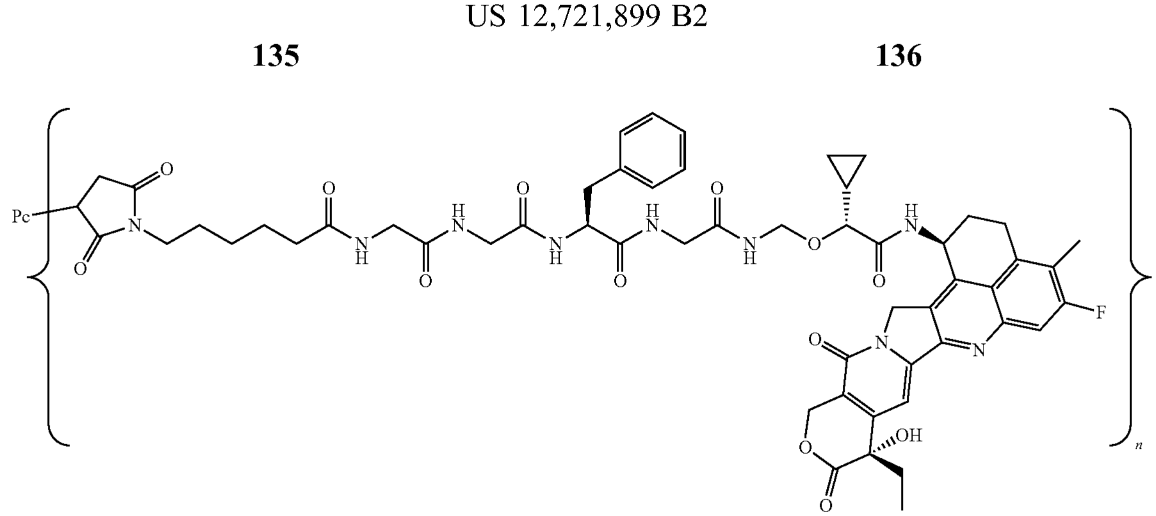
wherein:
n is a decimal or an integer from 2 to 8;
Pc is an anti-Claudin 18.2 antibody comprising a heavy chain set forth in SEQ ID NO: 49 and a light chain set forth in SEQ ID NO: 47.
* * * * *